US009332937B2

(12) United States Patent
Currie et al.

(10) Patent No.: US 9,332,937 B2
(45) Date of Patent: May 10, 2016

(54) SYSTEMS AND METHODS FOR MONITORING HEALTH AND DELIVERING DRUGS TRANSDERMALLY

(71) Applicants: Georgetown University, Washington, DC (US); Leidos, Inc., Reston, VA (US)

(72) Inventors: John F. Currie, Bethesda, MD (US); Makarand Paranjape, Silver Spring, MD (US); Carl C. Peck, Rockville, MD (US); Robert White, Fairfax, VA (US); Thomas W. Schneider, Gaithersburg, MD (US)

(73) Assignees: Georgetown University, Washington, DC (US); Leidos, Inc., Reston, VA (US)

( * ) Notice: Subject to any disclaimer, the term of this patent is extended or adjusted under 35 U.S.C. 154(b) by 196 days.

(21) Appl. No.: 14/036,966

(22) Filed: Sep. 25, 2013

(65) Prior Publication Data
US 2014/0025000 A1 Jan. 23, 2014

Related U.S. Application Data

(60) Continuation of application No. 13/085,775, filed on Apr. 13, 2011, now Pat. No. 8,568,315, and a division of application No. 11/090,156, filed on Mar. 28, 2005, now Pat. No. 7,931,592, and a continuation of (Continued)

(51) Int. Cl.
*A61M 5/172* (2006.01)
*A61B 5/145* (2006.01)
(Continued)

(52) U.S. Cl.
CPC ......... *A61B 5/150007* (2013.01); *A61B 5/0059* (2013.01); *A61B 5/1455* (2013.01);
(Continued)

(58) Field of Classification Search
USPC ......... 600/309, 310, 322, 323, 324, 316, 473, 600/476, 317; 604/503, 504
See application file for complete search history.

(56) References Cited

U.S. PATENT DOCUMENTS 4,526,176 A 7/1985 Bremer et al.
4,708,716 A 11/1987 Sibalis
(Continued)

FOREIGN PATENT DOCUMENTS

EP 0942278 B1 9/1999
JP H01-158343 6/1989
(Continued)

OTHER PUBLICATIONS

Patent Examination Report No. 1 for Application No. AU 2013201044, dated Jan. 20, 2014, 4 pp.
(Continued)

*Primary Examiner* — Eric Winakur
(74) *Attorney, Agent, or Firm* — Dawn-Marie Bey; Bey & Cotropia PLLC

(57) ABSTRACT

The present invention pertains to a system and method for transdermal sampling, comprising: at least one sampler for retrieving and transferring at least one analyte obtained transdermally from the skin of a subject; at least one detector system for identifying and quantifying said at least one analyte; and at least one logic module for (i) receiving and storing input data from said at least one detector, (ii) relating the input data to other data obtained from the subject, (iii) displaying output information, (iv) transmitting the output information to another system, and (v) controlling the operation of said at least one sampler and at least one detector.

20 Claims, 24 Drawing Sheets

Related U.S. Application Data application No. 09/866,826, filed on May 30, 2001, now Pat. No. 6,887,202.

(60) Provisional application No. 60/208,327, filed on Jun. 1, 2000.

(51) Int. Cl.
*A61B 5/15* (2006.01)
*A61B 5/00* (2006.01)
*A61B 5/1455* (2006.01)
*A61B 5/1486* (2006.01)

(52) U.S. Cl.
CPC ......... *A61B5/14514* (2013.01); *A61B 5/14532* (2013.01); *A61B 5/14546* (2013.01); *A61B 5/6833* (2013.01); *A61M 5/1723* (2013.01); *A61B 5/1486* (2013.01); *A61B 2562/12* (2013.01)

(56) References Cited

U.S. PATENT DOCUMENTS

| | | | |
|---|---|---|---|
| 4,775,361 | A | 10/1988 | Jacques et al. |
| 4,821,733 | A | 4/1989 | Peck |
| 4,909,256 | A | 3/1990 | Peck |
| 5,123,902 | A | 6/1992 | Muller et al. |
| 5,176,881 | A | 1/1993 | Sepaniak et al. |
| 5,203,327 | A | 4/1993 | Schoendorfer et al. |
| 5,330,527 | A | 7/1994 | Montecalvo et al. |
| 5,362,307 | A | 11/1994 | Guy et al. |
| 5,380,272 | A | 1/1995 | Gross |
| 5,458,140 | A | 10/1995 | Eppstein et al. |
| 5,591,139 | A | 1/1997 | Lin et al. |
| 5,722,397 | A | 3/1998 | Eppstein |
| 5,730,714 | A | 3/1998 | Guy et al. |
| 5,801,057 | A | 9/1998 | Smart et al. |
| 5,885,211 | A | 3/1999 | Eppstein et al. |
| 6,056,738 | A | 5/2000 | Marchitto et al. |
| 6,124,597 | A | 9/2000 | Shehada et al. |
| 6,233,471 | B1 | 5/2001 | Berner et al. |
| 6,312,393 | B1 | 11/2001 | Abreu |
| 6,393,318 | B1 | 5/2002 | Conn et al. |
| 6,464,687 | B1 | 10/2002 | Ishikawa et al. |
| 6,730,212 | B1 | 5/2004 | Yamagishi et al. |
| 6,887,202 | B2 | 5/2005 | Currie et al. |
| 7,344,499 | B1 | 3/2008 | Prausnitz et al. |
| 7,655,477 | B1 | 2/2010 | Schneider et al. |
| 7,888,509 | B2 | 2/2011 | Wolf et al. |
| 7,931,592 | B2 | 4/2011 | Currie et al. |
| 2005/0182307 | A1 | 8/2005 | Currie et al. |
| 2006/0115857 | A1 | 6/2006 | Keen |
| 2009/0308742 | A1 | 12/2009 | Paranjape |
| 2011/0042225 | A1 | 2/2011 | Adeloju |
| 2012/0010487 | A1 | 1/2012 | Currie et al. |

FOREIGN PATENT DOCUMENTS

| | | |
|---|---|---|
| JP | H05-172815 | 7/1993 |
| JP | H07-000541 | 1/1995 |
| JP | H09-140687 | 6/1997 |
| WO | WO 97/42882 | 11/1997 |
| WO | WO 99/44507 | 9/1999 |
| WO | WO 99/58050 | 11/1999 |
| WO | WO 00/04832 | 2/2000 |
| WO | WO 00/15102 | 3/2000 |
| WO | 0108289 | 4/2000 |

OTHER PUBLICATIONS

International Search Report and Written Opinion for Application No. PCT/US14/19183, dated May 14, 2014, 7 pp.

Preliminary Examination Report for Application No. PCT/US01/17081, dated Sep. 15, 2004 (mailing date).

International Serach Report, date received Aug. 14, 2001.

"SpectRX An Innovative Medical Technology Company" [online], Copyright 2004 [retrieved on Aug. 31, 2004], 1 p., Retrieved from the Internet: http://www.spectrx.com.

Written Opinion for Application No. PCT/US01/17081, dated Feb. 31, 2004 (mailing date).

Schneider, T., et al., "B-Fit uSystem: Bio-Flips Integrable Transdermal MicroSystem," ARO Workshop on Biomolecular Signaling, Energy, Transfer, and Transduction Processes, Cashiers, NC, May 14-17, 2000, 16 pp.

Smith, Frederick P. and Kidwell, David A., "Cocaine in Hair, Saliva, Skin Swabs, and Urine of Cocaine Users' Children," Forensic Science Intl., vol. 83, pp. 179-189, 1996.

Balabanova, Von Svetla and Schneider E., "Detection of Drugs in Sweat (Nachweis von Drogen im SchweiB)," Beitr. Gerichtl. Med., vol. 48, pp. 45-49, 1990.

Peck, Carl C., et al., "Outward Transcutaneous Chemical Migration: Implications for Diagnostics and Dosimetry," Skin Pharmacol., vol. 1, No. 1, pp. 14-23, 1988.

Supplementary European Search Report for Application No. EP 01 93 9501, dated Jan. 11, 2011.

Phillips, Michael and McAloon, Margaret H., "A Sweat-Patch Test for Alcohol Consumption: Evaluation in Continuous and Episodic Drinkers," Alcohol: Clinical and Experimental Research, vol. 4, No. 4, pp. 391-395, 1980.

Henderson, Gary L. and Wilson, B. Kent, "Excretoin of Methadone and Metabolites in Human Sweat," Research Communications in Chemical Pathology and Pharmacology, vol. 5, No. 1, pp. 1-8, Jan. 1973.

Paranjape, et al., "A PDMS Dermal Patch for Non-Intrusive Transdermal Glucose Sensing," Sens. Actuat. A, 2003, vol. 104, pp. 195-204 (2003), Entire Document.

Connolly, et al., "Minimally Invasive Sensing," Ch. 18 of "Biosensors—Emerging Materials and Applications," Jul. 2011, ISBN: 978-953-307-328-6, pp. 355-382 (Jul. 2011), entire documents [online], download from: http://cdn.intechweb.org/pdfs/16435.pdf> on Mar. 30, 2013.

PCT Communication for application No. PCT/US2013/27126 filed Feb. 21, 2013, "Notification of the International Search Report and the Written Opinion of the International Searching Authority, or the Declaration," Apr. 26, 2013.

Zhang, et al., J. Matl. Sci. Matls. in Medicine 16 (2005), pp. 933-946.

Martinez, et al., PNAS 105(5), 19606-19611 (2008).

Martinez, et al., Anal. Chem., 82:3-10 (2010).

Abe, et al., Analyt. Chem. 80 (2008) (6928-6934).

Li, et al., Analyt. Chem. 80 (2008) (9131-9134).

Chronakis, et al., Polymer 47(5):1597-1603 (2006).

Miao, et al., J. Nanosci. Nanotech. 10:5507-5519 (2010).

Shiroma, et al., Analytica Chimica Acta 725 (2012) (44-50).

Dungchai, et al., Analyt. Chem. 81 (2009), 5821-5826.

Liu, et al., Matl. Sci. Eng. C27(1):57-60 (Jan. 2007).

Yamada, et al., Chem. Lett. 26(3):201-202 (1997).

Fortier, et al., Biosens. Bioelectronics 5:473-490 (1990).

SYSTEMS AND METHODS FOR MONITORING HEALTH AND DELIVERING DRUGS TRANSDERMALLY

CROSS-REFERENCE TO RELATED APPLICATIONS

This application is a continuation of and claims priority to application Ser. No. 13/085,775, filed Apr. 13, 2011, entitled "SYSTEMS AND METHODS FOR MONITORING HEALTH AND DELIVERING DRUGS TRANSDERMALLY," which is a divisional of and claims priority to application Ser. No. 11/090,156, filed Mar. 28, 2005, entitled "SYSTEMS AND METHODS FOR MONITORING HEALTH AND DELIVERING DRUGS TRANSDERMALLY," which is a continuation of and claims priority to U.S. patent application Ser. No. 09/866,826, filed May 30, 2001, entitled "SYSTEMS AND METHODS FOR MONITORING HEALTH AND DELIVERING DRUGS TRANSDERMALLY," which claims priority to Provisional Application Ser. No. 60/208,327, filed Jun. 1, 2000 entitled "TRANSDERMAL HEALTH MONITORING AND DRUG DELIVERY SYSTEM," all of which are incorporated herein by reference in their entirety.

GOVERNMENT RIGHTS INVENTION

Worked described herein was funded, in whole or in part, by the DARPA Contract #DAAD19-00-1-0390. The United States Government has certain rights in the invention.

BACKGROUND OF THE INVENTION

1. Field of the Invention

The present invention relates generally to portable biomedical monitoring. More specifically, this invention relates to non-invasive and minimally invasive molecular monitoring, and optionally the implementation of protective feedback measures and remote monitoring through telemetry.

2. Description of the Related Art

Non-invasive transdermal sampling of body fluids has long been a goal in medical research. The notion that valuable diagnostic information comprising the concentrations of key analytes within the bloodstream could be obtained without breaching the skin has spurred many lines of research. With such technology, long-term convenient health monitoring and screening without needles or outpatient care would become a reality: diabetics could monitor blood glucose without drawing blood; markers for microbial, fungal or viral infections could be monitored; and environmental exposure to toxins could be assessed non-invasively.

Biomarkers have been utilized effectively to detect, measure, and assess exposure levels to environmental chemicals deemed hazardous and toxic to human life. The sensitivity of biomarkers allows them to act as early warning indicators to subtle alterations in the environment. Their specificity can be used to establish the nature of the imposing chemical agent, determine exposure level and define a suitable course of action. Environmentally induced diseases affect everyone to one degree or another, however individual susceptibilities can predispose the degree of toxic reaction of one group over another. It is worthwhile noting that in 1996, there were 86,912 cases of pesticide exposures reported to American Association of Poison Centers, of which 26 were fatalities. In particular, individuals in their developmental stages, ranging from the embryonic phase to adolescence, are particularly susceptible to such environmental stresses since key body functions have not matured to a level where they can tolerate, process and handle such exposures. The use of biomarkers for determination of children's environmental health will allow for the early detection of toxins, prevention of impairment in their physical condition, and determine a course of treatment for children who have been exposed to a toxic environment.

Especially important in the field of pediatrics is the use of health evaluation tools that are minimally intrusive.

Many transdermal sampling techniques have been reported, but all to date suffer from one or more serious drawbacks. Conventional techniques have disadvantages of being grossly invasive (and potentially injurious) and sweat or interstitial fluid dependent, except for the: passive, non-sweat dependent transdermal analyte collection and detection techniques.

One approach to transdermal sampling has employed the collection of sweat. For example, M. Philips and M. H. McAloon, Alcohol Clin. Exp. Res. 4 391 (1980) disclose an absorbent patch which is a salt-impregnated, cellulose pad under an occlusive, adhesive cover. However, such a method of transdermal sampling is dependent upon the sweat rate, requires sweat extraction by centrifugation, and calls for external chemical analysis. S. Balabanova and E. Schneider, Beitr. Gerichtl, Med 48, 45 (1990), disclose Pilocarpine-induced sweat secretion, but the system requires Iontophoresis-induced infusion of pilocarpine and analyte dilution. U.S. Pat. No. 5,203,327, issued to Schoendorfer, et al., discloses an absorbent pad under a water vapor-permeable, occlusive, adhesive cover, but the system is sweat rate dependent and requires chemical extraction and external chemical analysis. F. P. Smith and D. A. Kidwell, Forensic Sci. Int. 83, 179 (1996), discloses a cotton sweat wipe, but this system is sweat volume-dependent and requires extraction and external chemical analysis. G. L. Henderson and B. K. Wilson, Res. Commun. Chem. Pathol. Pharmacol., 5, 1 (1973), discloses the collection of liquid sweat following exercise, but the system requires vigorous exercise, is sweat volume-dependent, and requires extraction and external chemical analysis.

C. C. Peck, D. P. Conner, et al., Skin Pharmacol., 1, 14 (1988), discloses a gel with an analyte binding reservoir under an occlusive adhesive cover. However, this reference requires extraction and external chemical analysis.

U.S. Pat. No. 4,909,256, issued to Peck discloses a dry binding reservoir under an occlusive adhesive cover. However, this reference requires extraction and external chemical analysis.

U.S. Pat. No. 4,821,733, issued to Peck discloses a collection and detection system under an occlusive adhesive cover. However, this reference requires highly sensitive detection components.

U.S. Pat. No. 4,775,361, issued to Jacques discloses enhanced migration of analyte to a skin surface. However, this reference requires introduction of light energy into the body.

U.S. Pat. No. 5,362,307, issued to Guy discloses iontophoretic enhanced analyte collection across skin. However, this reference requires the introduction of electrical energy into the body.

U.S. Pat. No. 5,722,397, issued to Eppstein discloses ultrasound enhanced analyte collection across skin. However, this reference requires the introduction of sonic energy and chemicals into the body.

U.S. Pat. No. 5,885,211, issued to Eppstein, discloses micropore formation using heated water vapor, physical lancet, sonic energy, high pressure jet of fluid, or electricity. However, this reference requires puncture of the skin using heat, sonic, or electrical energy, physical or hydraulic force.

The website www.spectrx.com discloses the application of vacuum to laser-induced dermal micropores for harvesting of interstitial fluid. However, this reference requires introduction of sonic energy into body, as well as physical energy to harvest interstitial fluid and may cause an inflammatory reaction.

There is, therefore, a need within the transdermal sampling field for a minimally invasive sampling technique and apparatus suitable for rapid, inexpensive, unobtrusive, and pain-free monitoring of important biomedical markers and environmental toxin exposure. These properties and advantages of the present invention will become apparent to those of skill in the art upon reading the following disclosure.

BRIEF SUMMARY OF THE INVENTION

The present invention pertains to a transdermal sampling system, comprising: at least one sampler for retrieving and transferring at least one analyte obtained transdermally from the skin of a subject; at least one detector system for identifying and quantifying said at least one analyte; and at least one logic module for (i) receiving and storing input data from said at least one detector, (ii) relating the input data to other data obtained from the subject, (iii) displaying output information, (iv) transmitting the output information to another system, and (v) controlling the operation of said at least one sampler and at least one detector.

The present invention also pertains to a microfabricated device for allowing remote monitoring of a subject, comprising: at least one sampler unit body for retrieving and transferring at least one analyte obtained transdermally from the skin of a subject; at least one detector system connected to said at least one sampler unit body for identifying and quantifying at least one analyte obtained from a subject; and a transmitter/receiver for transmitting data relating to at least one analyte detected by said detection system to a logic module for processing thereby, and for allowing control of the microfabricated device by a logic module.

The present invention also pertains to a microfabricated device for sampling analytes from the skin of a subject, comprising: a detection chamber for receiving analytes retrieved from the skin of a subject; a photonic detection system, comprising a photonics source located attached to said microfabricated device in association with said detection chamber, and detectors associated with said detection chamber for detecting analytes received in said detection chamber.

The present invention also pertains to a microfabricated device for sampling analytes from the skin of a subject, comprising: a detection chamber for receiving analytes retrieved from the skin of a subject; a patch which changes color when contacted by predetermined analytes, located attached to said microfabricated device in association with said detection chamber; and detectors associated with said detection chamber, for detecting a change of color of the patch indicating the presence of a predetermined analyte.

The present invention also pertains to a microfabricated device for sampling and detecting analytes retrieved from the skin of a subject, comprising: at least one conduit for retrieving and transmitting an analyte from the skin of a subject to a detector; and means for enhancing permeability of the skin of a subject for retrieving said at least one analyte therefrom.

It is an object of the present invention to provide a transdermal sampling system.

It is another object of the present invention to provide an integrated detection system using patch type detector.

It is still another object of the present invention to provide an integrated detection system using integrated photonics.

It is a further object of the present invention to provide a microfluidic perfusion system for enhancing transdermal transfer of biological molecules.

It is yet another object of the present invention to provide a thermal ablation mechanism by resistive heating for removal of the stratum corneum.

It is still another object of the present invention to provide a laser ablation mechanism for removal of stratum corneum.

It is a further object of the present invention to provide a microfluidic transfer of fluids utilizing capillary action.

It is another object of the present invention to provide an adhesive for holding transdermal sampling system on skin.

It is another object of the present invention to provide a chemical modification of channel surfaces with antibodies containing fluorescently labeled antigens that are expelled from the surface and detected down stream by competitive binding.

A greater understanding of the present invention and its concomitant advantages will be obtained by referring to the following figures and detailed description provided below.

DETAILED DESCRIPTION OF THE PREFERRED EMBODIMENTS

The present invention provides an enhanced system and method for monitoring the health of an individual and delivering drugs to an individual transdermally. Specifically, the present invention provides an integrated, cost-effective, rapid and unobtrusive assessment of a subject's medical condition. The invention further provides means for transdermal delivery of drugs in response to the aforementioned assessment of a subject's medical condition. Embodiments include, for example, monitoring a subject for pesticide exposure, monitoring the stress status of a war-fighter; phenotyping using the enzyme N-acetyl transferase to indicate an infected or diseased state; monitoring external exposure and internal contamination of a person with either organophosphate nerve agents (tabun, sarin, soman) or organophosphate insecticides (parathion and metabolites thereof); monitoring inflammatory sequeli in response to microbial infection (interleukin-1, interleukin-6, tumor necrosis factor); monitoring microbial toxins (anthrax, botulinum, endotoxin); monitoring spore metabolites arising from human catabolism via lymphatic or hepatic pathways; monitoring stimulants such as caffeine, antihistamines (dexomethorphan, caffeine); monitoring stress through alterations in blood glucose concentration or altered metabolism of insulin/glucose.

Figure 1:
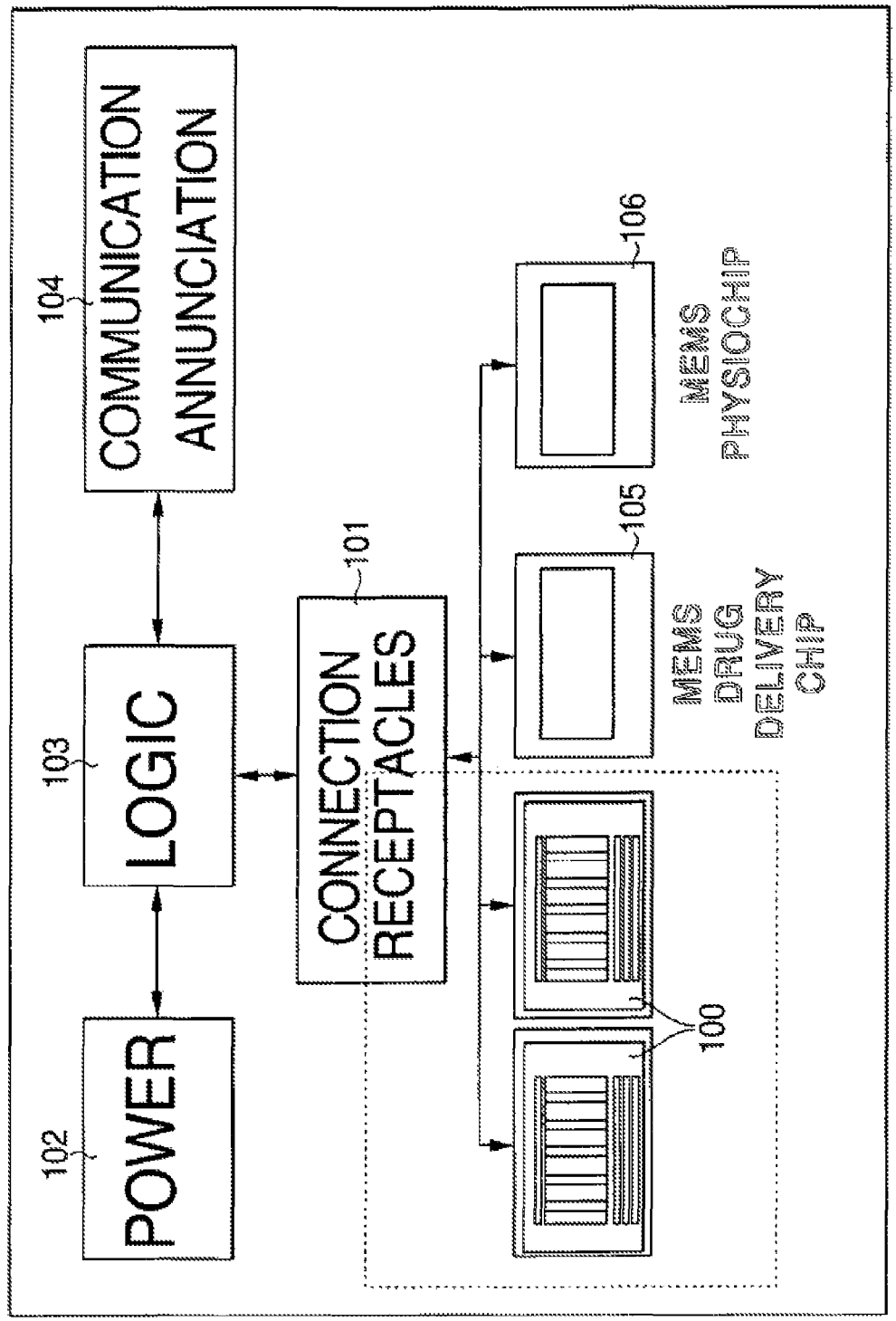
FIG. 1 is a schematic illustration of the overall architecture of the microsystem of the present invention.
Figure 2:
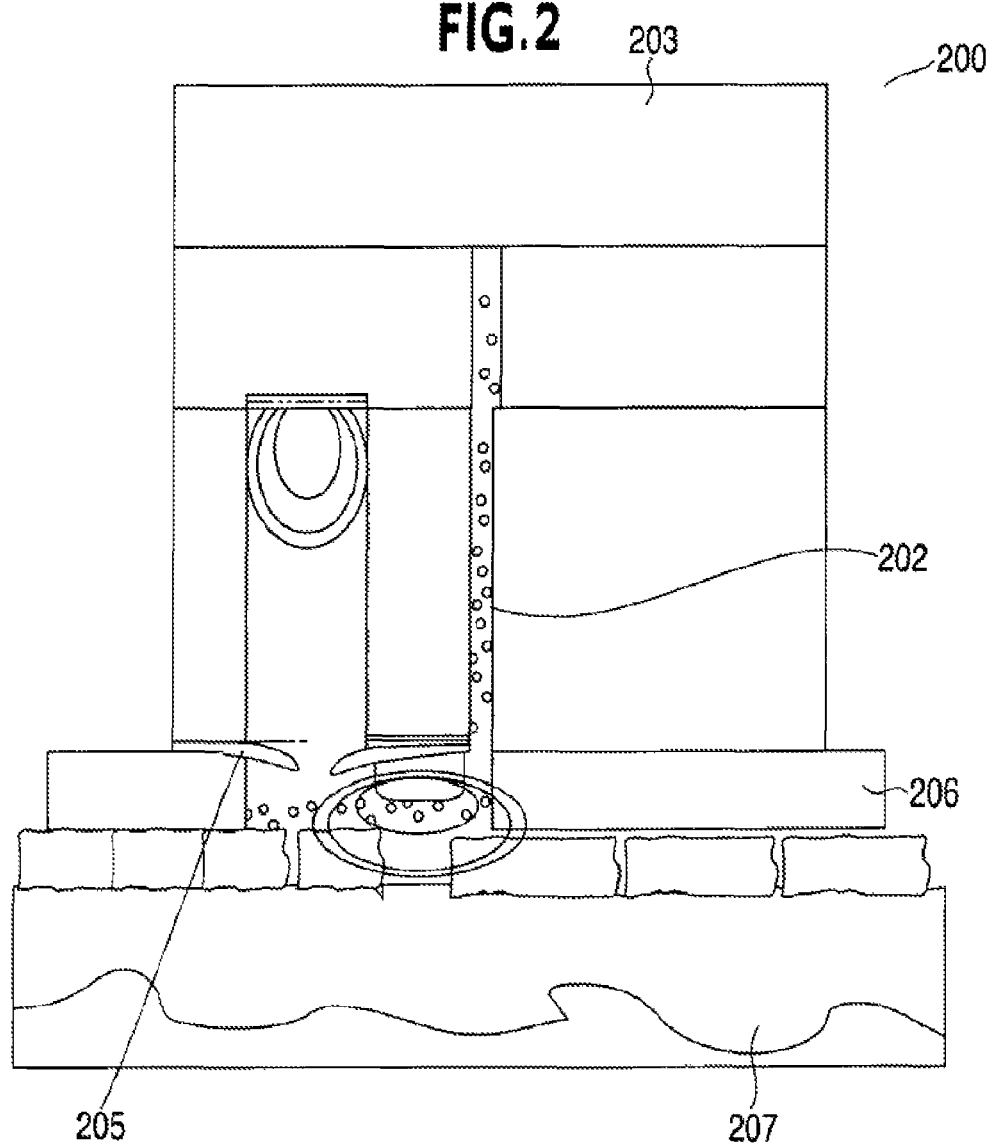
FIG. 2 illustrates in cross-section a single reservoir capillary pair.

An overall architecture of a preferred embodiment of the present invention is shown in FIG. 1. The disposable B-FIT 100 is adapted to detect analytes of interest and is mounted in a receptacle 101 to provide mechanical support and electrical connections, including electrical connections to the thermal heaters of the B-FIT. The connection receptacle 101 also accurately aligns the B-FIT with respect to a switchable photonic backplane. The connection receptacle also preferably contains a power source 102; logic control 103; and electronic circuits for power management, electronic storage of results, electronic circuits for processing biochemical analysis data, electronic circuits for timing events, and means for communicating results 104 either directly or via telemetry. Optical components are provided, preferably located within B-FIT 100 or MEMS physiochip 106. In one embodiment, fluorescence measurements are made sequentially upon each of a plurality of analysis chambers contained in the B-FIT. Drug delivery chips 105 are also optionally provided by the present invention and are used to deliver potent drugs transdermally, for example, drugs used to counteract nerve gas may be delivered. In addition, a physiochip 106 is optionally provided that gathers continuous basic vital information, including blood pressure and pulse rate.

The transdermal subsystem, located within the B-FIT and drug delivery chip, functions to contact the skin with a physiologically compatible solution or a physiologically compatible solution containing a drug. The B-FIT is organized into a dense array of somewhat independent single reservoir capillary pairs. The capillary pairs each comprise a reservoir capillary 211 for retaining a physiologically compatible solution, the reservoir having a breakable seal 215 (illustrated in a ruptured state), and an adjacent transport capillary 212 for transporting physiologically compatible solution, which has contacted skin, to an analyte measuring site. An adhesive layer 216 is provided upon the lower surface of the BFIT. In use, the adhesive layer is interposed between the lower surface of the B-FIT and the skin, and attaches the B-FIT to the skin.

In a preferred embodiment, a thermal perforation subsystem functions to ablate a microscopic portion of the stratum corneum, the topmost layer of skin, so that the interstitium can be exposed. The thermal perforation subsystem is preferably comprised of a micro-heater in close proximity to the skin surface, together with electrical components that control current to the micro-heaters.

A capillary array subsystem is preferably provided microfabricated into silicon wafers that comprise the B-FIT. The invention preferably provides a plurality of capillary-array subsystems, each of which comprises a fluid delivery chamber or reservoir chamber 201 to deliver a fluid to the skin surface, a capillary channel 202 to recover fluid from the skin surface, and at least one transverse capillary channel in which the analyte or analytes are detected. The B-FIT 200 is preferably comprised of a multilayered assembly of micromachined silicon wafers: a first wafer 204, a second wafer 206, and a detection layer 203. The detection layer preferably comprises a photonics system for visible or fluorescence measurements, or a layer that comprises colorimetric reagents that develop a color change in the presence of an analyte, or other means for detection of an analyte. The capillary subsystem thus preferably comprises capillaries for storage, passage and analysis of physiological fluids. The diameter and surface coatings of the capillaries are preferably optimized for controlling flow of the fluid and to prevent non-specific absorption of fluid components onto the capillary walls.

An optional integrated photonics system is provided by the present invention to determine, either qualitatively or quantitatively, the presence of one or more analytes. The integrated photonics system comprises waveguides, lenses, mirrors, light sources, and light detectors. Preferably, the integrated photonics system is housed within connection receptacle 101, which is attached to a surface of B-FIT 100 that faces away from the skin. In some embodiments, the integrated photonics subsystem is replaced by a colorimetric analyte sensitive region, wherein a color change, perceived directly by an observer, indicates the presence of an analyte.

Each of these subsystems and the interactions between the subsystems is described in greater detail below.

The B-FIT preferably contains an array of somewhat independent analyte sensing devices, termed "single reservoir capillary pairs" 200. As used herein, the term "physiological fluid" represents a fluid that is biologically compatible with living tissue, and is, therefore, isotonically and otherwise physiologically (for example, pH) suitable as a medium for contacting, for example, viable epidermal cells or cells of the stratum corneum. An example of a physiological solution within the current meaning is physiological saline solution. Each single reservoir capillary pair preferably contains a reservoir capillary 201 that stores and releases a physiological fluid to irrigate the skin surface or a small region of the stratum corneum and recover analytes. A breakable seal 205 is preferably provided to control the timing of the release of the fluid to irrigate the skin. The fluid is preferably recovered into a capillary channel 202 that carries the fluid to an analysis location, for example a detection patch 203. The transdermal subsystem preferably utilizes single reservoir capillary pairs to ensure that the analyte of interest, if present, is accessible to the fluid.

As the term is used in the present application, "transdermal dosimetry" refers to the collection and detection of trace quantities of analytes that reach the surface of the skin by passive diffusion from interstitial fluid underlying the outermost layer of skin, the stratum corneum. It will be appreciated that, in one embodiment of the present invention, the interstitial fluid is sampled for the presence of analytes of interest. It will further be appreciated that, in another embodiment of the present invention, ablation of a microscopic portion of stratum corneum enables the physiologic solution from the reservoir to come into contact with the upper region of the underlying viable epidermis, enabling analytes in interstitial fluid to migrate into the physiologic solution via passive diffusion for analysis.

"Non-invasive transdermal detection," as the term is used in the present application, means detection of substances below the skin that is achieved without physical or chemical modifications of the normal skin barrier. Small molecular weight analytes that exhibit both water and lipid solubilities can be sampled by non-invasive techniques.

Figure 3:
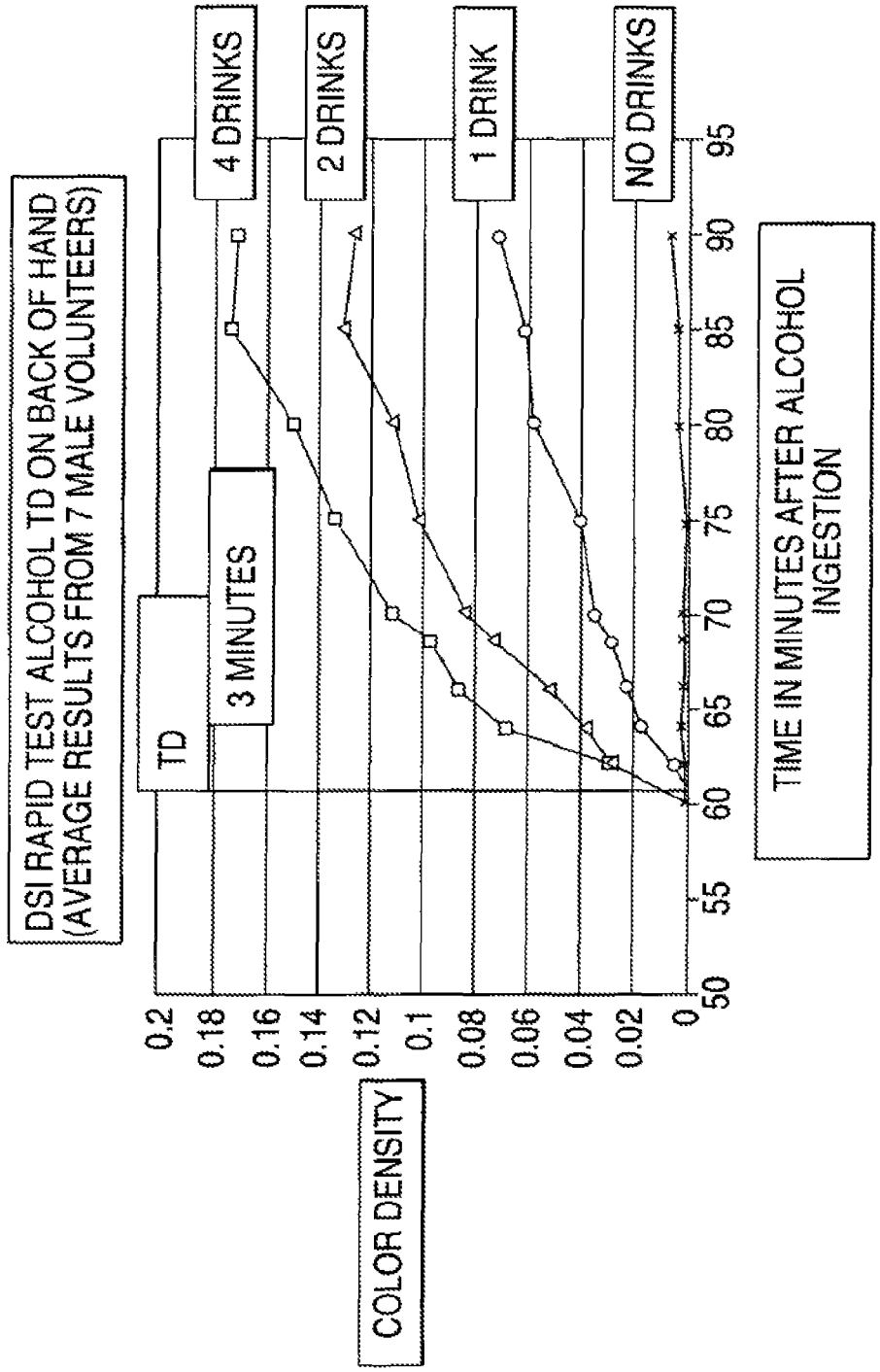
FIG. 3 shows test results obtained for a back of the hand colorimetric test for blood alcohol.

For example, sweat can be sampled from the surface of the skin and analyzed for alcohol content by a colorimetric test indicative of blood alcohol concentration, as illustrated in FIG. 3. In this example of non-invasive detection, alcohol is detected in sweat obtained from the backs of the hands of seven male subjects who have ingested 0-4 alcoholic drinks prior to the test. Alcohol contained in the sweat reacts with reagents contained within a reactive layer, resulting in a quantitative measure of alcohol content of the blood.

However, non-invasive techniques are not practical where the analyte has a high molecular weight (for example, protein), is highly polar (for example, glucose), or is poorly soluble. The outward flux of such molecules across the skin can be greatly enhanced by ablation of the stratum corneum. Ablation is performed to a typical depth of 30-60 μm, exposing the underlying viable epidermis, from which fluid can be collected and analyzed for analytes that only poorly penetrate unablated stratum corneum. This technique is herein termed "minimally invasive" because only the stratum corneum is ablated while the underlying viable epidermis is not breached. In one preferred embodiment of the present invention, minimally invasive transdermal detection is achieved by microscopic heat ablation of the stratum corneum layer. In another preferred embodiment of the present invention, minimally invasive transdermal detection is achieved by laser ablation of the stratum corneum layer.

An adhesive layer preferably provides an interface between the device of the present invention and the skin. The adhesive layer is affixed to the lower surface of the B-FIT assembly and functions to attach the B-FIT assembly to a suitable portion of skin surface, thereby minimizing motion of the B-FIT assembly relative to the skin for efficient sampling. Gaps in the adhesive layer are provided over each capillary pair to permit the physiological solution to contact the skin. The adhesive layer prevents leakage of fluid laterally, and is preferably comprised of a Band-Aid-type adhesive that is relatively water impermeable.

It will be appreciated that that portion of the B-FIT that interfaces with the dermis preferably functions to firmly and occlusively place the B-FIT system in direct contact with the external surface of skin (stratum corneum) or uppermost region of the viable epidermis. Occlusive contact are preferably such that prevent lateral or vertical movement of the B-FIT from its initial position on the skin, that limit release of B-FIT materials externally, and preclude entry of external materials. Movement preventive properties include preferably an adhesive element located peripherally on the lowermost surface of the B-FIT and/or covering the entire B-FIT and adjacent skin surface. Additionally, the lowermost surface of the B-FIT can be adhered to the dermis to prevent sheer forces that would displace the B-FIT from its initial position. The occlusive nature of the attachment of the B-FIT to the skin serves to confine all substances migrating from the body or skin within the B-FIT, including water vapor. This captured water vapor facilitates transdermal permeation by hydrating the stratum corneum, rendering it more permeable to a wide variety of analytes or therapeutic drugs.

In one preferred embodiment of the present invention, minimally invasive heat ablation of the stratum corneum is employed to achieve significant enhancement of the efflux of certain analytes. In preferred embodiments, thermal ablation is used to remove the stratum corneum over a microscopic region of the skin through a mechanism of resistive heating. A micro-ablation unit containing a micro-heater is preferably fabricated upon the surface of the B-FIT adjacent to each capillary pair, and provides a conductive heat path to the stratum corneum. The micro-heater preferably comprises a pair of electrodes connected by a conductive pathway that is arranged, either by the use of a resistive material or by a serpentine conductive pathway, to provide sufficient resistance to the flow of electricity such that an effective amount of heat is produced so as to locally ablate an appropriate portion of the stratum corneum. Electrical connections are also provided to each of the two electrodes to connect the micro-heating unit to a controller that controls the application of an electrical current source to the electrodes. In preferred embodiments, it is advantageous that the micro-heater protrude from the surface of the silicon substrate of the B-FIT to provide improved heat transfer to the stratum corneum and reduce the power consumption of the micro-heater. In one embodiment, a heat-sink material is incorporated on top of the micro-heater to direct the thermal flow towards the skin barrier rather than through the bulk silicon material. In another embodiment, the micro-heater is fabricated onto a silicon mesa that protrudes from the main silicon substrate of the B-FIT. Such an embodiment may preferably require non-planar fabrication of electrical connections to provide conducting pathways from the silicon mesa to the contiguous bulk silicon substrate. Such non-planar fabrication techniques are known to those of skill in the art, as illustrated in Paranjape, et al., Technical Digest, 1997 International Conference on Solid-State Sensors and Actuators, Chicago, Ill., Vol. 1, pp. 397 (1997), herein incorporated in its entirety by reference.

The thermal ablation micro-heater is pulsed with a suitable alternating or direct current to provide local ablation. Control of the duration and intensity of the heating pulse is preferably carried out to effect ablation of the correct area and depth. The micro-ablation preferably occurs in a confined volume of the stratum corneum of approximately 50 μm×50 μm×30 μm.

FIGS. 4(a) and 4(b) illustrate the seal structure as viewed (a) 5 from the bottom and (b) in cross-section.

A physiological compatible solution that may or may not contain one or more drugs is retained within the reservoir capillary 401 by a breakable seal 405 prior to use. The seal preferably provides an electronically addressable means for opening the reservoir capillary and contacting the skin surface or exposed stratum corneum to the physiological solution. The seal comprises a closure at the bottom end of the reservoir capillary and a means for opening the reservoir capillary. In a preferred embodiment, the seal comprises a thin membrane 400 that is preferably a dielectric bilayer that ruptures at elevated temperatures and a metal conducting path. Preferably, any thin, non-toxic, membraneous material that is sufficiently tough not to tear prior to intended use, is not electrically conducting, and ruptures at elevated temperatures is a suitable material for use as the seal closure. A preferred material is low-stress nitride. Control of the film stresses of the membrane is required during fabrication. Kinard, et al., IEEE Trans. on Inst. Meas., 46(2), 347 (1998), which is herein incorporated in its entirety by reference. To fabricate the seal, a metal conducting path 402 is surface deposited upon a low-stress silicon dielectric 400. Preferred metals for micro-heating elements include evanohm. Since the heat used to rupture the seal is optionally also used to ablate the skin in certain embodiments, a careful balance of film stresses, thickness and resistance is preferably achieved so as to provide both the desired heating and rupture properties. Deposition of the metal upon the film also requires deposition of metal upon an irregular topography. Such techniques are known to those of skill in the art. Geist, et al., NIST Journal of Research 95(6), 631 (1990), which is herein incorporated in its entirety by reference. The conductive path preferably terminates at two electrical contact pads 403, 404, to facilitate passage of electricity through conductive pathway 402. In a preferred mode of operation, an electrical current passing through the thin conductive pathway heats the metal of conductive pathway 402 and causes the rupturing of the underlying dielectric layer, thus, opening the reservoir capillary. It should be noted that an advantage of this preferred embodiment of the present invention and this preferred seal, in particular, is that mechanical moving parts are absent, thereby enhancing reliability.

In certain preferred embodiments, the seal seals both the reservoir capillary and the capillary channel, and both are thereby opened simultaneously.

Figure 5:
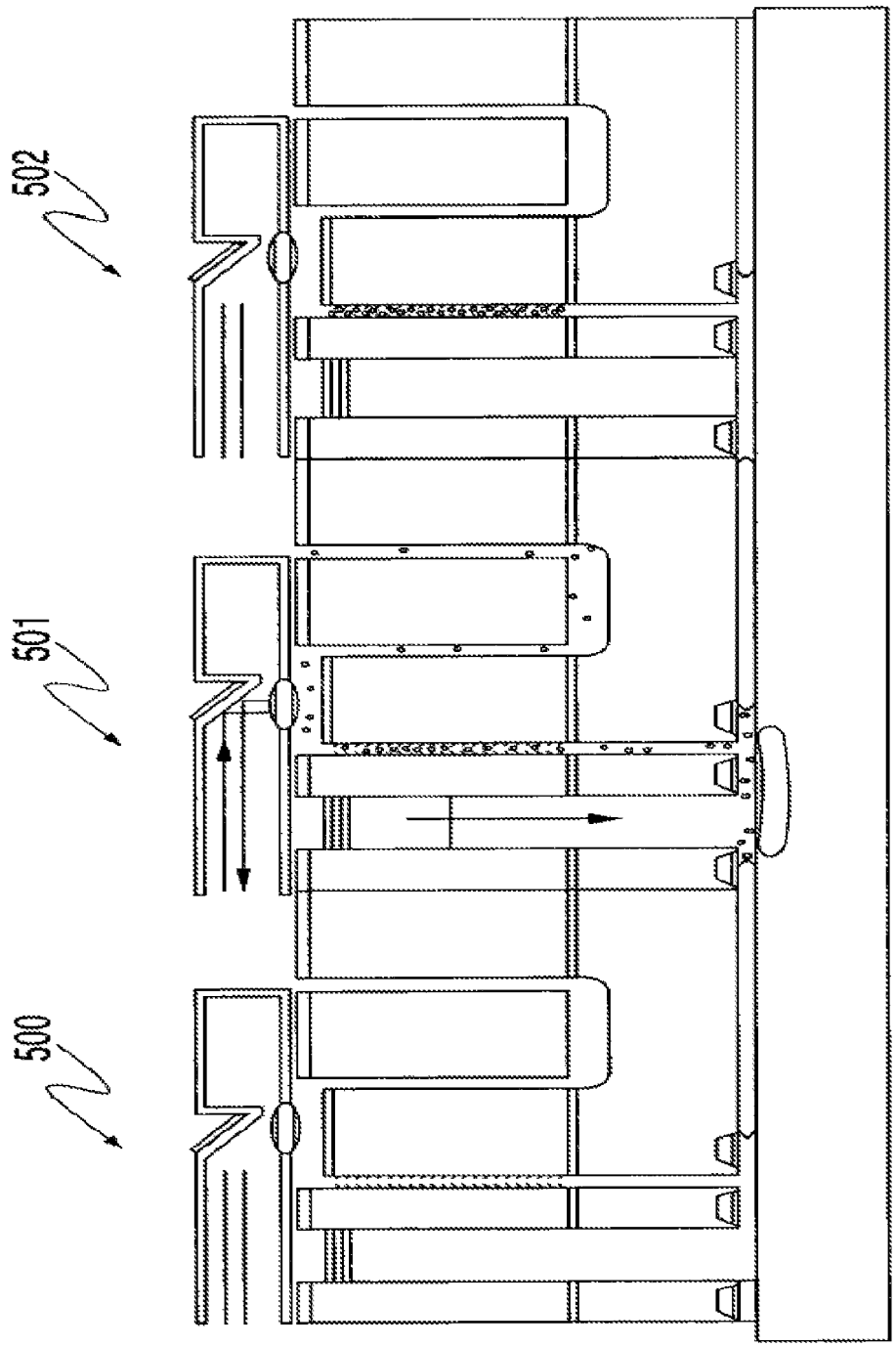
FIG. 5 is a cross-section of a device of the present invention illustrating the non-invasive sampling sequence.

FIG. 5 illustrates a B-FIT device cross-section, showing details on the non-invasive/minimally invasive sampling sequence. An exemplary unused capillary pair 502 has an intact seal wherein the physiological solution is retained within the reservoir capillary; upon application of a suitable electric current, the seal 501 is ruptured and the physiological compatible solution first contacts the skin and is then recovered into the transport capillary; and finally a used capillary with a ruptured seal 500 is illustrated. In this preferred embodiment, each capillary pair functions as a single-use unit so as to utilize the seal and physiological solution.

Figure 6:
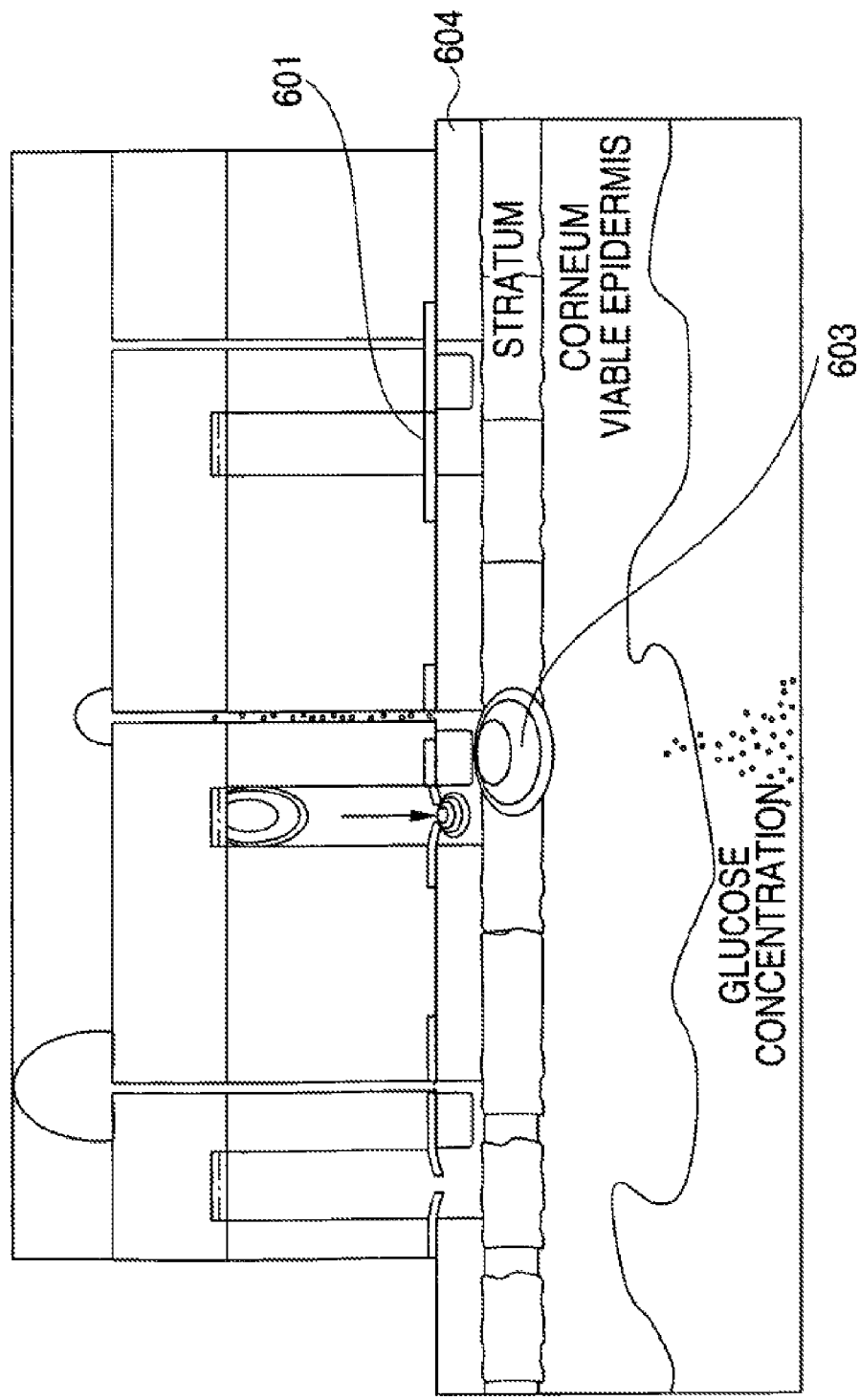
FIG. 6 is a cross-sectional view illustrating the sequence of operation of the Bio-Fluidic Integrable Transdermal (B-FIT) microsystem.

Similarly, FIG. 6 illustrates the sequence of operations of a minimally invasive embodiment of a B-FIT system to determine blood glucose concentration. A micro-heater 603 preferably operates to ablate a portion of the stratum corneum located below a gap in the adhesive layer 604 at the same time, or immediately prior to, rupture of the seal 601. Such a device provides an "on-demand" analysis. A physiological solution is preferably expelled onto the exposed viable epidermis and recovered into the transport capillary. The transport capillary preferably conducts the solution to a detection patch where the glucose is detected in a colorimetric reaction that produces a blue reaction. Note that in this preferred embodiment, the current pulses delivered to the micro-heater and the seal may be the same or different; the heater and seal may, therefore, be electrically connected either in series or parallel.

Figure 7:
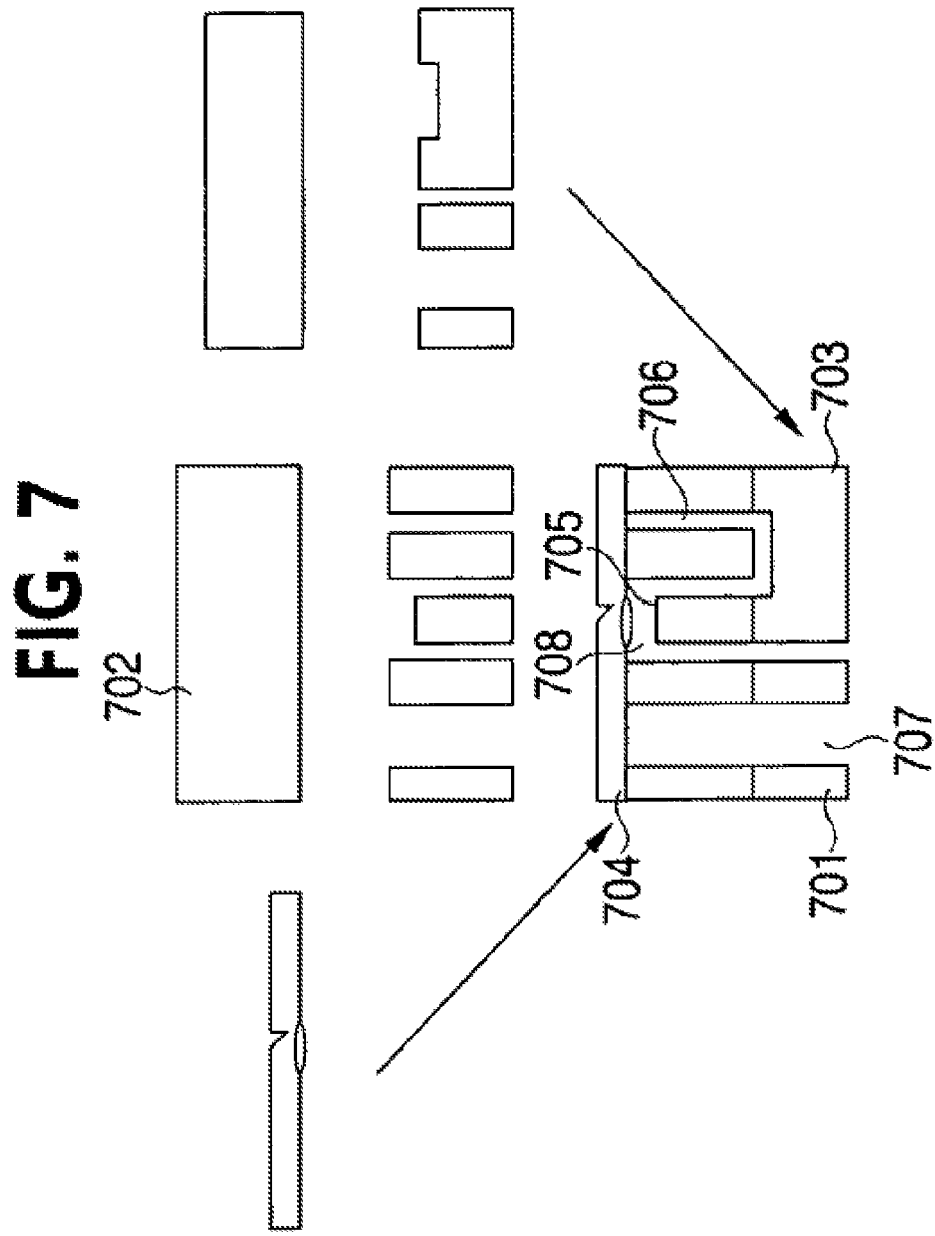
FIG. 7 schematically illustrates the basic fabrication steps for the three main components of the system, shown in cross-section.

Capillaries within the silicon body of the B-FIT device can preferably be fabricated by several techniques, for example by micro-machining, or by etching in place using deep resistive ion etching (DR1E) techniques. Referring now to FIG. 7, construction of a preferred embodiment of the B•FIT is illustrated. The device comprises three main parts: the main body 700 which is preferably made of silicon 702, and contains several serpentine capillary channels 706, each with its own reservoir channel 707; a bottom capping section 701 that forms the lower part of the serpentine structure and contains the micro-heating elements 703; and a top capping section 704, which forms the upper part of the serpentine channel 706, and which optionally contains electrodes for assisting the flow of physiological fluids using electro-osmotic pumping through the horizontal segments of the serpentine channel. The top-capping section 704 is, in some embodiments, bonded to the main body: an advantage of such an arrangement is good coupling of light into the capillary that is thereby achieved. The main body is preferably made of silicon. The main body 700 and the bottom capping section 701 are preferably permanently affixed to each other to comprise a sensor 705, that can, in certain embodiments, be detached from the top capping section 704 after use and replaced with a fresh array.

The reservoir and capillary channels are preferably fabricated within a standard silicon wafer. The dimensions of the capillaries are selected to facilitate the transport of sweat, interstitial fluid, or other physiological fluid, out of the open end of the reservoir under the force of gravity, and into a capillary channel through capillary action. In a preferred embodiment, the capillary channels are 25 µm in diameter and are approximately 500 µm in length, and the reservoir channels are 50 µm in diameter but are etched slightly shorter than 500 µm in length to provide a back wall. A lateral portion of the serpentine capillary channel 708 is provided, which provides for a region of fluid flow that is parallel and adjacent to the upper surface of the main body of the device for optical detection of analyte. The lower inside surface of the lateral portion is optionally provided with a reflective surface, such as a reflective metal coating, to facilitate optical detection. The lateral portion of the serpentine capillary is, in a preferred embodiment, completed by a surface of the top capping section. In use, the transport of physiological fluids and the recovery of analyte is enhanced by rinsing the skin with fluid previously maintained within the reservoir channel and then recovering the same into the corresponding capillary channel.

The surface of the capillary array system is preferably functionalized to improve the properties of the surface, for example to prevent absorption of protein, and/or to attach biomolecules such as antibodies to the surface. Molecules that bind specific analytes are used to immobilize analytes for subsequent detection and quantitative analysis. Suitable biomolecules include, but are not limited to, antibodies, antibody fragments, artificial antibodies, lectins, hybridizable nucleic acids, nucleic acid binding proteins, proteins that bind nucleic acids, proteins that bind other proteins, proteins that bind cofactors, cofactors (for example, flavins, pterins, thiamine, pyridoxals, quinone), and other reagents that specifically bind biological analytes.

Capillary tubes are preferably modified by either chemical or plasma treatment. This step aids surface cleaning of organic contaminants and introduces surface hydroxyl groups on the capillary surface, which are preferably reacted with a silane such as aminopropyl trimethoxysilane (APTS) to provide a free amine group as an anchor for coupling reagents such as antibodies. In a preferred embodiment, polyethylene glycol (PEG) silane derivatives are used to provide a surface coating that prevents absorption of protein.

In one embodiment, a solution containing antibodies directed to an analyte of interest is exposed to mildly oxidizing conditions known to those of skill in the art, which provides aldehyde groups upon the surface of the antibodies. The aldehyde functionality is then coupled to a free amine on the capillary tube surface via a Schiff base reaction, thus immobilizing the antibody to the capillary tube surface.

In a preferred embodiment, detection of the analyte of interest is done by means of fluorescence. A substance that is capable of specifically binding an analyte (for example, an antibody) 802 is covalently attached to the surface of the capillary, as described previously. The binding sites of the immobilized substance 802 are filled with fluorescently labeled analyte 801, prior to use of the invention. When analyte, 800, is present, it competes for the specific binding sites, displacing a portion of the labeled analyte molecules into the solution. The degree of displacement of labeled analyte depends upon the concentration of analyte in the solution. Therefore, measurement of the amount of fluorescence displaced into the solution, when suitably calibrated, provides a quantitative measure of the concentration of analyte 800.

By preferably immobilizing a plurality of antibodies of different binding specificity, the binding sites of which are separately filled with their respective analytes tagged with fluorophores with distinct emission and excitation spectra, multiple analyte determinations can preferably be made within a single capillary pair. The use of spectral filters and/or alternative light sources is used in a preferred embodiment to photoexcite and detect fluorescence from the different fluorophores, and thereby, determine the contribution of each fluorophore to the total fluorescent properties of the sample.

Preferred fluorophores for the present invention include rhodamines, fluoresceins, Texas red, Oregon green, Bidipy dyes, and aminonaphthalenes.

In one embodiment, N-acetyl transferase, isozyme 2, (NAT-2) activity is measured as a marker of adverse drug effects, toxicity and predisposition to disease. The NAT-2 phenotype can be detected, for example, by detecting the ratio of two metabolites of caffeine produced by NAT-2,5-acetylamino-6-formylamino-3-methyl uracil (AFMU) and 1-methylxanthine (1X). Utilizing the ratio of AFMU to 1X, the activity of NAT-2 can be determined. Polyclonal antibodies can be raised to these two metabolites and then purified. These antibodies can also be used to detect AFMU and 1X in urine samples by ELISA.

In a preferred embodiment of the present invention, the reservoir capillary is provided with a micro-heating element located at the opposite end of the capillary to the seal. The micro-heater is activated to provide local heating of the physiological fluid so as to produce a bubble, thereby forcibly expelling the physiological solution from the capillary once the seal is ruptured. Note that the micro-heater functions as a pump means, but that the pumping is achieved without mechanically moving parts, thereby assuring increased reliability.

The micro-heating elements are preferably comprised of a resistive conducting pathway deposited by conventional deposition methods upon the surface of the silicon. Unlike the breakable seal, the heating elements are designed to withstand elevated temperatures without destruction of the conductive pathway. The conductive pathway is, in one preferred embodiment, a serpentine pathway, in which a high-resistance pathway and localized heat generation are achieved through the use of a serpentine pathway comprised of thin conductive pathways densely arranged upon within a small surface area.

Another preferred aspect of the present invention is an integrated photonics analysis subsystem. The integration of photonics components into the B-FIT system permits increased density of assays, reduced size, lower power consumption, and decreased cost. In a preferred embodiment, the photonics components are housed within a plastic housing that comprises the top capping section of the device. Note that other detection methods are envisaged in the present invention and are discussed below.

In such an integrated photonics analysis subsystem, photonics sources, for example LED's or lasers, are combined with detectors, waveguides, couplers, and mirrors, to provide a fully-integrated optical detection system for detecting analytes in the present invention. The photonics components are preferably located upon, and attached to, the top surface of the main body of the B-FIT device in a top capping section.

Polymer waveguides with couplers for source and detector arrays are fabricated as integrated "flex circuits" for mounting. Fully integrated waveguide structures are fabricated by means known to those of skill in the art, such as monolithic fabrication of the waveguide by dry resist processes. –Low $\eta$ waveguide material ($\eta < \eta_{water}$ 1.33) is preferred.

Figure 9:
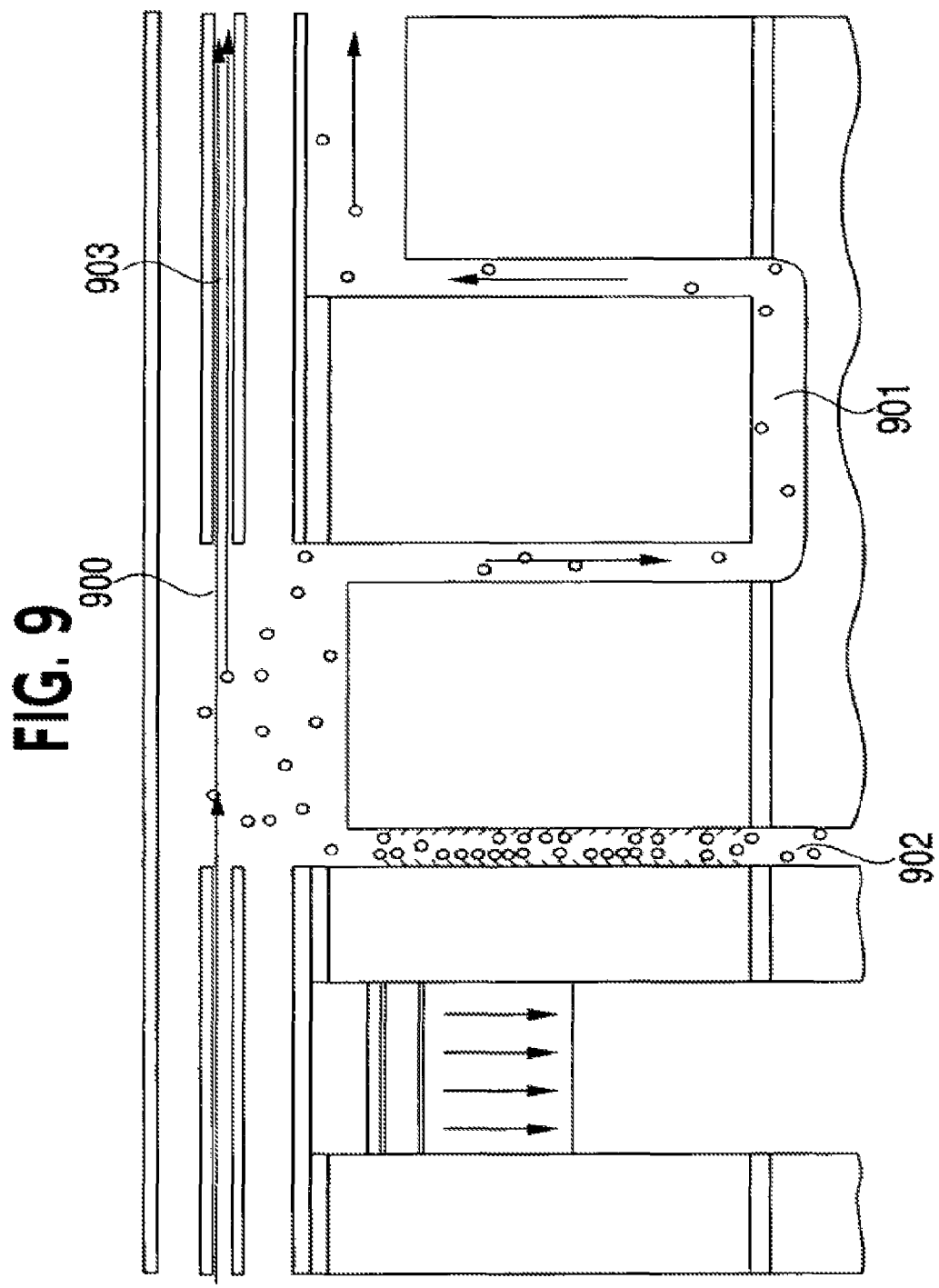
FIG. 9 illustrates in transverse section an alternative waveguide and sample chamber configuration.

FIG. 9 illustrates a preferred embodiment of a waveguide and sample chamber. In a preferred embodiment, capillary fluorescence is used to detect the analyte within the capillary. LED sources emitting green, blue, yellow, or red light, can be used to excite fluorophores. The choice of exciting wavelength is dictated primarily by the excitation spectrum of each fluorophore. In other embodiments, laser sources can be used to provide specific excitation wavelengths, although the cost, size, and power consumption of lasers is generally higher than for LED's.

In a preferred embodiment, the upper inner surface of the lateral portion of the serpentine capillary is completed by a surface of the top capping section 900. Optical detection is preferably performed within the lateral portion. Light is conducted to and from the lateral portion by an integral waveguide fabricated within the, preferably plastic, top capping section. The orientation of the waveguide runs parallel to the silicon surface.

In another embodiment, the transverse capillary interrupts the path of the waveguide 903, so that the light conducted by the waveguide passes directly through a portion of the solution contained in transverse capillary 900. This embodiment has the advantage of simplicity: lenses and mirrors are not required to divert and collate the lightbeam. Fluorescence or absorbance measurements are preferably made within the portion of the transverse conduit that interrupts the waveguide. A preceding conduit portion 902 preferably contains the binding reagents that give rise to the displacement into the solution of fluorophore when analyte is present. Subsequent conduit 901 preferably conducts the solution out of the light path.

In an alternative embodiment of the present invention, light measurements are made within a capillary that is constructed of a material having an index of refraction lower than that of water. This embodiment also eliminates the need for lenses and mirrors and offers superior signal to noise properties.

Figure 10:
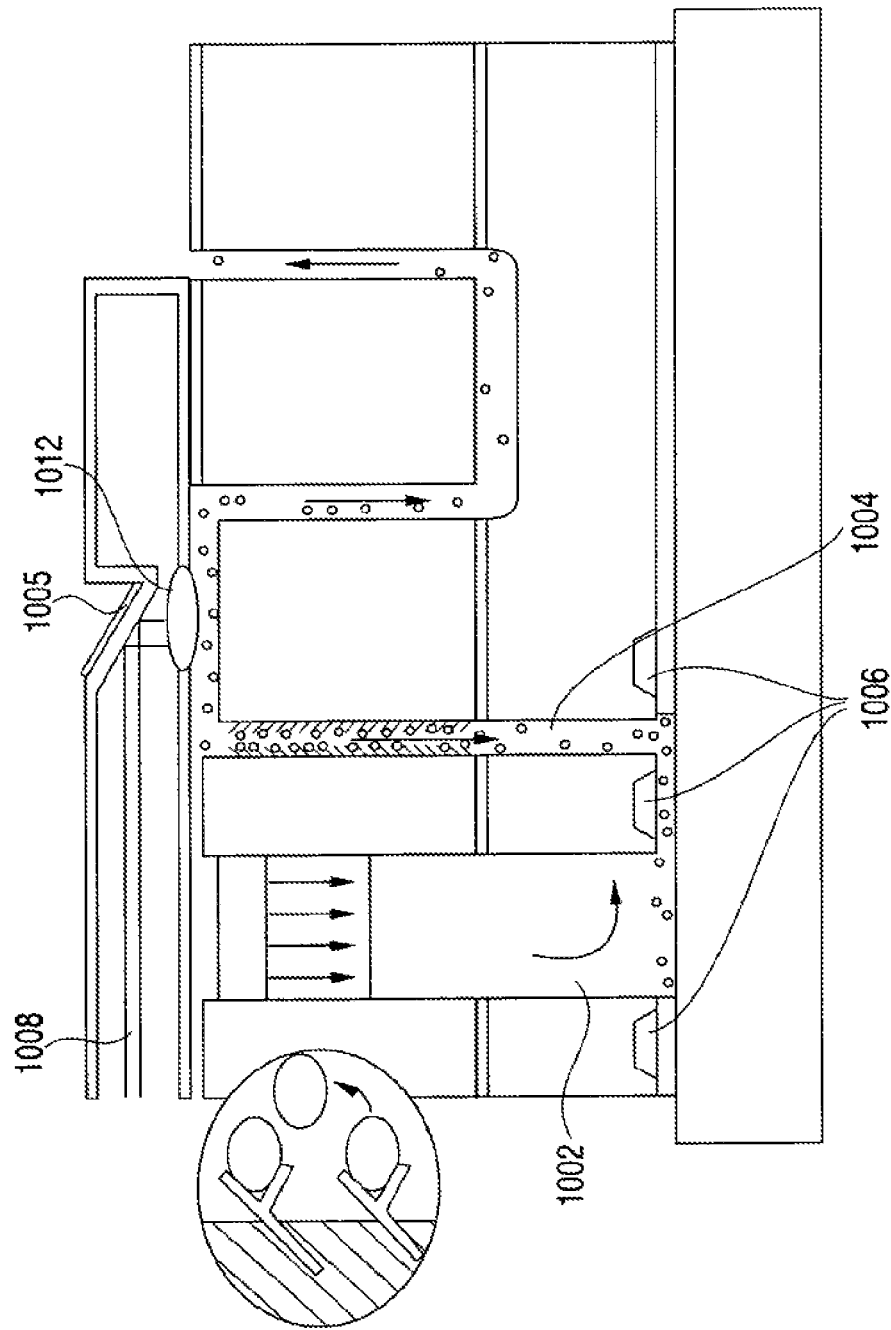
FIG. 10 illustrates a B-FIT microsystem.

FIG. 10 illustrates a preferred embodiment of the B-Fit system platform. To facilitate the coupling of light from the waveguide 1008 into the lateral portion, and from the lateral portion into the waveguide, a micro-mirror 1005 is preferably provided. The mirror is integrated as a pressed component in the top capping section, or is a separate component placed within the plastic housing by injection molding, or is fabricated by any other appropriate means. Preferably the micro-mirror 1005 is oriented at approximately 45° relative to the silicon surface of the lateral portion of the capillary, and is positioned directly above the lateral section. A highly reflective surface coating, such as a metal coating, is preferably deposited upon the surface of the mirror to reflect light from the horizontal waveguide downwards into the lateral portion of the capillary. A lens is preferably provided to collate the fluorescence excitation and emission light beams. Micro-lens 1012 is, in one embodiment, convex to provide divergence of the light beam entering the lateral section from the waveguide, and convergent with respect to light leaving the lateral portion and entering the waveguide 1008. In embodiments in which fluorescence detection is used, light from spectral region capable of exciting the fluorophore is conducted along the waveguide, strikes the divergent mirror and enters liquid contained within the lateral conduit. A fluorophore within the lateral conduit is preferably excited and emits light of a longer wavelength. The emitted light strikes the mirror, which converges the light, and re-enters the waveguide.

Bandpass or notch filters may preferably be interposed in the light path to optimize the signal-to-noise ratio of the detected fluorescence, depending on the bandwidth sensitivity of photodetector embodiment.

Light sources for the integrated photonics analysis subsystem include LED's, which have recently become available in light-emission colors from blue to green, thus essentially covering at least a portion of the excitation spectra of most commonly used fluorescent probes. See, for example, Fluorescent and Luminescent Probes for Biological Activity. A Practical Guide to Technology for Quantitative Real-Time Analysis, Second Ed. W. T. Mason, ed. Academic Press (1999). Alternatively, microelectronic lasers can preferably be used where specific wavelengths are required. Any light detection means can be used to detect the emitted fluorescent light. Photodiodes, phototransistors, Darlington pair phototransistors, or photoresistors can be fabricated onto the silicon surface of the main body, or can be provided as separate components.

Standard low power CMOS fabrication is preferably used to power the microsystem, to provide sequential logic control, and to permit storage of data in memory and its manipulation.

It should be noted that, despite the foregoing disclosure of fluorescence detection of analytes, the present invention is not restricted to fluorescence measurements. Other detection methods that are advantageously used in the present invention include, but are not limited to, Raman, UV-VIS, and FTIR spectroscopy, including two-dimensional techniques, and fluorescence correlation spectroscopy. Furthermore, radiation sensors and magnetic field sensors are also useful as the basis of detection in certain embodiments. For monitoring radiation workers and the like, a preferred sensor embodiment is an optical random access memory (ORAM) material. These materials are composed of a photochromic molecule such as spirobenzopyram embedded in a poly(methyl methacrylate) matrix. The measurement approach is based upon measurement of radiation-induced tracks in optical memory media.

An optical deflection magnetic field sensor is preferably utilized where magnetic field monitoring is desired. The microsensor comprises an aluminum beam that is suspended above a micromachined silicon substrate using four aluminum support arms. These arms hold the beam at its nodal points, which are points of zero displacement when the beam vibrates at the fundamental resonant frequency. A sinusoidal current is forced to flow through one support arm, through the length of the beam, and out through the other support arm. The frequency of the sinusoidal current is essentially identical to that of the mechanical resonant frequency of the beam. In the absence of a magnetic field, the beam is unaffected. However, in the presence of a magnetic field oriented perpendicular to the beam, a magnetic force causes deflection of carriers, which in turn causes the beam to vibrate at its resonant frequency. The amplitude of the vibration is directly proportional to the magnetic field strength, which can be measured using a laser.

FIG. 10 illustrates the operation of an embodiment of the B-FIT system with respect to analyte detection. The physiological solution preferably contacts the exposed viable epidermis following operation of microheaters 1006 to ablate a portion of the stratum corneum, rupture the seal, and expel the physiological solution from the reservoir channel 1002. Solution containing analyte recovered from the interstitial fluid bathing the viable epidermis preferably enters the capillary channel 1004. Within the capillary channel, analyte displaces fluorescently labeled analyte from analyte binding molecules affixed to the capillary walls. Displaced fluorescently labeled analyte is preferably carried to the lateral portion where it is excited by light conducted by the waveguide 1008, micro-mirror 1005, and micro-lens 1012. Light of a longer wavelength that is emitted by the fluorophore is, in one preferred embodiment, conducted back into the waveguide 1008 by the reversed optical pathway, and propagates to a detector.

The integration aspect of the present invention also preferably includes the aspect that real-time monitoring of a subject permits the use of adaptive control algorithms to optimize the conditions (for example, heating pulse characteristics, sampling rate, among others), and drug delivery regimen, in response to data obtained. In this preferred embodiment of the invention, data machine-learning techniques are preferably employed to derive or learn some function that relates one measure of the health of a subject to analyte measurements, thereby possibly acquiring the ability to predict the health measure from subsequent analyte measurements. Adaptive control algorithms utilized in the present invention embody the steps of learning, adaptation, feedback, and decision-making. Since the body is a dynamic system, these steps occur simultaneously and continuously throughout the life of the device of the present invention.

Figure 12:
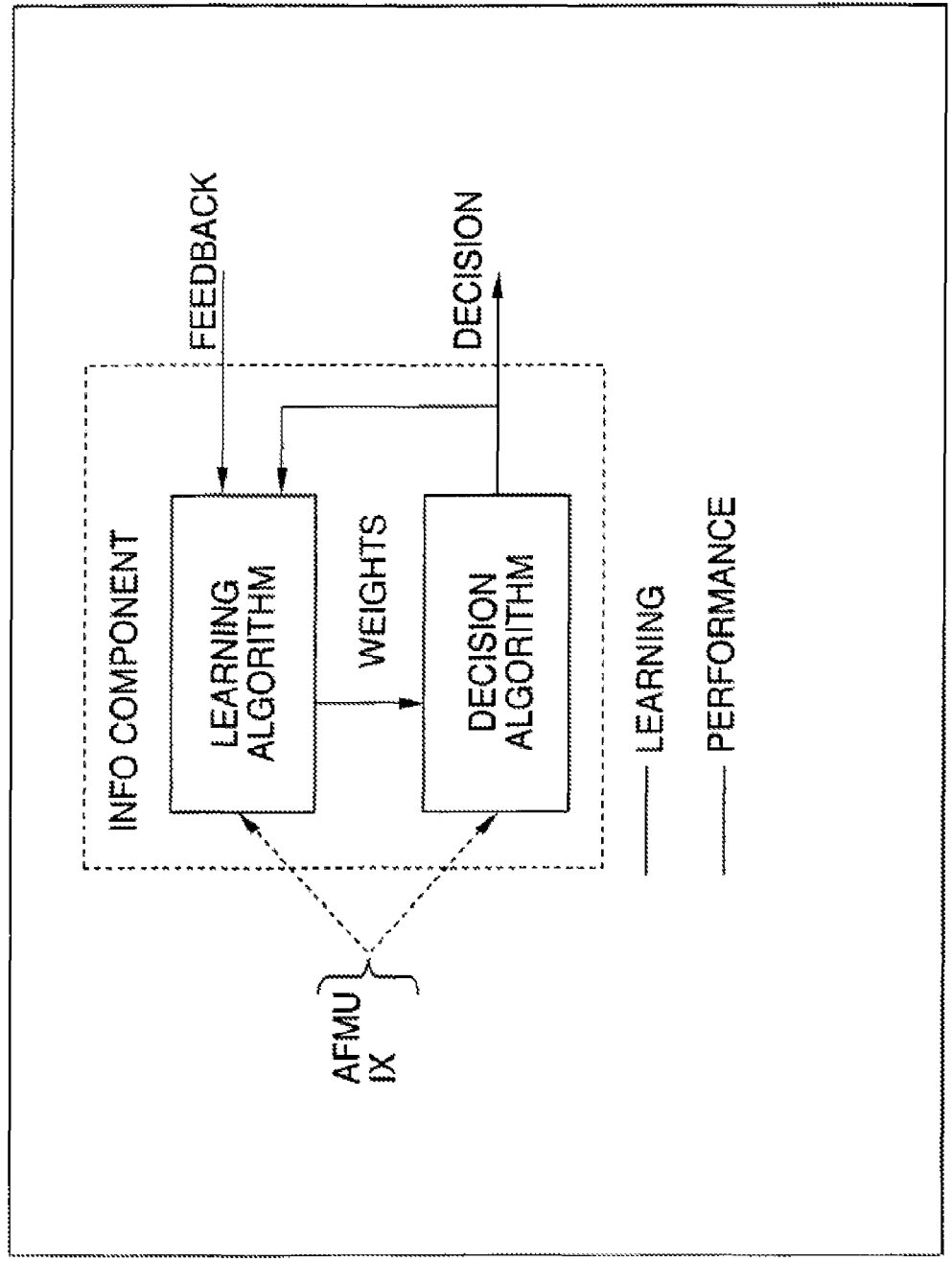
FIG. 12 illustrates an overview of the ELISA microsystem informational component.

FIG. 12 illustrates an overview of the ELISA microsystem informational component. A preferred aspect of the present invention is the large number of individual measurements that are possible over an extended time period. With extended periods of measurement, baseline drift must be accounted for so that significant deviations are accurately detected. The present invention preferably provides computational means for accounting for baseline drift, and for thereby detecting deviations from a current baseline. This means is illustrated for an embodiment directed to monitoring health in a subject. With improved monitoring techniques, day-to-day variations in metabolism are preferably established in the healthy individual, and limits set to detect early stages of infection, disease progression, and exposure to toxins.

The metabolism of exogenous compounds such as drugs is mediated by a series of enzymes. The type and amount of these enzymes in each individual is reflected in the person's genotype and, based upon the genetic information, individuals can be classified as more efficient metabolizers (FAST) and others as less efficient metabolizers (SLOW). In healthy individuals, the relationship between genetic makeup (genotype) and its expression (phenotype) is conserved, i.e. FAST genotypes produce FAST phenotypes, while SLOW genotypes produce SLOW phenotypes. However, a disease state of the individual can alter this relationship, as can diet, smoking, alcohol, environmental chemicals, and biological or chemical warfare agents, among other factors. The determination of a person's NAT-2 genotype and the monitoring of that individual's NAT-2 phenotype can be used as a direct and sensitive probe of heath and clinical status.

In this approach, polyclonal antibodies are preferably developed against the caffeine metabolites AFMU and IX, and are used to determine NAT-2 phenotypes in an embodiment of the present invention. Blood glucose levels, cytokine levels, and dextromethorphan metabolite levels, can also be monitored.

Machine-learning algorithms are preferably used to acquire a metabolic baseline and to indicate when an individual's body begins to enter a state of distress or disease. The Winnow and Weighted-Majority Algorithms (Littlestone & Warmuth, Information and Computations 108, 212, (1994) can preferably be used. These algorithms, with well-understood formal properties, are capable of learning and performing in non-stationary environments (i.e., in the presence of baseline drift).

The readings of the two caffeine metabolites, AFMU and 1X, are preferably provided as inputs for computation, and the computation preferably proceeds in two alternating and cooperative modes: a learning mode and a performance mode. In the learning mode, the device preferably continually calibrates itself to the wearer's body chemistry using an adaptive algorithm, which adjusts a set of weights, with the aid of feedback. User interaction is necessary only if the body is stimulated in such a way that the levels of the metabolites are not indicative of normal body function (i.e., the user will provide feedback only for false-negatives). In the performance mode, the device preferably takes the readings of the caffeine metabolites and, using the current concept descriptions (i.e., weights), makes a decision about the body's state of health, which is then communicated to the user. Since the body is a dynamic system, this process of learning, adaptation, feedback, and decision-making preferably occurs continuously and throughout the life of the device.

The device also preferably acquires a model of the wearer's healthy state, and uses this model to predict states of health in the future. Formally, machine-learning methods derive or learn some function fn from a set of x, y pairs, such that $y=f(x)$. Naturally, $f()$ is an approximation to the true function, which is unknown.

However, when levels of, say, troponin I begin to increase (suggesting an imminent heart attack), then the device will preferably need to sample more frequently, as the rate of change from one measurement to the next will be increasing. In this situation, adaptive control algorithms are preferably employed, powerful enough to properly control the sampling rate, but simple enough to be realized in micro-hardware.

Thus, in a preferred embodiment, adaptive control algorithms can be used to task the transdermal component to sample its wearer for the target substances, and machine-learning algorithms can be used to acquire a model, which may change, of the wearer's healthy state.

Referring back, FIG. 10 illustrates a preferred embodiment of a B-FIT micro system. This total modular system preferably includes: (1) the fluid transport system including reservoir channel 1002, and capillary channel 1004; (2) micro-heater(s) 1006, (3) the photonics system including waveguide 1008, micro-mirror 1005, and micro-lens 1012, and (4) the chemistry for analysis of selected analytes. The interstitial fluid containing molecules indicative of biomarkers are preferably obtained using a minimally invasive technique employing controlled thermal micro-ablation of the stratum corneum. The micro-heater(s) 1006 used for this are preferably incorporated directly into the silicon-based subsystem that is part of the B-FIT microsystem. For optimal transport of interstitial fluids or analytes through the analysis capillary, a second reservoir capillary, containing a physiologically compatible fluid, is preferably used to drive all fluids towards the upper surface of the module. The driving force is preferably provided by microheater(s) 1006 that produce bubbles to force the liquid to flow out of the reservoir capillary and over the thermally ablated region of the skin. Once the interstitial and physiological appropriate liquids containing tagged and untagged molecules reach the top holding-cavity, analysis can begin. The top of this total transdermal detection platform can preferably be integrated with optical waveguides, comprising micro-mirror(s) 1005 and micro-lenses 1012 for properly directing the light within the holding-chamber. The light that strikes the analysis region of the holding-cavity is used to excite the fluorescently tagged molecules. The intensity of this fluorescence is preferably picked up through the return path by the same optical waveguide.

The modular nature of the microsystem provides an excellent platform that can be easily adapted for many innovative applications by applying new chemistries for the detection of selected analytes. For example, one analyte or biomarker that is especially important to children exposed to pesticides is acetylcholine. Acetylcholine is located throughout the body and when it is released, it acts as an excitatory neurotransmitter to propagate nerve conduction in the peripheral and central nervous systems, or to initiate muscle contraction. Exposure to organophosphorus pesticides causes inhibition of acetylcholinesterase activity resulting in an accumulation of acetylcholine. This increase in acetylcholine concentration will act as a biomarker, measured using the device by first establishing a baseline in an unexposed child. The MEMS-based patch is small and unobtrusive, permitting a child to live his/her daily life while being continuously monitored for exposure to pesticide contamination and providing early warning diagnostics.

Thus, one embodiment of the portable biomedical monitoring device of the present invention is as a pediatric micro patch system (PµP). In providing such a Pµl) device there are three tasks. Task 1 is the fabrication of silicon bed structures that function analogous to the B-FIT Microsystem. As described above, the bed functions to deliver fluids to the interior of the capillaries and to the collection chamber. In addition, the bed mirrors the B-FIT microsystem with regard to the integration of the chemistry. Task 2 is the chemistry to detect acetylcholine. This task includes chemically modifying a flat sample of silicon, which enables a functioning method for integrating chemistry to the bed. Task 3 involves the testing and validation phase, where the chemistry protocol is adopted for the capillary bed. Detection limits of acetylcholine are established and sample bodily interstitial fluid is tested.

With regard to the B-FIT system, the fabrication of the capillary bed structures relies, in one embodiment, on bulk micromachining of silicon, accomplished through either deep reactive ion etching (DRIE) or wet chemical etching. The DRIE process preferably enables the fabrication of high aspect ratio through-wafer holes that form narrow micro-capillaries of varying diameters. Wafers with a nominal thickness of 500 µm are used; however, a preferred thickness can be established through surface modification testing.

For the exemplary bed structure shown in FIG. 10, (type C), an array of capillaries with varying diameters are preferably formed using lithographic patterning and DRIE. This type of structure enables selection for the optimal dimensions required for capillary action to allow liquids to be drawn up and inside the channel, because wet chemistries are involved in both capillary-wall surface modifications and during fluorescence validation using a test solution containing acetylcholine. Once the capillaries have been chemically modified, testing for fluorescence is preferably accomplished using a laser source at the top-side entrance port of the silicon capillary, and a detector located at the exit port on the bottom-side.

Figure 11:
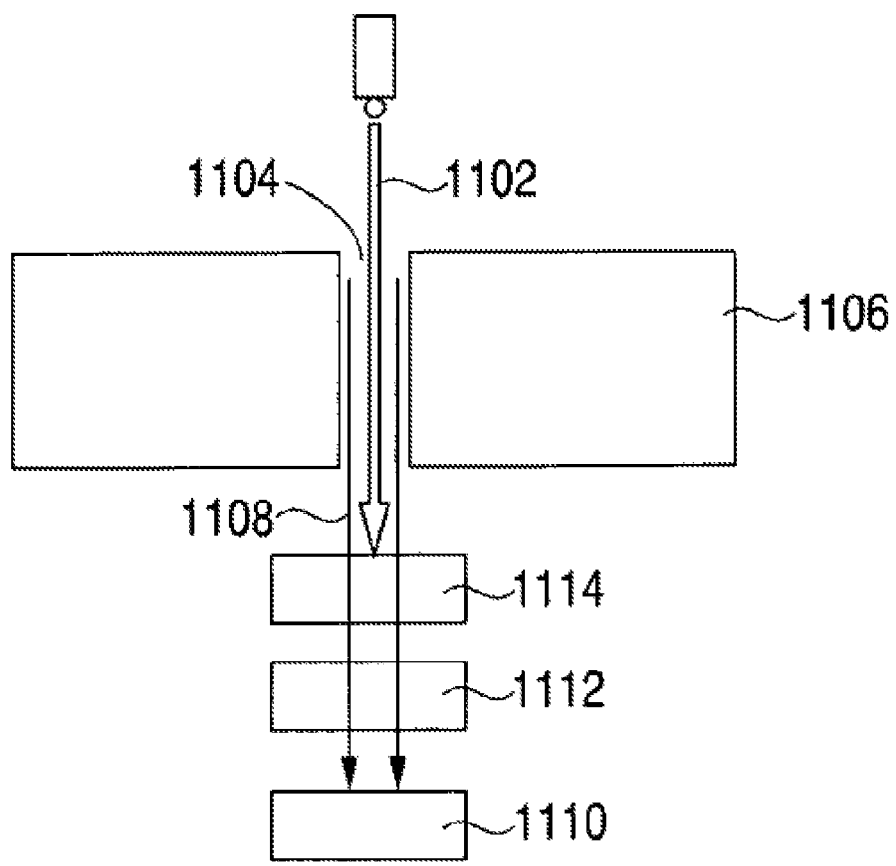
FIG. 11 illustrates a cross-sectional view of type C bed illustrating the detection scheme.

Returning to FIG. 11 illustrating this preferred detection scheme, the spot size of the laser light path 1102 can preferably be adjusted to match the diameter of silicon capillary hole 1104 etched in silicon substrate 1106, while its excitation wavelength is preferably held at 430 run, to match the frequency required to excite the fluorophore causing it to emit fluorescent light 1108. The detector preferably includes photomultiplier 1110, and monochromator 1112 is preferably used to tune the detector to the fluorescence wavelength of 567 nm. In addition, notch filter 1114 is preferably used to greatly attenuate the unwanted laser light frequency from reaching the photomultiplier.

A second exemplary bed structure, termed type CI, is similar to the basic capillary array with a modification to the entrance port that is fitted with a microfluidic interconnect. This design is preferably used as an alternative to type C, in a situation where capillary action perhaps does not function appropriately. In such circumstances, type CI provides an interconnect mechanism allowing for external tubing or syringe ports to be directly coupled to the silicon capillary for surface modification and testing purposes.

Figure 13:
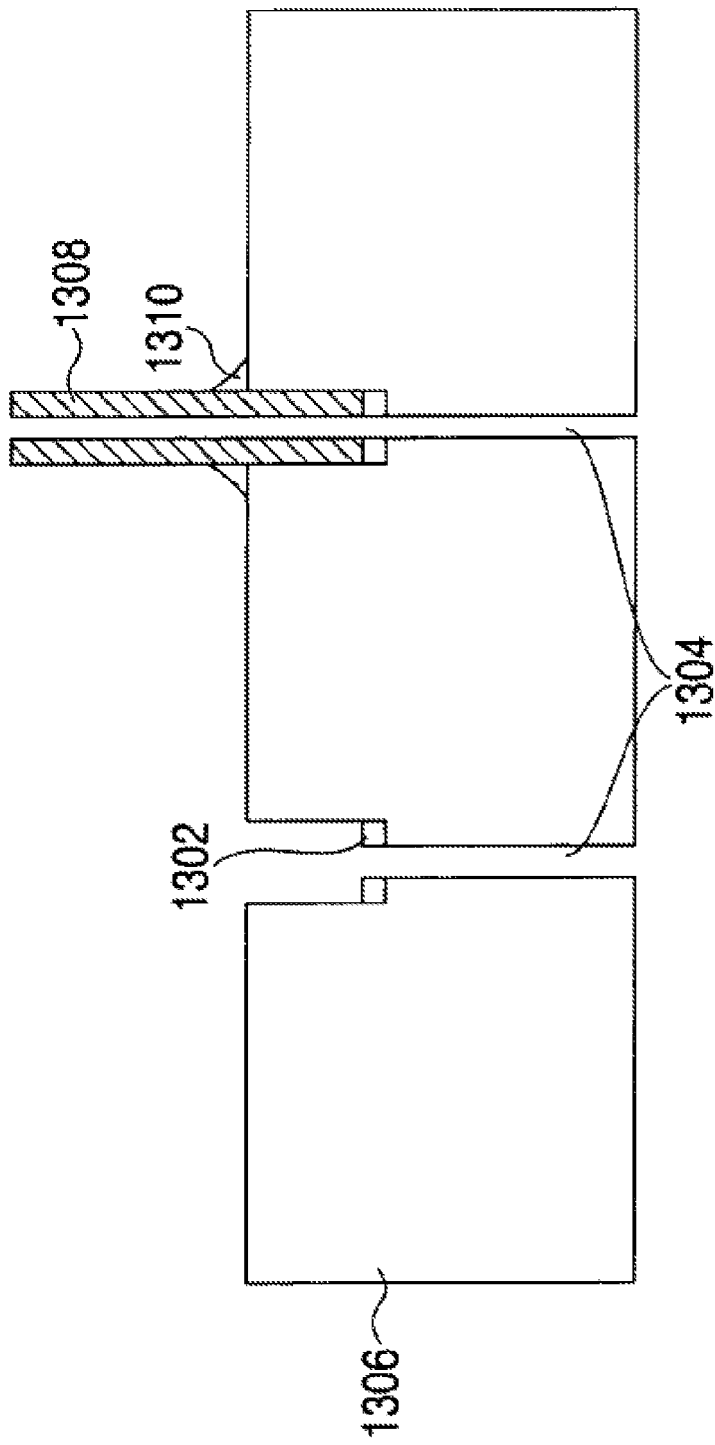
FIG. 13 illustrates a cross-sectional view of type CI showing the microfluidic interconnect, coupling the external tubing with the silicon capillary.

FIG. 13 illustrates a cross-sectional view of a type CI bed structure showing the microfluidic interconnect, coupling the external tubing with the silicon capillary. Typically, a hole produced by DRIE can preferably be made so that its inner and outer diameters match that of the interconnect tubing, which is inserted into the opening and held in place with adhesive 1302. Thus, DRIE microcapillaries fabricated as wafer through holes 1304 are in silicon substrate 1306. The holes are preferably produced such that the inner and outer diameters match that of external tubing connected to silicon capillary 1308, wherein the tubing is held in place with adhesive 1310. However, care must be taken such that the adhesive used to hold the tubing does not seep into the capillaries blocking the flow.

Figure 14:
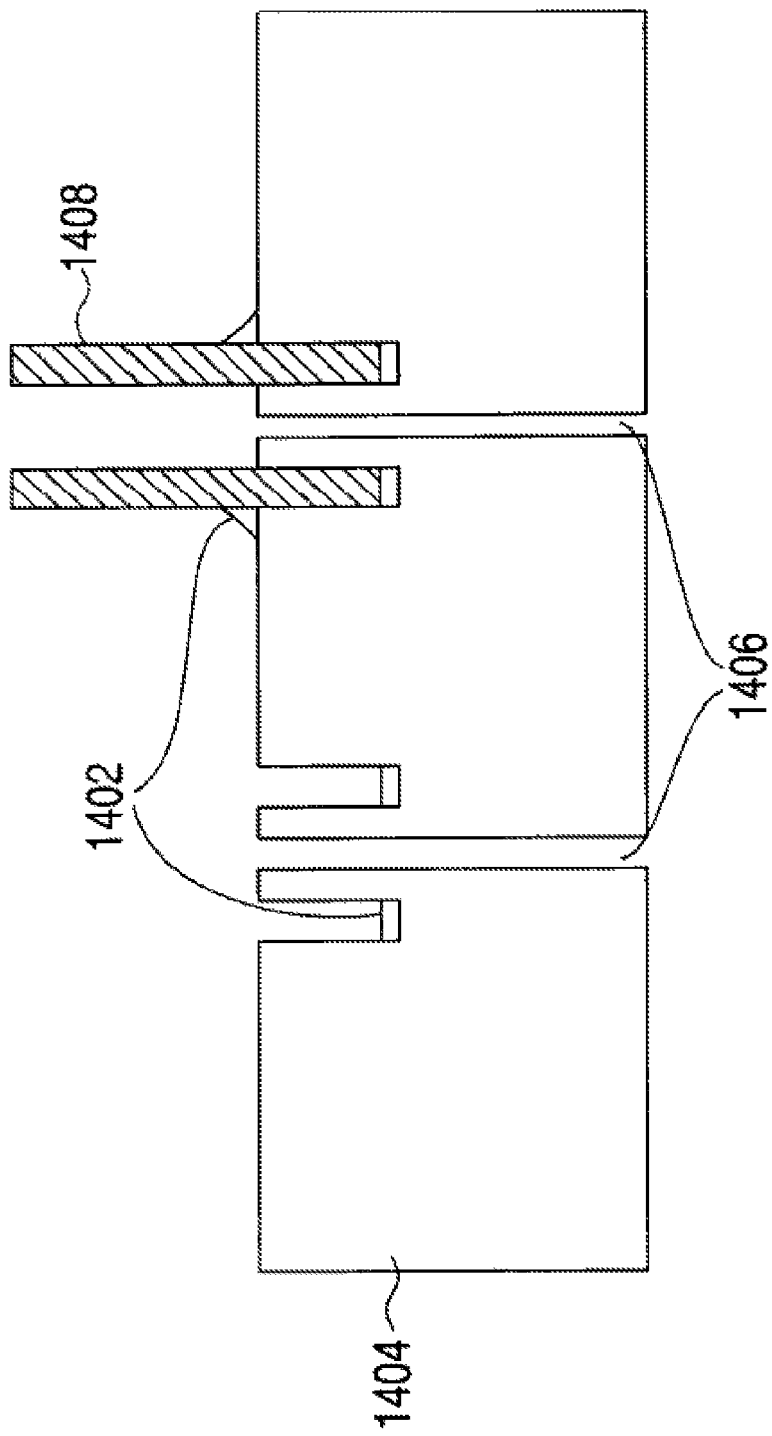
FIG. 14 illustrates a cross-sectional view of an alternative which uses a silicon sleeve around the DRIE capillary hole, showing the silicon sleeve microfluidic interconnect, coupling the external tubing with the silicon capillary fabricated as wafer through-holes, and external tubing connected to silicon capillary.

FIG. 14 illustrates a cross-sectional view of an alternative embodiment which uses a silicon sleeve around the DRIE capillary hole, showing the silicon sleeve microfluidic interconnect, coupling the external tubing with the silicon capillary. The sleeve preferably provides enhanced mechanical integrity for the external fluidic component, but also prevents adhesive 1402 from seeping and plugging the capillary hole. Once the external tubing is attached to the silicon substrate, chemicals and analytes can preferably be injected using either pressure gradients or syringes. The external tubing is then removed, having fulfilled its purpose of introducing fluids into the narrow capillary channel, and the verification procedure to detect fluorescence can start, as for the type C device. FIG. 14 thus shows adhesive 1402, silicon substrate 1404, DRIE microcapillaries fabricated as wafer through-holes 1406, and external tubing connected to silicon capillary 1408.

Figure 15:
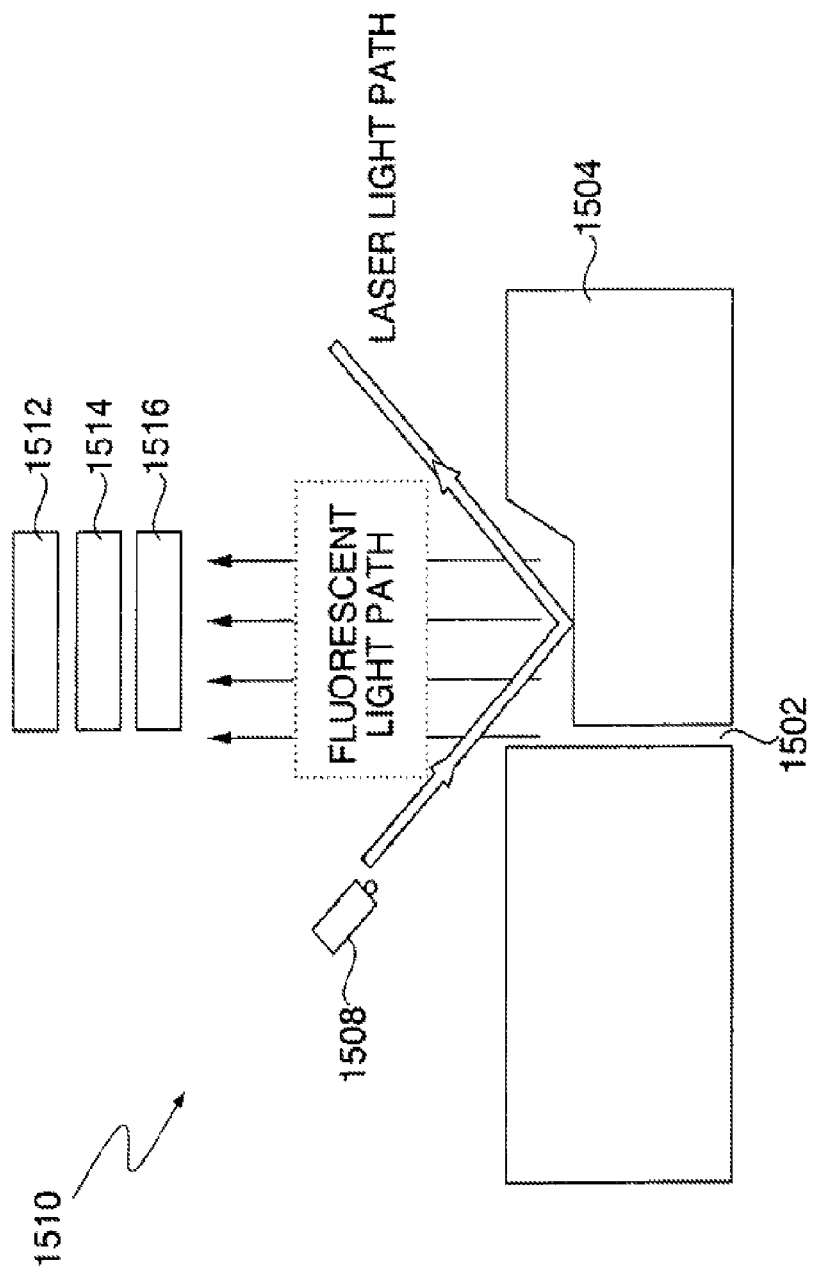
FIG. 15 illustrates a cross-section view of a third bed structure incorporating a collection chamber for the analyte, which has flowed up through DRIE capillary through-wafer hole by capillary action.

FIG. 15 illustrates a cross-sectional view of a third bed structure incorporating a collection chamber for the analyte, which has flowed up through DRIE capillary through-wafer hole 1502 by capillary action. For this microstructure, called type CC, the silicon capillary is preferably fabricated using DRIE followed by an anisotropic wet silicon etch to create the collection chamber on the front-side of silicon substrate 1504. With this bed, it is sufficient to chemically modify only the surface of this chamber. The analyte preferably flows up the capillary channel and reacts with the immobilized chemistry in the chamber to produce fluorescence light path 1506.

FIG. 15 also illustrates preferred excitation laser 1508 and fluorescence light path 1510 detection set-up. The excitation and detection method preferably makes use of excitation laser 1508, photomultiplier 1512, and monochrometer 1514, respectively, as before, however, now the setup is preferably only on the front-side of the bed structure. The photomultiplier 1512 and monochrometer 1514 are preferably set directly above the collection reservoir to act as the fluorescence detector. In this situation, the impinging laser light can preferably be directed towards the collection chamber at an angle such that its reflection does not contribute to photomultiplier 1512 detection. Nevertheless, notch-filter 1516 can preferably be used between the detection unit and the chamber to eliminate any stray light from excitation laser 1508.

Figure 16:
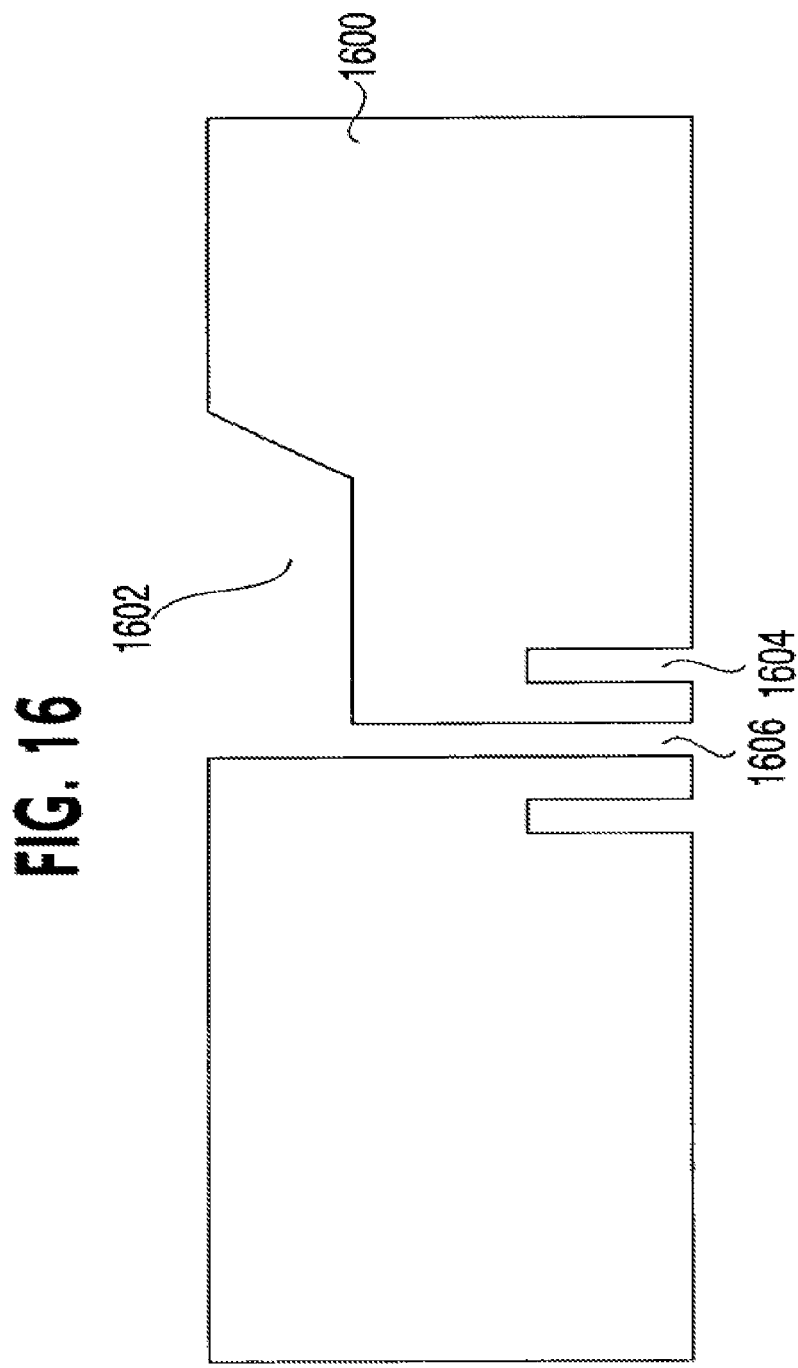
FIG. 16 illustrates a cross-sectional view of a fourth bed, designated type CIC, incorporating collection chamber and fluidic interconnect.
Figure 17:
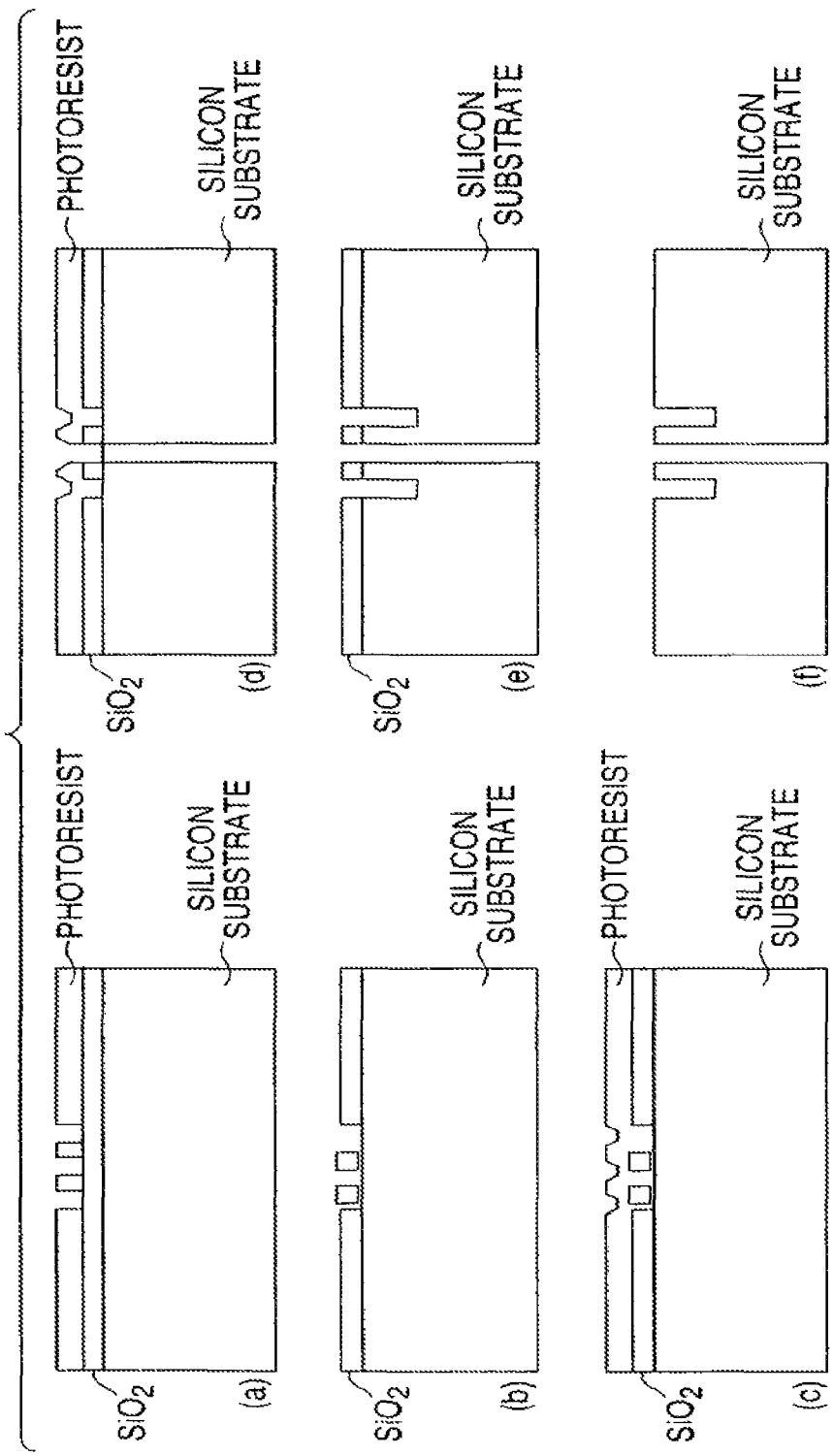
FIG. 17 illustrates the general fabrication process for the type CI array, showing, (a) photoresist (PR) patterning for silicon sleeve, (b) oxide patterning of sleeve, (c) re-application of PR, (d) pattern for DRIE of bore hole, (e) remove PR and DRIE sleeve, and (f) remove oxide.

FIG. 16 illustrates a cross-sectional view of a fourth preferred bed, designated type CIC, incorporating collection chamber 1602 and fluidic interconnect. In addition to the silicon capillary channel and collection chamber of type CC, this bed preferably also includes a fluidic interconnect mechanism on the back-side of the wafer. As before, this design can preferably serve as a fallback mechanism if the capillary action does not provide enough capillary force to draw the fluid up to the collection chamber. The fluidic interconnect preferably makes use of the silicon sleeve 1604, as described in the type CI test-bed structure. DRIE capillary through-wafer hole 1606 and silicon substrate 1606 are also shown.

For each variation in bed structure, fabrication of the through-wafer capillary arrays is made on single-sided polished, <100>-type 4 inch silicon wafers. The array of capillary holes preferably consists of four diameter values (25 µm, 50 µm, 75 µm, and 100 µm) with a nominal length of 500 µm, which corresponds to the wafer thickness. For the type C design, the patterns for the holes are preferably formed in a photoresist layer, which acts as an ideal masking layer to the DRIE process. A single (standard) photolithographic step preferably produces patterns on the front-side of the polished silicon surface. Although the DRIE process renders an anisotropically etched cavity, some undercutting of the mask takes place. Thus, the pattern of the mask takes into account this unavoidable lateral etch to achieve the desired diameters for the capillaries. Depending on the type of DRIE system used, the ratio of vertical-to-lateral etch is better than 50-to-1. That is, for every 50 µm of etch depth, there is approximately 1 µm of under-etch beneath the masking layer. The masking dimensions are therefore dependent on this etch parameter, which can be determined through prior testing. DRIE services can be obtained, for example, through one of the National Nanofabrication Facilities, or through the MEMS Exchange program.

FIGS. 17(a) to (f) illustrate a preferred general fabrication process for the type CI array, showing, (a) photoresist (PR) patterning for silicon sleeve, (b) oxide patterning of sleeve, (c) re-application of PR, (d) pattern for DRIE of bore hole, (e) remove PR and DRIE sleeve, and (f) remove oxide. The initial step, prior to lithography, is to grow a thin layer of thermal silicon dioxide over the entire silicon surface. Photoresist is applied, and the oxide is patterned and etched to delineate the locations of the silicon sleeves that are located around each capillary hole providing for microfluidic interconnections. This step is followed by another application of photoresist, and the capillary locations are patterned into both photoresist and oxide. Through-wafer holes are again formed using DRIE, as with the type C device. The photoresist is subsequently removed, leaving the pre-patterned layer of thermal oxide on the front-side of the silicon surface. A much shorter DRIE step is performed, with the oxide layer acting as the masking layer, to create the silicon sleeve.

For both type CC and CIC the fabrication process preferably requires the wafers to be double-sided polished since back to front alignment is required. For the type CC device, the collection chamber is preferably bulk micromachined into the front-side of the wafer using an anisotropic wet chemical etchant. Subsequently, a thin thermal oxide is grown only on the front-side to act as a passivation layer, while the back-side is coated with photoresist. The DRIE procedure for the capillaries is performed from the back-side so the capillary hole aligns with one side of the collection chamber.

Figure 18:
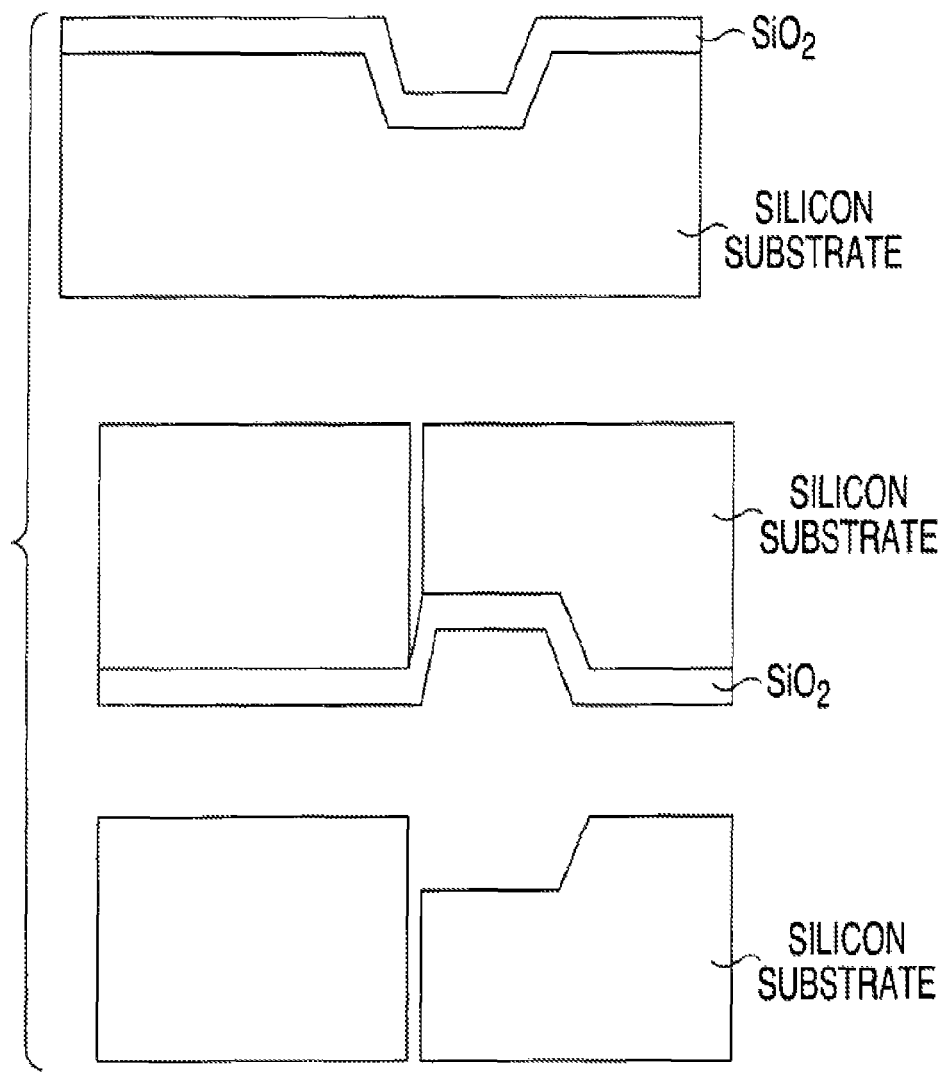
FIG. 18 illustrates a cross-section showing the double sided processing necessary to fabricate the type CC (and type CIC) device.

FIG. 18 illustrates a cross-section showing the double sided processing necessary to fabricate the type CC (and type CIC) device. The wafer is then inverted so that subsequent processing of the capillaries and silicon sleeve interconnects on the back-side follows the same procedure as that for the type CI device.

With regard to a preferred surface modification aspect of the present invention, the technical approach to providing a surface bound fluorescent probe specific for the biomarker acetylcholine is preferably accomplished by modifying the method developed for liquid phase detection set forth in Inouye, M. et al., Nondestructive Detection of Acetyl Choline in Protic Media: Artificial Signaling Acetylcholine Receptors, J. Am. Chem. Soc., 116, 5517 (1994). In a preferred embodiment, the method utilizes spiropyrans, which are inexpensive and readily available from commercial sources. They are known for their spectral properties and are very robust, especially compared with molecules used for standard ELISA detection methods. The spiropyrans are synthetically surface immobilized on the silicon bed, in either a collection chamber or in a capillary, using silane chemistry and standard coupling chemistry.

Figure 19:
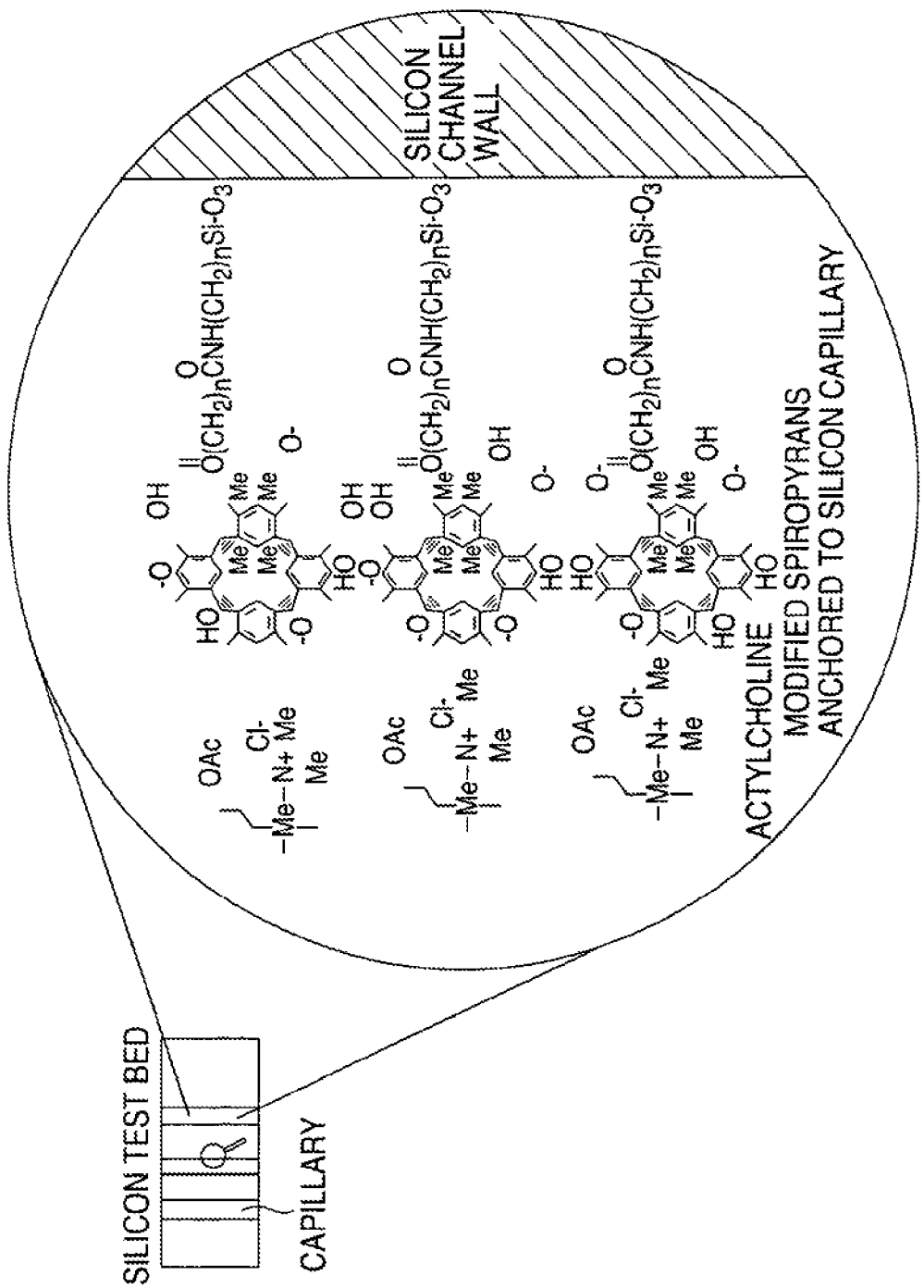
FIG. 19 illustrates a magnified view of anchored spiropyrans in a silicon capillary.

FIG. 19 illustrates a magnified view of anchored spiropyrans in a silicon capillary. A spiropyran (for example, C-methylcalix[4]resorcinarene) is preferably modified to incorporate a carboxylic acid cross-linking group that can be coupled to a free amino-silane modified silicon surface. Stoichiometric addition of base to the spiropyran allows for the reaction of an co-bromocarboxylic acid (for example, 5-bromopentanoic acid). The length of this molecule is related to its solubility and reaction efficiency. Longer carbon chain-lengths are more soluble, but harder to couple to the surface, while longer carbon chain-lengths are less soluble and more likely to couple to the surface. The synthesis can be followed by NMR spectroscopy as needed to examine and characterize reaction products.

The spiropyran or resorcinol/acetaldehyde tetramer preferably forms a tetraphenolate in akaline media that arranges in a bowl shaped cavity and can complex alkylammonium cations. When complexed with a pyrene modified N-alkyl pyridinium cation (PPC), no fluorescence is observed. The PPC may be purchased or synthesized depending on the selected method. One preferred method of incorporation of PPC is by solution complexation with the spiropyran. After anchoring the spiropyran, PPC is introduced and the complex is formed. The competitive binding of acetylcholine kicks off PPC and produces a fluorescent complex. This complex is detected using the laser/detector scheme described above in the microfabrication approach. PPC can also be incorporated by forming mixed mono layers of the spiropyran and the PPC. In this way, complexes are formed at the solution surface interface. Another preferred way of making PPC complex with the spiropyran is by synthetically attaching PPC to the spiropyran as describe by Inouye, et al., supra. This method allows for intramolecular quenching of the fluorescence as opposed to intermolecular quenching as described in the first two methods.

Upon completion of synthesis, silicon substrates are preferably derivatized with silanes such as 3-aminopropyltrimethoxysilane. The reaction provides a free amino group on the silicon surface that can be coupled using a water-soluble carbodimide, such as EDC, to the carboxylic acid of the modified spiropyran. X-ray photoelectron spectroscopy (XPS) and contact angle measurements can be employed to analyze the progress of varying surface attachment reactions. In a preferred embodiment, the highest surface coverage is achieved. In addition to surface coverage, the fluorescence efficiencies is examined using a fluorescence microscope. This aids in qualifying the activity of the attached spiropyrans. A simple experiment monitoring the qualitative fluorescence intensity before addition of acetylcholine and after the addition of acetylcholine provides a baseline. At this point, the method is transitioned into bed devices for testing.

During the microfabrication task, DRIE and wet chemical etch rates are preferably determined using test samples in order to produce the proper bed structures. In addition, preferably samples are cleaved and viewed through a scanning electron microscope to determine whether the proper cross-sectional geometry of the through-wafer capillaries has been achieved. For the chemistry task, surface modification and chemical synthesis is preferably used to validate the immobilization protocol on a flat sample of silicon. This determination requires the detection of fluorescence after excitation on a relatively large sample; thus, a fluorescence microscope is used during this testing procedure.

Once the chemical synthesis and surface modification tasks are completed through rigorous large sample testing, the chemistry is then tested on the small-scale capillary bed structures. For this phase, a photonics-based test set-up is preferably employed based on the excitation and emission of fluorophores. Excitation is through direct absorption from an external laser source. Several preferred sources are available for various testing strategies, including tunable continuous wave (CW) argon ion pumped dye laser, an air-cooled argon ion laser, a Nd:YAG nanosecond pulsed laser which pumps an optical parametric oscillator, and several smaller HeNe lasers with both red (632.8 nm) and green (543 nm) wavelength outputs. The Ar ion pumped dye laser has outputs from the pump laser at wavelengths of 488 nm and 514 nm, with a maximum power of 9 W. The maximum power from the CW dye laser is 3 W, and is tunable in the ranges of 590 nm to 600 nm and 610 nm to 630 nm, with an additional output at 577 nm. The air-cooled Ar ion laser has a single output at 514 nm and provides approximately 70 mW of power. The Nd:YAG laser has a fundamental wavelength of 1064 nm, along with the doubled (532 nm) and tripled (3.55 nm) outputs achieved with internal harmonic generators (KDP crystals). The pulse width is 5 to 7 nanoseconds, with peak pulse powers of over 200 mJ. However, since the fluorophore being immobilized on the silicon surface needs to be excited at 430 nm, the power from the tripled output Nd:YAG laser can be used to pump an optical parametric oscillator (OPO), based on a beta Barium borate crystal (BBO). This is essentially a resonant optical cavity containing the nonlinear BBO crystal. The pump beam is converted to the so-called signal and idler beams, where the wavelengths following the relation:

$$\frac{1}{\lambda} \text{pump} = \frac{1}{\lambda} \text{idler} + \frac{1}{\lambda} \text{signal}$$

which arises from the photon energy conservation requirement. The ratio between the two output wavelengths is governed by the angle of the BBO crystal with respect to the incident beam. Using this, the output wavelength can be tuned by changing the crystal angle. Either the signal or idler output can be eliminated using a high- or low-pass optical filter at the output port of the OPO. This output is tunable in different ranges from about 400 nm to 2200 nm. The ranges are set by the resonant cavity mirror properties and the output filters. Peak pulse energies in these ranges are on the order of 10 mJ.

The output fluorescence is preferably detected either in the forward direction or at some angle depending on the microstructure geometry. In either case, the incident laser light is preferably blocked using both a holographic notch filter and a monochromator. The notch filter, commonly used in Raman spectrometers, cuts all light at the wavelength of the excitation light, whether coming directly from the laser or from Rayleigh scattering. The monochromator provides further rejection of unwanted light, both ambient and from the laser. The monochromator also allows tuning to the maximum of the emission spectrum, for optimization of the signal-to-noise ratio. Finally, detection is preferably accomplished using a photomultiplier and a boxcar-integrator detection scheme, with gating from the laser electronics. Alternately, the signal is detected with a silicon avalanche photodiode, providing higher detection efficiency.

With the type C bed, capillary action is preferably tested in order to, first, modify the internal silicon surface wall of the capillary hole, and then, second, to draw up analyte, which reacts with the immobilized sidewall chemistry. If the capillary forces are not sufficient to draw up significant amounts of fluid for the capillary dimensions being tested, then the type CI test-bed is preferably used. This allows direct physical insertion of fluids within the capillary using a pressure gradient or a syringe pump connected to the microfluidic interconnects. In either case, the photonic detection system is preferably used to test the feasibility of performing in-capillary fluorescence measurements. In contrast, the type CC test-bed requires chemical modification only within the silicon surface of the collection chamber. Therefore, this device can also be used to test capillary action as well as the photonic detection system situated on the front-side of the wafer. Again, the device can preferably be tested physically by inserting the analyte into the capillary array, using bed type CIC.

Once a particular bed is selected, further testing preferably relates to determining the selectivity and sensitivity of the biomarker to the immobilized chemistry within the capillary array. This type of testing is preferably conducted, for example, by introducing a solution containing acetylcholine at varying concentration levels. By determining the amount of fluorescence variation, using the output from the photomultiplier, with corresponding changes in acetylcholine concentration levels, a quantitative indication of the lower limit of detection of acetylcholine, and therefore device sensitivity, is obtained. To determine selectivity, another series of tests are preferably performed to introduce other neurotransmitters in various concentrations within the analyte solution and to determine their relative fluorescence with respect to that obtained for acetylcholine. The more common neurotransmitters that can be used in this testing phase, other than acetylcholine, include adrenaline, dopamine, serotonin, tryptamine, histamine, and glycine. For comprehensive testing of selectivity, the device is preferably tested for other neurotransmitters such as noradrenaline, tyramine, glutamic acid, aspartic acid, taurine, and proline that could introduce an unwanted cross-sensitivity fluorescence response. Finally, in vitro testing of the device preferably using traditionally extracted interstitial fluid from human donors is conducted.

Samples are taken from individuals exposed to high levels of pesticides, and a control set is taken from those who were not exposed to toxic environments.

A sample result of this fabrication and testing process is preferably a silicon-based capillary array bed (PμP) with a chemical immobilization protocol for the detection of acetylcholine, which is a biomarker for oganophosphate type pesticide exposure. In addition, a sensitivity profile is established. The PμP microstructure design allows it to be readily interfaced and integrated as a module to the B-FIT transdermal sampling platform. The transdermal sampling process is preferably initiated using a minimally invasive micro-thermal ablation heater to reach the stratum corneum/viable epidermis interface, allowing for extraction of interstitial fluid. The B-FIT microsystem makes use of silicon fabricated capillary arrays to allow for interstitial fluid transport to a glucose-sensing patch situated on top of the array. The basic capillary array structure of the PμP microdevice can be incorporated into the B-FIT. The detection mechanism for the biomarker acetylcholine in PμP preferably consists of the synthesis of a fluorescent spyropyran that is surface immobilized. With the chemistry identified, surface modification of the bed is carried out, allowing for ease of manufacture of low-cost, minimally-intrusive chip scale detection.

The chemistry developed relies upon an alternate preferred embodiment of the B-FIT microsystem device, incorporating a photonics component instead of a glucose patch. This system is preferably fitted with waveguide technology on the top of the array, which is used to transmit and detect excitation and fluorescence light, respectively. Again, the PμP microdevice is ideally suited as a module to the B-FIT, in view of the fluorescence detection of acetyl choline. Testing of simulated body fluid and human serum can preferably be done on the test bed to determine the sensitivity and the specificity of the chemistry.

The present invention allows for the fabrication and chemical immobilization of any number of biomarkers, thereby creating a set of modules to be "plugged into" the B-FIT platform. Numerous examples, possibilities, and applications exist, ranging from a vast number of molecular biomarkers for health monitoring through enzyme and metabolite detection, to hormones. For pesticide detection some of the other key biomarkers would be acetylcholinesterase, acetic acid, and choline. It is also important to detect other analytes, aside from organophosphates, made possible through the use of the PμP microdevice. These include anticholinesterase insecticides (phosphorothionates), organochlorine insecticides (DDT, Dieldrin, Lindane), pyrethroid insecticides (Permethrin, Fenvalerate), herbicides (TCDD, Paraquat), and rodenticides (Warfarin, Diphacinone, sodium fluoroacetate, strychnine) Other key biomarkers to trace would be the antidotes such as atropine and pralidoxime.

Processing steps and the respective equipment in the fabrication of the PμP preferably include the following: (1) lithography: a front-side mask aligner capable of 1 μm line resolution with UV and deep-UV photolithography; a fixture capable of two sided alignment; a photo-resist spinner, pre- and post-bake ovens and associated processing chemicals; (2) deposition: a magnetron sputtering system capable of depositing metals (Al, W, Ni, Ti, Pt, etc.), and magnetron reactive sputtering of oxides which can be provided in the fabrication; an e-beam evaporator with three hearths for low energy deposition of metals; and deposition apparatus for PECVD oxides and nitrides for coating surfaces to adjust for stresses and adhesion; (3) film treatment, to adjust the stresses and strengths of films and membranes using rapid thermal annealing capability; (4) photo-mask design and fabrication; (5)

etching: deep reactive ion etcher (DRIE), RIE equipment and wet TMAH etching; (6) diffusion and heat treatment: high temperature furnaces capable of wet and dry oxide growth and furnace soak annealing which can be required for heaters comprised of dolled silicon; and (7) measurement: a thin film stress tester and a Leitz thin film analyzer or a Nanometrics Automatic Film Thickness measuring apparatus for measuring film thickness. Microscopic examination is available with a high quality Leitz microscope and a Zeiss SEM with EDS.

The transdermal transfer system (TTS) is preferably manufactured using various standard processing and fabrication technologies. The TTS microdevice fabrication also relies on several micromachining steps, from simple bulk micromachining to deep reactive ion etching (DRIE) procedures.

Figure 20:
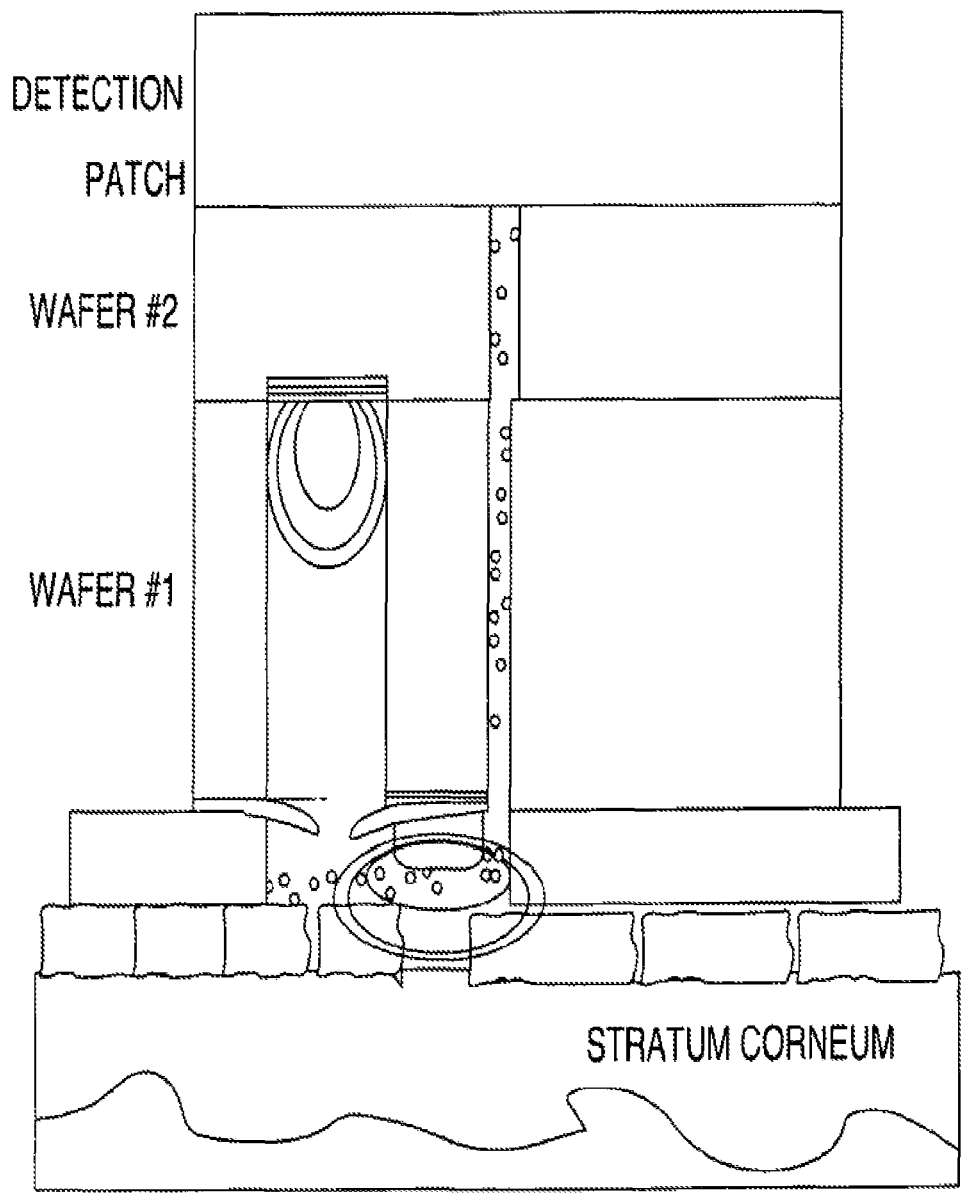
FIG. 20 illustrates a single reservoir capillary pair.

The fabrication process steps of the TTS microdevice preferably involve silicon processing of two wafers, as indicated in FIG. 20. Wafer #1 preferably comprises the reservoir channel, capillary channel, micro-ablation unit, and breakable seal. The micro-ablation unit contains the micro-heater along with a heat-sink to provide a highly conductive thermal path towards the stratum corneum. By incorporating a heat-sink on the micro-heater, the heat transfer is more favorably directed towards the stratum corneum. Wafer #2 preferably contains the reservoir micro-heater, which is preferably aligned to mate with the top of the reservoir channel.

Figure 21:
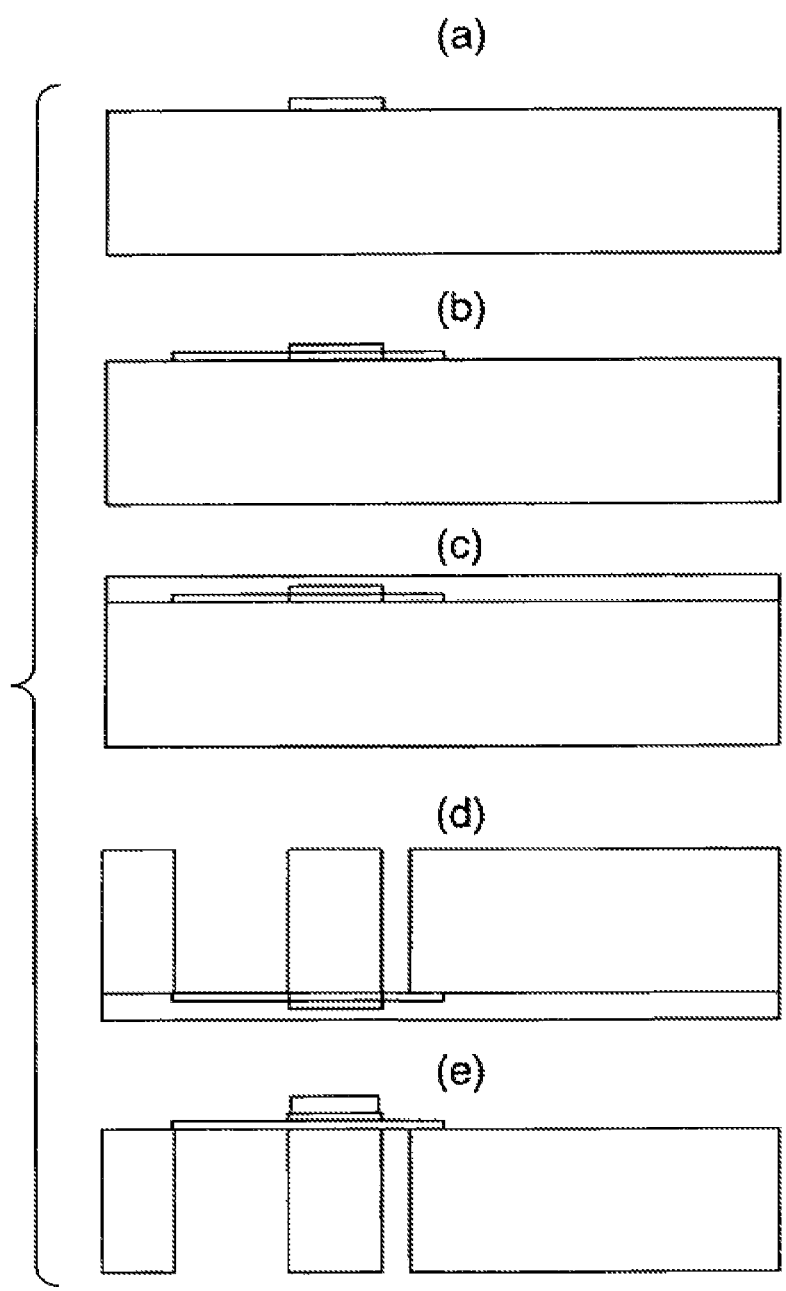
FIG. 21 illustrates a single reservoir capillary pair.

FIG. 21 (a-e) provides cross-sectional fabrication diagrams of the wafer processing steps for wafer #1. Double-sided polished, 300 μm thick silicon wafers are preferably used in the processing steps because working will be done on both the front and back sides. Initially, in one embodiment, the microablation heater is formed by depositing and patterning a metal layer onto a patterned silicon dielectric layer to form a serpentine heating element through which current is passed. The dielectric is preferably patterned as square region where the heating element resides. A preferred heater material can be selected through thermal simulation. In addition to the heating element, a temperature sensor can preferably be integrated alongside to monitor the local temperatures generated by the current through the heating coil. This is indicated in FIG. 21a, where processing occurs on the top-side of the wafer, but will eventually be inverted to become the bottom. In this version of the design, all bonding pads and traces are located in the plane of the heating element. The metallic traces and heating elements are preferably insulated and protected by depositing a layer of low-stress silicon nitride across the wafer. Although stress-free nitride is not required for this passivation purpose, it can find an application in the subsequent step.

Figure 4:
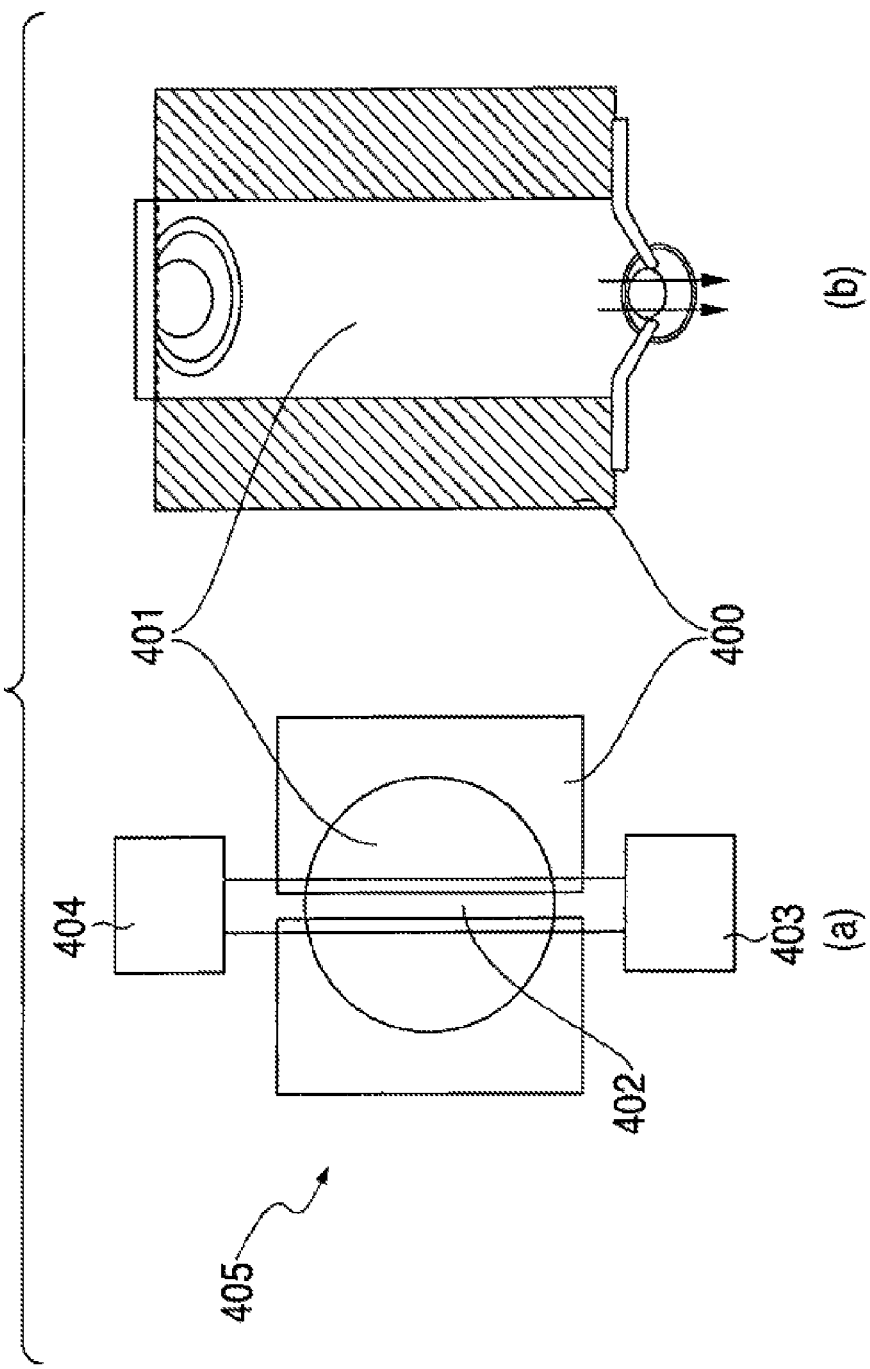
FIG. 4 shows the seal structure as viewed (a) from the bottom, and (b) in cross-section.

Referring back to FIG. 4 (a-b), the second step is preferably to fabricate the breakable seal. The seal is preferably composed of a bilayer formed by the low-stress silicon nitride layer, deposited in the earlier step, and a metal that can weaken at elevated temperatures. The area where the metal is deposited determines the location of the reservoir capillary. Since the capillary dimension is preferably on the order of 75 μm, the breakable seal must be situated in this 75 μm region in order to open the reservoir capillary. FIG. 4 shows the bottom view design of the breakable seal. It consists of two low-stress silicon nitride flaps bridged by the seal metal. By passing large enough currents through this metal strip, the heat is sufficient to weaken the metal seal thereby releasing the nitride flaps. Although the nitride layer is low in stress, preferably there is some controllable tensile or compressive strain. By adjusting the deposition conditions of the silicon nitride, it can be made in slight compression so that when the seal ruptures, the nitride flaps crudely act as unidirectional valves.

The preferred third major processing step is to form the heat-sink on top of the micro-ablation heating element. As discussed above, a heat-sink preferably directs the heat towards the stratum corneum instead of within the bulk silicon material. Without the heat-sink, the majority of the heat travels through the silicon, because its thermal conductivity is higher than air. By depositing an aluminum heat-sink on the heater, the resulting heat flow is approximately divided evenly between silicon and aluminum. This is because the thermal conductivities of both silicon and aluminum are comparable, but by selecting a metal with a higher thermal conductivity than that of silicon and aluminum, a more efficient heat transfer can be achieved. In a preferred embodiment, aluminum is used as the heat-sink material, however additional materials can be applicable. In addition to increasing thermal flow towards the stratum corneum, the placement of a heat-sink preferably reduces the overall distance between the source of heat and the skin barrier, thereby reducing power consumption. The aluminum is preferably patterned using a lift-off procedure. However, since a thick metal layer may be needed, preferably either a thick photoresist is used or the aluminum is deposited over the entire wafer. This may cause problems with the metal seal, therefore a thin protective isolating layer is preferably deposited prior to the aluminum. The aluminum is then lithographically patterned after the fourth step, to remain only on the micro-ablation heater. The patterning is done at a later stage in order to keep the surface planar for subsequent processing steps.

The fourth preferred processing step involves inverting the double-sided polished wafer to reveal the as yet unprocessed side. A photoresist masking layer is preferably deposited in order to pattern the openings where both reservoir and thin capillaries are formed simultaneously. These capillaries are both fabricated using deep reactive ion etching in order to obtain narrow, high aspect ratio through-wafer holes. The thin capillary is preferably designed to be 25 μm in diameter while the reservoir capillary is about 75 μm in diameter, both with nominal lengths of 300 μm. During the DRIE process, the silicon is anisotropically etched until holes are made through the wafer. However, for the reservoir capillary, the etching process terminates on the silicon-nitride that is already present on the wafer backside. This is because the nitride acts as an etch-stop for the DR1E etch process. As all processing of wafer #1 is now complete, the aluminum heat-sink can be defined and the isolating layer can be removed.

Figure 22:
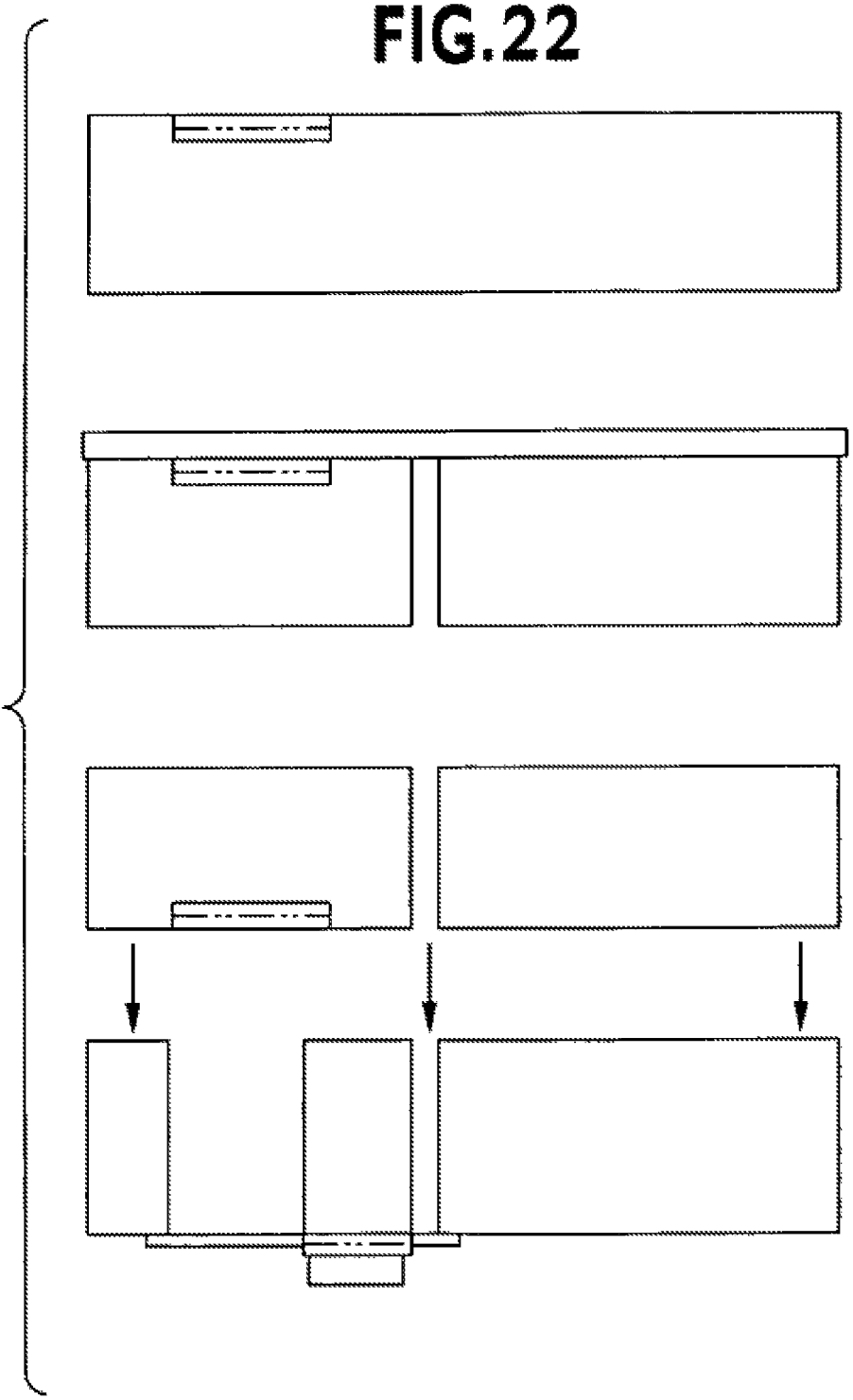
FIG. 22 illustrates fabrication steps for wafer #2.

The preferred processing steps for wafer #2 can also be outlined by a cross-sectional fabrication diagram, as shown in FIG. 22. The sequence of steps is far less laborious, however some alignment issues still exist. The first step in this preferred process is to fabricate the reservoir heating element on the front side of the silicon wafer. This is preferably done, as before, by depositing a heater material onto a silicon dielectric surface. The material is preferably patterned in the form of a heating coil, and is subsequently covered by a protective silicon nitride passivation layer. The preferred next step is to deposit on the surface an etch-stop dielectric layer. Next, the wafer is inverted and patterned using DR1E to form the connecting capillary opening. Once complete, the third step preferably involves depositing a layer of silicon dioxide onto the side containing the reservoir heater. This allows for the final step, anodically bonding wafer #1 with wafer #2. Care and attention preferably is taken to ensure that the reservoir heater mates with the reservoir capillary opening, and also to ensure that the capillary from wafer #1 connects properly with the capillary formed in wafer #2.

Each capillary and reservoir pair is preferably addressed individually so as to expose only one such pair to the skin surface in order to perform a single fluid analysis. Once employed, the open end of the capillary continues to remain exposed to the skin, but is not addressed for any further use.

A preferred embodiment includes additional considerations regarding the timing for signals to open seals and control heaters. The total amount of energy imparted to the heaters that affect the ablation of the stratum corneum and the time over which that energy is imparted are also considerations. The system is designed and tested for minimal ablation energy. That is, the minimum energy for the minimum duration is a significant parameter for operation, resulting in minimal damage of the underlying viable epidermis, and therefore minimizing the invasive nature of the process.

Other timing issues are also considerations, including the timing of the ablation process (heaters) with relation to the opening of a capillary seal. During the time the seal for a given capillary is being ruptured, the micro-ablation heater is preferably pulsed with an appropriate alternating current to thermally remove successive layers of the stratum corneum.

Another timing consideration is the heater pulses associated with the reservoir errrptying process. The timing of heater pulsing is a consideration to keep the reservoir flowing, and not taking up fluid from the stratum corneum. The heater at the top of the fluid reservoir preferably forces out the liquid contents. Control of this heater permits control of the flow of liquid during the reservoir/capillary analysis lifetime.

Preferably tests of the various subsystems are done to establish the dermatoxicological and clinical pharmacological advantages. The test sequence is preferably sequential, starting with simple tests on various materials, progressing to in vitro tests on human cadaver skin or animal skin, then to complete animal testing and finally clinical pharmacological testing with human subjects. One shot valves covering the capillary and reservoir are preferably tested and optically examined for successful deployment. The liquid reservoir is preferably initially tested to prove that it can be emptied of liquid contents. Initial tests are preferably also done on absorbent surfaces. Further testing is preferably done on a nonabsorbent surface to prove flow of liquid up the capillary. Determination of the optimal flow rate for the reservoir and capillary combination is preferably determined based on glucose concentration at the patch detector.

The glucose detector patch material is preferably tested for sensitivity using standard in vitro wet chemistry methods, to assure that its cellulose platform-glucose detector material is capable of reflectance densitometric detection of at least 10 fg of glucose per $\mu m^2$.

In vitro (using cadaver skin) and in vivo animal and human biomechanical tests of FDA approved biocompatible adhesives and adhesive membranes obtained from 3M, Inc. and Adhesives Research, Inc., are preferably conducted to determine optimal adhesive components and skin preparation conditions for occlusive, fluid tight adhesion requirements of the B-FIT device. Upon completion of initial tests of the B-FIT system, preclinical dermatoxicological testing begins. These tests preferably consist of a demonstration of the biophysics of the device, done in vitro using human cadaver skin or animal skin, and evaluation of local dermatological effects, done on live animals.

Dermatoxicological testing is preferably undertaken to demonstrate the biophysical properties of the B-FIT device. Biophysical testing is preferably conducted on animal or human cadaver skin. Full thickness human abdominal skin specimens can be obtained commercially from Vitron, Inc. (Phoenix, Ariz.) and other vendors. Animal tissue samples can preferably be used to establish a baseline and mitigate costs. The skin samples preferably serve as a platform to investigate and optimize the thermal ablation mechanism. The B-FIT system has several different ways to ablate skin. The goal of the heat/ablation step is to remove the stratum corneum with no damage to the viable epidermis. The first set of experiments preferably determines the optimal ablation conditions, for example, temperature peak, pulse duration, number of pulses, among others.

Tests to determine the optimum ablation conditions are preferably accomplished using optical and electron microscopy and surface profilometry using an atomic force microscope in order to view and measure (a) depth and volume of ablation hole, and (b) the epidermal cell structural integrity so as to provide sufficient ablation of the stratum corneum without penetrating the viable epidermis.

To obtain a preclinical evaluation of safety, in vivo animal testing of the B-FIT system is preferably undertaken, utilizing, for example, a hairless rat, guinea pig, or fuzzy rat specie. Clinical observations for gross evidence of skin irritation, ulcer formation, and inflammatory reactions are preferably made. Skin biopsies, examined using light and electron microscopy provide a closer examination of the device biophysical effects. Serial clinical and microscopic observations following removal of the device enable assessment of the healing time for the thermal ablation lesions.

Clinical pharmacological testing is preferably undertaken to determine the analytical precision and accuracy of methods to determine glucose levels via transdermal sampling relative to previously validated plasma assays. A preferred assay technology is based on glucose oxidase immobilization in micromachined capillaries. A validated plasma assay for glucose with acceptable limits of detection and quantification and with acceptable intra- and inter-day coefficients of variation is used to compare with these assays in the clinical settings described in the two trials outlined in detail below. The disclosed trials are of identical design: the first in normal volunteers, and the second in patients with Type II (Adult Onset) diabetes mellitus.

In order to validate the analytical sensitivity of transdermal sampling to measure glucose, ten healthy men and non-pregnant women who have signed an informed consent, fasted overnight, and have been screened to satisfy the inclusion and exclusion criteria of the study are enrolled in a clinical trial to measure glucose concentrations in their plasma or interstitial fluid before and during a glucose tolerance test. The B-FIT system is attached to the dorsal surface of the right hand using adhesive tape. An 18-gauge intravenous catheter is inserted in a forearm vein in the left arm. Venous blood samples (approximately 5 cc, and not less than 4 cc) are taken at appropriate intervals for the determination of plasma glucose concentrations. Concentrations of glucose in the plasma are determined by a validated assay, routinely used in clinical settings. These concentrations are compared to those determined in interstitial fluid using the B-FIT system. Plasma concentrations are measured on 8 occasions at 15 minute intervals over two hours, while interstitial fluid concentrations are measured for 0.5, 1, 2, 5, 10 and 15 minute periods over the same 2 hours before the administration of 75 grams of glucose by mouth. These data are used to optimize the sampling time for the B-FIT system. After the administration of glucose, plasma concentrations and B-FIT system-estimated concentrations are measured at 30 minute intervals for a further two hours. In healthy volunteers, the glucose plasma concentrations should range from 80 to 140 mg/dl under these conditions (Washington Manual of Medical Therapeutics, 28th edition, 1995).

Inclusion criteria for the clinical trial are, as follows: Group 1: men and women who are over the age of 21 years and under the age of 75 years, Group 2: male and female volunteers who are over the age of 21 and under the age of 75, and who carry the diagnosis of adult-onset diabetes by a board-certified endocrinologist. Group 1: taking no prescription medications or natural products. Group 1: showing clinically normal laboratory values for complete blood counts, serum chemistries (Na, K, Cl, HCO3, BUN, glucose and creatinine) and clinically normal liver enzyme profiles: SGOT, SGPT, alkaline phosphatase and bilirubin; ability to understand and carry out a signed informed consent describing this protocol.

The following subjects are excluded from the trial: subjects who, in the opinion of the investigator, is noncompliant with the protocol requirements; and women who are pregnant.

Once a subject has consented to participate in the study, the following procedures are conducted. Screening procedures are conducted within 21 days of study initiation and include: medical history and physical examination; review of inclusion and exclusion criteria; and blood and urine specimen collection. Subsequent to inclusion in the study, subjects undergo the following procedures: (1) subjects arrive at the location of the clinical trial at approximately 9 a.m. in the morning after an overnight fast. Vital signs (heart rate, respiratory rate, blood pressure and temperature) are recorded.

The B-FIT system is placed on the dorsal surface of the right hand and attached securely with tape. Recording occurs via a 50 micron cauterized lesion in the skin made by a small needle on the underside of the monitor that is not visible. The monitor is checked to ensure that it is recording. Vital signs (heart rate, respiratory rate, blood pressure and temperature) are recorded once the device has been attached once more. Samples of venous blood (5 cc or one teaspoon) are drawn from a catheter inserted in the a left forearm vein for the measurement of glucose according to the above schedule while the subject is supine. Additional blood samples are drawn four hours and eight hours after the first. The B-FIT system monitor tape and device is removed. Patients are discharged and allowed to return home.

With regard to the blood sampling schedule, five mL venous blood samples are collected in vacutainers in the manner described above. The total number of blood draws during the course of the study including the screening samples is 14 (12 study draws and 2 screening draws for hematology, chemistry, and liver enzymes, respectively). The total volume of blood drawn should not exceed 100 mL. Vital signs (heart rate, respiratory rate, blood pressure and temperature) are taken before and after placement of the device and catheter and after the last blood draw has been taken and the device and catheter has been removed. Patients are encouraged to report any notable irritation on the arm where the device is placed. A physician is constantly available to subjects enrolled in the study for concerns related to bruising or infection in the skin due to the intravenous catheter or multiple blood draws. In addition, symptoms of polyuria and polydypsia are carefully noted and paid attention to during the study with diabetic patients, and insulin is available for immediate injection by physicians and nurses should the need arise. Statistical analysis include plasma glucose concentrations determined using the clinical plasma assay as compared with the values obtained using the B-FIT system. If the correlation coefficient is >0.8 with a significance $p<0.05$, the measurements are deemed valid.

The second clinical trial with diabetic patients is conducted using an identical study design. Patients are allowed to take oral hypoglycemic medications on the day before, but not on the morning of the study, and are asked not to inject insulin during the study period: Once the study period is over, patients are allowed to eat and to resume their routine diabetic regime. In addition to the safety considerations described above, careful clinical monitoring and the availability of insulin is paid great attention to while these subjects are under study.

The B-FIT system preferably utilizes many different microfabrication technologies and strategies, ranging from simple bulk micromachining to the more complicated deep reactive ion etching (DRIE). Referring back to FIG. 5, a cross-section of a preferred one channel system microdevice is shown, preferably comprising of three main components: (1) the main body containing several serpentine capillary channels, each with its own reservoir channel, to sample and analyze physiologically compatible fluid; (2) a bottom capping section to form the lower part of the serpentine structure and to contain micro-heating elements to thermally porate the epidermal layer for substantial physiologically compatible fluid extraction; and (3) a top capping section which forms the upper part of the serpentine channel, and, if necessary, to contain electrodes for assisting the flow of physiologically compatible fluids using electro-osmotic pumping through horizontal segments of the serpentine channel. The first and second components together form the disposable modules of the system. These interchangeable B-FIT elements are inserted into the main connection receptacle after all analysis capillaries have been used.

The reservoir and capillary channels are preferably fabricated in a standard silicon wafer using deep reactive ion etching in order to obtain narrow, high aspect ratio throughwafer holes. The capillary charnels are preferably designed to be 25 μm in diameter with a nominal length of 500 μm, while the reservoir channels are 50 μm in diameter, but etched slightly less than 500 μm. The lateral portion of the serpentine capillary channel is preferably formed by recessing the silicon surface by 25 μm. This region also preferably has a highly reflective metal deposited on the surface to facilitate the mechanism for optical detection of the analyte. After bonding the silicon with a top capping section, the serpentine structure becomes complete. With these dimensions, physiologically compatible fluids, such as perspiration or interstitial fluids, can be drawn into the open ends of the channels through capillary action. Furthermore, the fluid within the reservoir is preferably used in conjunction with capillary action, and washes over the dermal region being tested, thereby assisting in the transport of the physiologically compatible fluids through the smaller channel. By activating the internal capillary channel surfaces to sustain a specific antibody immobilization, the fluids can be preferably analyzed by antibody-antigen complexation. A series of such capillaries, each with its own reservoir channel, is contained within a single device element. Each analysis capillary and reservoir pair is preferably addressed individually to expose only one such pair to the skin surface in order to perform a single fluid analysis. Once employed, the open end of the capillary continues to remain exposed to the skin.

The bottom capping unit is also preferably made using silicon and serves two other major functions, aside from the role of forming the lower structure of the serpentine channel. Micromachined heating elements incorporated within this section are preferably used to thermally porate the skin surface, allowing greater availability of interstitial and physiologically compatible fluids within the channels. Simultaneously occurring during the stratum corneum poration procedure, the micro-systems are preferably used to individually address each of the capillary-reservoir pairs. Initially, all open ends of the channels in contact with the skin are covered by a seal that can be "blown" to reveal a single analysis capillary. This cracking procedure can be effectively controlled using large thermal gradients in close proximity to the seal, such as those afforded by silicon micro-resistors. The micro-heaters are preferably integrated in the silicon region surrounding each of the capillary-reservoir channels. The connecting micro-capillaries in this section are preferably formed using DRIE, each being aligned with the vertical micro-capillaries from the main body.

Unlike the two previous components, the top capping layer is preferably made out of plastic and used to accomplish several tasks. Firstly, it completes the upper structure, or lateral portion, of the serpentine channel. This area, preferably, is the detection region of our microsystem. Secondly, by using plastic, an imbedded waveguide can preferably be fabricated within the material, with its orientation running parallel to the silicon surface and forming the basis of the integrated photonics analysis system. In addition, to couple the light from the waveguide into the detection region, a micro-mirror is preferably integrated within the plastic. In addition, for more effective light coupling and better efficiency, a micro-lens is preferably integrated within the plastic located directly above the detection region. The micro-mirror is preferably integrated as a pressed component within this top section by using a triangular form to indent the plastic. The resulting indentation preferably has a 45° angle with respect to the surface. Deposition of a highly reflective material is made on the resulting beveled angle to render a micro-mirror that reflects the horizontally-directed light from the waveguide downward. The integrated microlenses can also be stamped directly into the plastic or can be incorporated as separate units placed within the plastic by using injection molding. In either case, the lens does not need to be of high quality, but should simply be able to diverge light originating from the waveguide. The illumination produced by the light from the waveguide will cause the tagged analytes to fluoresce. The light produced is then reflected from the bottom surface of the detection region back through the now converging lens.

Returning to FIG. 6, the three possible (controllable) states of the individual microcapillary systems are shown. The leftmost micro-capillary system (#1) shows an exhausted capillary pair that has already been used for an analysis procedure. This first pair shows the completed thermal ablation, microfluid flow and capture of glucose from exposed interstitial fluid, encounter with the glucose detection patch, and bluish color reaction evident at the upper surface of the chip. The middle micro-capillary system (#2) is performing an on-demand analysis. The rightmost capillary system is ready for a future, on-demand analysis.

A purpose of the microdevice is to facilitate the transfer of molecules of glucose or other poorly permeable analyte(s) from interstitial fluid in the viable epidermis, located just beneath the inner surface of the stratum corneum, to the detection patch situated on top of the microdevice. The microdevice enables contact of the microfluidic sampling fluid directly with interstitial fluid by thermal micro-ablation of the stratum corneum. By direct interface with interstitial fluid, the microdevice enables sampling of, not only the normally-inaccessible polar molecules, but also impermeable larger molecules such as proteins.

The first in a preferred programmed sequence of events is the flow of electrical current through the reservoir heating element to create a minute hydraulic pressure in the sealed reservoir containing physiologically compatible fluid. The second and third steps occur almost in unison, and comprise two separate currents through both the breakable seal and the micro-ablation heater. The seal preferably is a metal-dielectric bilayer that ruptures at elevated temperatures. The metal seal is preferably surface deposited on a low-stress silicon dielectric element to reduce the chances of compromising the seal integrity prior to its operation. Once the seal is broken during an analysis procedure, the physiologically compatible fluid preferably flows down from the reservoir and across the region that has been thermally ablated by the micro-heater. During the time the seal is being ruptured, the micro-ablation heater is preferably being pulsed with alternating current to thermally remove successive layers of the stratum corneum, which is typically about 30-60 μm in thickness. The micro-ablation preferably occurs in a highly confined volume of the stratum corneum, approximately 50 μm×50 μm×30 μm. The physiologically compatible fluid from the now-open reservoir interfaces with the interstitial fluid and, due to the dual actions of the reservoir heater and capillary force, the mixture is transported towards the detection patch. The bulk of the physiological sampling fluid is preferably forced out of the reservoir, emptying over the skin surface region and into the absorbent detection patch. In addition, a strong, Band-Aid-like adhesive film preferably keeps the microdevice in fluid-tight contact with the skin, preventing escape of interstitial and physiologically compatible fluids from the analysis region. The fluids are preferably forced up the analysis capillary to the detection patch, directly above the capillaries on the microdevice and, for example, in one embodiment, generate a color change to indicate the presence of glucose.

The microsystem component of the present invention is preferably based on molecular scale manipulation using enhanced transdermal transfer of metabolites from interstitial fluids, and resultant detection with enzyme immobilized chemistries. Samples are preferably collected using a minimally non-invasive transdermal microdevice and trace quantities of analytes, which reach the skin surface by passive diffusion from interstitial fluid underlying the outermost layer of skin (the stratum corneum) can be detected. Since these analytes originate from other parts of the body, transported to the interstitial fluid via blood circulation, they reflect a variety of physiological processes including body exposure to environmental chemicals or microbes, as well as internal metabolism. Micro-layers of the stratum corneum are gently removed enabling uptake of interstitial fluid from the viable epidermis, which lies just beneath the stratum corneum.

Figure 8:
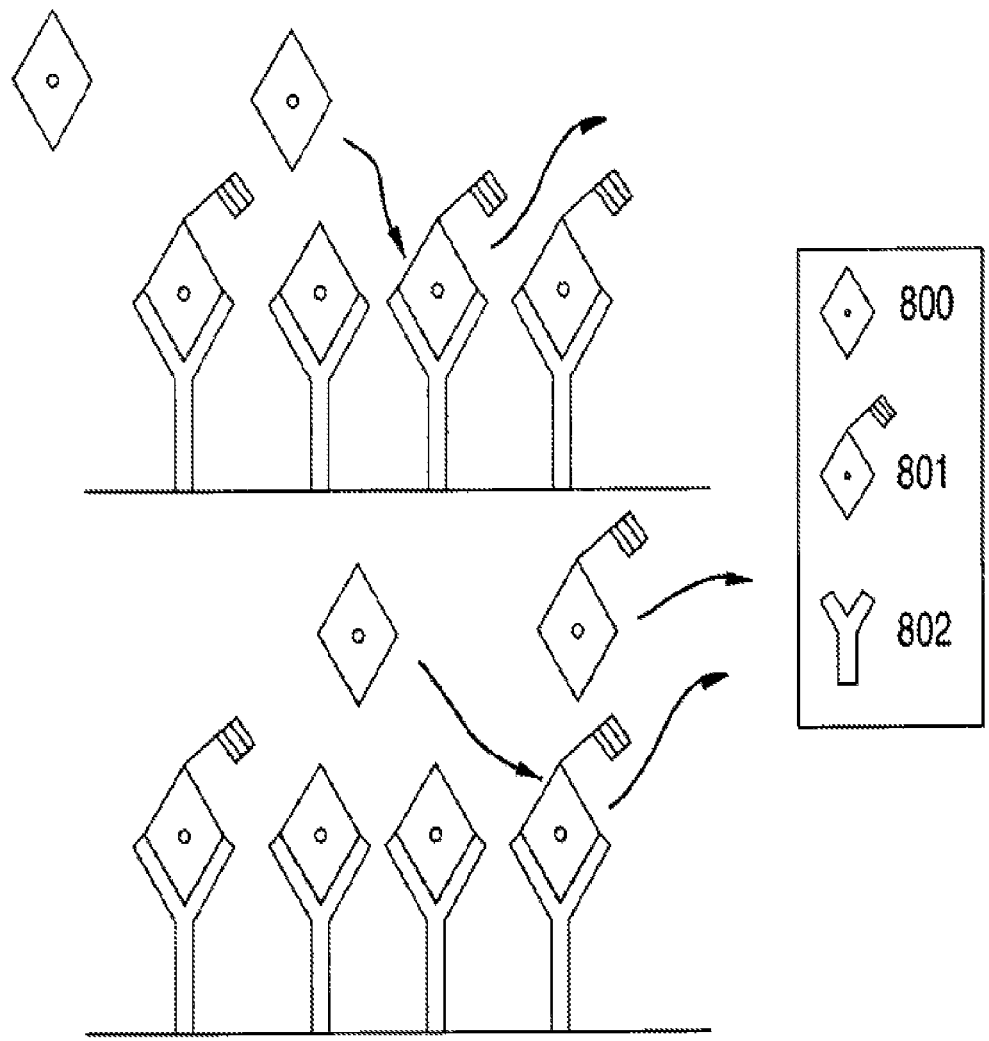
FIG. 8 is a schematic illustration of a detection scheme using fluorescently labeled proteins or metabolites.

A preferred detection scheme for determination of health and other important biological markers utilizes similar surface and biochemistry for each assay. Returning to FIG. 8, a preferred procedure for the detection scheme is shown. A preferred procedure is to covalently attach antibodies of the protein or metabolite of interest to a capillary wall that incorporates a fluorescently tagged antigen. The tagged antigen is replaced by competitive binding with the protein or metabolite of interest from the interstitial fluid sampled. The fluorescent antigen is kicked off into solution to be detected down stream in the collecting chamber by the photonics component. The fluorophore excitation and emission characteristics are matched to the photonics and visa versa for integrating the right wavelength source, detector and filters to properly excite and determine emission in the photonics module.

As an example, the following three proteins of various molecular weights can be used for monitoring health properties: troponin I, C-reactive protein, and prealbumin. Anti-troponin I is covalently attached to the capillary wall following a silane surface treatment of aminopropyltrimethoxysilane (APTS). Troponin I is fluorescently tagged using either fluorescein or rhodamine and bound to the antibody attached in the capillary. Using competitive binding of troponin I from sampling, the fluorescently tagged troponin I is replaced into solution and detected downstream. The above procedure can also used for both C-reactive protein and prealbumin, albeit modified to take into account differences between these proteins.

The surface chemistry is characterized stepwise to ensure sufficient surface coating. The amount of bound antibody and competitive binding studies is tested using a variety of different instruments such as XPS, fluorescent plate reader, fluorescent microscope, or separation techniques. In another example, polyclonal antibodies raised against the caffeine metabolites 5-acetylamino-6-formyl-3-methyl urea (AFMU) and 1-methylxanthine (IX) are immobilized on the micromachined capillaries. The capillary tubes are modified by chemical treatment in order to introduce hydroxyl moieties on the capillary surface. The surface hydroxyl groups are then reacted with APTS, producing a molecular tether with free amine moieties at the end of the three-carbon chain.

The sugar residues in the Fc region of the antibodies raised against AFMU and IX are oxidized using periodate to generate aldehydes. The antibodies are anchored to surface of the micromachined capillaries through Schiff base formation between the aldehydes on the antibodies and the amines on the molecular tether. In this manner, the antibody binding regions is directed away from the surface of the micromachined channels.

The amount of antibody immobilization on the surface of the microchannel is preferably determined by analysis of the protein content of the binding solution before and after exposure to the microchannels. The binding activity of the immobilized antibodies is determined using displacement of the fluorescent-labeled AFMU and IX probes and the observed activity is compared to the activity of equivalent concentrations of non-immobilized antibodies to yield binding affinity per mg of immobilized antibody indices (BAI).

For the caffeine metabolites, in vivo and in vitro testing is conducted to assess the specificity of the antibodies AFMU and 1X. The ability to measure the ratio of these metabolites using the device of the present invention is assessed by comparing the ratio obtained using the portable biomedical monitoring system with the ratio obtained employing conventional HPLC methods. Devices modified with this assay are tested both in vivo and in vitro for provide a preclinical evaluation. These data are utilized as a baseline and preliminary data for testing the algorithm.

Antibodies for prealbumin, CRP, troponin I are currently available on the market and are used to assess the specificity of these antibodies to their protein compliment. As some commercial antibodies are not active or specific, this prescreening test is preferred to determine activity and specificity for each protein of interest. Specificity is preferably tested for each antibody by adding other substances similar in structure, which should not cross-react. For example, in assessing prealbumin the proteins such as albumin and globulins, among others, are added. In assessing caffeine metabolites, xanthines and xanthine metabolites are added. Assays using the antibody, the ligand and the fluorescently labeled ligand are preferably developed using techniques such as flow injection analysis (FIA).

Each completed assay is assessed for accuracy, reproducibility, linearity, and results are compared with those of existing procedures currently used in the clinical laboratory. A preclinical evaluation for in vivo and in vitro testing is done and the data is utilized in the algorithm developed.

The portable biomedical monitoring system of the present invention is preferably based on molecular scale manipulation using enhanced transdermal transfer of metabolites and other body analytes using transdermal dosimetry immobilized antibodies in microchannels, capillary action for fluidic mobility, and integrated photonics for detection. Thus, the micro-fluidic chip interface technologies of the present invention provide controlled sample collection from host fluids, (circulatory and noncirculatory) and for the controlled delivery of fluids (drugs, chemicals) and target probes (antibodies, proteins, signal molecules). In addition, sample collection platforms of the present invention can simultaneously employ an "outward facing" device component for sampling air or liquid borne environmental target analytes and an "inward facing" component for detection of target analytes emanating from the skin surface or accessible body fluid.

The apparatus and process of portable biomedical monitoring disclosed herein is adaptable to a wide variety of chemistries. For example, the portable biomedical monitoring device can include chips which monitor health (Chip "A") and illness or infection (Chip "B"). Chip A can measure molecules like glucose to establish a baseline of the subject's health state in both normal and high stress situations. Changes from these baseline limits will signal a need for Chip B. Chip B is designed to determine the exact cause of illness. For example, Chip B can contain antibody conjugates for parathion and its metabolites that emulate a chemical warfare agent. The structure of the microsystem is adaptable for many other types of chemistries based upon drag metabolism and/or "probe drugs".

Drug metabolism is the process by which drugs are converted, by enzyme-catalyzed reactions, to products or metabolites which are readily excreted in the urine and bile. One pathway of drug metabolism are phase I reactions, which involve the creation or modification of a functional group in the substrate molecule. The cytochrome P450-dependent (CYP) microsomal mixed function oxidase system is a very important enzyme system for these reactions. A second major pathway involves phase II reactions, in which the drug or a phase I metabolite is conjugated with a water soluble endogenous substrate. Phase II reactions involve a diverse group of enzymes known collectively as transferases. This group includes UDP-glucuronyltransferase, UDPglycosyltransferase, glutathione-S-transferase, sulphotransferase, methyltransferase, and N-acetyltransferase.

Drug metabolism is affected by dietary and environmental factors. For example, alcohol, certain food constituents and compounds in cigarette smoke have been observed to affect the biotransformation of many drugs, as have industrial pollutants and pesticides. Genetic factors also play an important part in the control of drug metabolism and it has been observed that there is much variation in drug effects between individuals. For some enzymes, discrete genetic subgroups are present in the human population. These genetic polymorphisms are generated by mutations in the genes coding for these enzymes which cause decreased, increased or absent enzyme expression or activity. Genetic polymorphisms of several CYPs have been identified and their activity falls into two clearly defined and qualitatively different populations: individuals whose rate and extent of metabolism is poor (poor metabolizers, PMs) and those who have faster or more extensive metabolism (extensive metabolizers, EMs). Genetic polymorphisms of some phase II enzymes also exist. For example, N-acetyltransferase-2 (NAT-2) is affected in this way and this acetylation polymorphism relates to the metabolism of a variety of drugs and carcinogens. Numerous alleles are associated with decreased function of this enzyme and a bimodal distribution is observed: 50-60% of individuals are genotypically slow acetylators and the rest of the population are fast.

In healthy individuals, the metabolic genotype normally predicts the metabolic phenotype. That is, for a particular enzyme, genotypically extensive metabolizers are observed to efficiently metabolize drugs that are substrates for that enzyme, and genotypically poor metabolizers are deficient in that process. However, drug interactions, infection, disease progression and malnutrition may produce changes in the relative levels and activities of metabolizing enzymes. Thus, in healthy individuals the relationship between genotype and its expression (phenotype) is conserved; i.e., FAST genotypes produce FAST phenotypes, while SLOW genotypes produce SLOW phenotypes. However, a disease state of the individual can alter this relationship, as can diet, smoking, alcohol, environmental chemicals, and biological or chemical warfare agents. For this reason, the determination of metabolic phenotype (the measure of actual enzyme activity) is of great importance and can be used as a direct and sensitive probe of health and clinical status. In a preferred embodiment, identification and quantification of specific metabolite patterns produced by innocuous test compounds or probe drugs can be utilized to determine the metabolic phenotype of a subject. For example, caffeine is metabolized by several routes including one involving NAT-2. Thus the urinary ratio of 2 metabolites, 5-acetylamino-6-formylamino-3-methyluracil (AFMU) to 1-methylxanthine (IX) is an index of NAT-2 activity.

Examples of numerous embodiments follow. Each embodiment can be practiced alone or in conjunction with other embodiments of the invention.

For example, as mentioned above, dispositional or metabolic markers of "stress" can be monitored, including but not limited to, chemistries for the detection of different chemical probes of human health, such as glucose, caffeine, ethanol, and dextromethorphan. "Stress" can manifest itself via detectable alterations of many internal metabolic pathways, such as in altered insulin-glucose patterns or aberrant hepatic catabolism of safe, commonly used stimulants (caffeine) or antihistamines (dextromethorphan).

The enzyme N-acetyl transferase (NAT-2) metabolizes caffeine. This enzyme is highly polymorphic. The activity of NAT-2 is known to be associated with adverse drug effects, diverse toxicities and predisposition to disease. Two major metabolic phenotypes have been identified: fast and slow N-acetylators. The expressed activity of NAT-2 (phenotype) has been shown to be affected by acute and chronic disease states. For example, in HIV+ and AIDS patients, the presence of an acute illness reduces the expressed activity of NAT-2, changing a patient with a fast NAT-2 phenotype into one with a slow NAT-2 phenotype. When the illness is resolved and the patient is returned to the initial clinical state, the patient again expresses a fast NAT-2 phenotype. Thus, the determination of an individual's NAT-2 phenotype and the monitoring of changes in this phenotype can be a direct and sensitive probe of that individual's health and clinical status. This determination allows prediction of whether patients are FAST or SLOW metabolizers prior to initiating drug regimens. This approach also allows for the screening of all patients before drug treatment is initiated so that appropriate dosage regimens are given at the outset of treatment and drug overtreatment or undertreatment is avoided.

The NAT-2 phenotype can be determined by a number of probes. In the preferred embodiment, caffeine is used because of its wide distribution and relative safety. In studies using caffeine as the probe, the phenotype of the enzyme is determined by the ratio of two caffeine metabolites: AFMU to IX. Based on the ratio of these metabolites, the activity of the enzyme can be determined. Polyclonal antibodies are grown against the metabolites AFMU and 1X and then purified. These antibodies are successfully used to determine NAT-2 phenotypes.

The preferred detection scheme consists of the anchoring of antibodies of a particular metabolite or chemical antigen to the surface of the capillary. The antibody is bound to a special antigen attached to a fluorescent tag such as rhodamine. As the antigen flows into the channel it will release the fluorescent tag which is detected downstream.

Thus, in an alternative embodiment, phenotyping using NAT-2 is conducted to indicate an infected or diseased state. The enzyme NAT-2 is highly polymorphic. The activity of NAT-2 has been associated with adverse drug effects, diverse toxicities and predisposition of disease. The monitoring of changes in this phenotype is a direct and sensitive probe of the soldier's health and infection status.

In a further embodiment, organophosphate chemicals (nerve) agents are monitored using the insecticide surrogate model compound parathion. Since "nerve gas" type chemical weapons like Tabun, Sarin, and Soman act by inhibition of acetylcholinesterase, the organophophate insecticide, parathion (or its metabolites) provides an excellent "surrogate" analyte to detect exposure. A parathion monitor, thus, has important industrial and civilian applications.

In a further embodiment, inflammatory sequeli to microbial toxins are monitored, including, for example, interleukin-1 (IL 1); interleukin-6 (IL 6); and tumor necrosis factor (TNF); among others. Circulating IL 1, IL6, and TNF present candidate analytes that can be collected and detected using permeation enhanced transdermal techniques and advanced detection system designs in accordance with the present invention.

In a further embodiment, microbial toxins are monitored, including, for example, anthrax, botulinum toxin, endotoxin, among others. Although microbial toxins are typically large molecules, their extremely high biological potency, coupled with enhanced outward migration using microscopic physical barrier modification techniques (for example, thermal microablation) can permit transdermal dosimetry employing detection systems incorporating toxin responsive components. In addition, antibody tags can be used for identification of infecting agents and determination of bacterial and viral loads. Moreover, the determination of D-amino acids (from bacterial sources) can enable the monitoring of the response to antibiotic therapy.

In a further embodiment, spore metabolites can be monitored. Circulating biochemical metabolites arising from human catabolism via lymphatic and hepatic pathways of microbial spores are collected and detected using the techniques and optimized detection system designs of the present invention.

In a further embodiment, specific proteins are monitored, such as those referred to in the table below.

| Protein | Concentration (mg/L) | Mol. Wt. (kD) |
|---|---|---|
| Prealbumin | 70-390 | 54 |
| C-reactive Protein | 0.06-8.2 | 115-140 |
| Troponin I | <0.0001 | 76 |

Prealbumin (MW 54,000) is known as being an important marker for nutritional status. The reference range for 0-1 month old is 70-390 mg/L. Uses of this embodiment include but are not limited to screening inner city pediatric populations for nutritional status, as well as screening all patients for nutritional status, particularly prior to surgery.

C-reactive protein (MW 115,000-140,000) is an acute phase reactant and as such is elevated in many disease processes. The reference range in adults is 68-8200 μg/L. The measurement of this protein provides a good indication of health vs. disease. C-reactive protein is also an important prognosticator of heart disease and impending myocardial infarction. Thus, this assay could also be used to screen for cardiovascular health.

Troponin I is recognized as a useful and specific marker for acute myocardial infarction. The reference range in adults is <0.1 μg/L. In myocardial infarction patients it is >0.8 μg/L. This assay provides a real time evaluation of troponin I in the emergency rooms of hospitals and provide the earliest recognition that a patient needs to be admitted to intensive care units.

In addition to monitoring, the biomedical monitoring system of the present invention can provide drug delivery with feedback control in bursts to maintain concentrations of a specific agent within the body at specific levels throughout the day, levels which can vary on a day to day basis and during the day. Examples of such agents include the hormones estrogen and testosterone. The decrease that occurs in estrogen with age is intimately related to the increased risk of osteoporosis and cardiovascular disease in women. Moreover, the replacement with pharmacologic estrogen may improve mortality from cardiovascular disease, reduce the risk of osteoporotic fractures and may play an important role in protecting women against Alzheimer's disease. These diseases have immense societal impact and financial cost, but their treatment with replacement estrogen is
associated with a host of side effects including, not least the development of breast cancer and uterine cancer, but also a host of other effects including skin changes, weight changes and depression. Although no medicine has been shown to be as effective as estrogen itself, a huge effort has been expended to develop modified estrogens that have selective actions on bone, breast or other tissues (the development of specific estrogen receptor modulators or SERMs). The approach of administering effective estrogen in a physiologic, controlled and monitored manner is attractive in that it remains the most effective medication and innovative therapeutic regimens utilizing it may prove of great benefit.

The delivery of testosterone in a controlled and monitored manner can also be useful. Serum concentrations of testosterone also decline with age, as they do in a number of pathological conditions, including HIV. Testosterone replacement strategies for the treatment of HIV and cancer wasting, male osteoporosis and chronic obstructive pulmonary disease are emerging and can also be useful for short term controlled administration post-operatively after major surgery to enhance the rate and the likelihood of successful recovery. Feasibility of these embodiments is investigated through transdermal detection of estradiol (E2) in Rhesus monkeys and human females. A prototype solid phase E2 detection system (TED) can be incorporated in a trans dermal patch that immobilizes antibody against E2 in the TED, and analyzed ex-situ using a radioimmunoassay procedure. The E2 detection system is capable of detection less than 0.125 picograms. TEDs are first tested by emplacement for 24 hours on the chests of partially or fully castrated female Rhesus monkeys (n=3), treated with placebo or 20 ug/kg estradiol benzoate. The TED measurements distinguish between monkeys that have high circulating E2 concentrations and those who have none. TEDs can also be affixed on the forearms of four reproductive age human females who exhibit a large range of circulating E2 concentrations (48-382 pg/ml). E2 collected in TEDs range from 0.06 to 0.5 pg, and correlate roughly with circulating E2 concentrations. These data are consistent with an in vivo permeability coefficient of $4.3+/-0.5 \times 10^5$ cm/hr.

In a further embodiment, the portable biomedical monitoring device of the present invention can be used for pain management, determining how best to deliver codeine and morphine, among others, to minimize cytotoxicity, while achieving pain control.

In a further embodiment of the present invention, a MEMS-based physiochip can be used to non-invasively monitor fundamental physiological aspects related to human function under typical and atypical environmental conditions. By carefully monitoring of relevant physiological data such as body temperature, pulse rate, blood pressure, and heart activity (electrocardiogram) an infinitesimal change or anomalous behavior can provide an early indicator of stress to the human system.

In a further embodiment, passive or non-invasive transdermal dosimetry is used without physical or chemical modification of the normal skin barrier. This embodiment is practical for small molecular weight analytes that exhibit both lipid and water solubilities.

The following description of experiments and clinical trials is provided so as to demonstrate how various embodiments of the present invention perform. Suitable analytes for demonstrating the operation of these embodiments of the present invention are provided below. However, it is to be recognized that the systems and methods of the present invention contemplate analysis of a much larger set of analytes in the various embodiments of the present invention.

Development of Immobilized Nicotinic Acetylcholine Receptor (nAChR) Based-HPLC Stationary Phases and the Application of these Phases to the On-Line Determination of Drug-Receptor Interactions Preparation of nAChR-Detergent Solution.

Rat whole forebrain or transfected cells are suspended in 50 mM Tris-HCl, pH 7.4, (buffer A), homogenized for 30 seconds with Brinkmann Polytron, and centrifuged at 40,000×g for 10 min at 4° C. The pellet is resuspended in 6 ml of 2% deoxycholate or 2% cholate in buffer A and stirred for 2 hours. The mixture is centrifuged at 35,000×g for 30 minutes, and the supernatant containing nAChR-deoxycholate solution is collected.

Immobilization of nAChRs on MMparticles or Superdex 200 Gel Beads.

Dried IAM particles are suspended in 4 ml of the obtained detergent solutions containing nAChR subunits or subtypes. For the immobilization of one nAChR subtype, the mixture of IAM-detergent-receptor is stirred for 1 hour at room temperature. The suspension is dialyzed against 2×1 L buffer A for 24 hours at 4° C. The IAM LC support with immobilized nAChRs is then washed with buffer A, centrifuged and the solid collected.

A dried lipid mixture of 60 mg L-a-Lecitin (20% phosphatidylcholine), 10 mg L-a-phosphatidylserine, and 20 mg cholesterol is solubilized with 4 ml of obtained nAChR-detergent solution. The nAChR-lipid-cholate solution is mixed with 50 mg dry Superdex 200 beads. The suspension is dialyzed against buffer A for 24 hours at 4° C. Non-immobilized liposomes are removed by centrifugal washing with buffer A at 2,000×g.

($[^3H]$-epibatidine ($[^3H]$-EB) binding assays for the suspensions of nAChR-IAMparticles and nAChR-Superdex 200 beads: The nAChR-IAM particles, IAM particles, nAChR-Superdex 200 gel beads and Superdex 200 gel beads, corresponding to 30 mg dry material, are each suspended in 1.25 ml buffer A. A 250 gl aliquot of each suspension is incubated with 250 gl of ([$^3$H]-EB [1.5 nM] for 4 h at 24° C. in a final volume of 2.5 ml.

Experiments are carried out with and without added 100 μl of 300 μM (−)-nicotine. Bound and free ligands are separated by vacuum filtration through Whitman GF/C filters treated with 0.5% polyethylenimine. The filter-retained radioactivity is determined by liquid scintillation counting. Specific binding is defined as the difference between total binding and nonspecific binding. The amount of protein is determined using BCA reagent (Pierce, Rockford, Ill., USA) measured at 570 nm.

Chromatography based on nAChR-LAMcolumn or nAChR-liposome-Superdex 200 column: The nAChR-IAM particles or nAChR-Superdex gel beads are packed in a HR5/2 glass column and connected to a HPLC pump. [$^3$H]-EB is used as a marker and an on-line flow scintillation detector (525 TR) monitors the elution profile. All chromatographic experiments are performed at flow rate 0.4 ml/min at room temperature.

In zonal chromatographic experiments, a 100 μl-loop is used to apply the sample. The chromatographic data is summed up in 0.5-min intervals and smoothed using the Microsoft Excel program with a 5 point moving average.

In frontal chromatogram 50-ml sample superloop are used to apply a series of [$^3$H]-EB concentration through the nAChR-column to obtain elution profiles showing a front and plateau regions. The chromatographic data is summed up in 1-min intervals and smoothed using the Microsoft Excel program with a 10 point moving average.

Results: Immobilization of nAChR Subunits or Subtypes.

About 63 mg protein isolated from the membrane of transfected cells and 14 mg of protein prepared from the brain tissues are respectively immobilized on the per gram of IAM particles or Superdex 200 gel beads. Receptor binding assays using [$^3$H]-EB showed that the nAChR binding activities are retained after the immobilization procedure as shown in the table below. In parallel experiments, no specific binding of [$^3$H]-EB is detected on IAM particles and Superdex 200 gel beads.

| Sample | Specific Binding (%) | nAChR Density (nmol/g protein) |
|---|---|---|
| α4/β2 nAChR-detergent solution | 62 | 0.14 |
| α4/β2 nAChR-IAM[1] | 49 | 0.81 |
| α3/β4 nAChR-detergent solution[2] | 100 | 8.57 |
| α3/β4 nAChR-IAM2 | 97.8 | 5.09 |
| α3/β4 nAChR-liposome Superdex 200[2] | 29.4 | 1.45 |

[1]prepared from rat forebrain with detergent deoxycholate.
[2]prepared from transfected cells with detergent cholate.

Frontal chromatography with a3/β4 nAChR-IAM stationary phase:

The retention volumes of [$^3$H]-EB are 23 ml at the concentration of 60 μM. This retardation is primarily due to the specific binding to saturable sites of the receptors as indicated by a decrease in retention volume to 8 ml when the concentration of [$^3$H]-EB is increased to 450 μM 20 (Figure X, profile B). The binding of [$^3$H]-EB to the a3/β4 nAChR-IAM stationary phase could be reduced in competitive displacement experiments using known a3/β4 nAChR ligands in the mobile phase. For example, the retention volume of 60 μM [$^3$H]-EB decreased from 23 ml to 18 ml when a 60 nM concentration of the nAChR-ligand (−)-nicotine is added to the mobile phase and fell to 0.9 ml when the (−)-nicotine concentration is increased to 1000 nM. The decreases in retention volumes of [$^3$H]-EB relative to mobile phase concentrations of a displacer reflect the binding affinity of the displacer for the receptor. Using this technique, the relative affinities of nicotinic drugs for the a3/β4 nAChR are readily the relative affinities of nicotinic drugs for the a3/β4 nAChR are readily classified by determining the concentrations required to decrease the retention volumes of [$^3$H]-EB to a predetermined level.

To decrease the retention volumes of 60 μM [$^3$H]-EB from 9.5 ml 5 to 6 ml on an a3/β4 nAChR column (0.5×1.25 cm), requires mobile phase concentrations of 0.12 nM of (±)-EB, 1.7 nM of A85380, 45 nM of (−)-nicotine, 1,200 nM of carbachol or 21,000 nM of atropine, respectively. The relative affinities of these drugs for the a3/(34 nAChR determined by this method are therefore (±)-EB>A85380>(−)-nicotine>carbachol>atropine which is consistent with results from ligand binding assays using membrane homogenates. The relative affinities can be classified by the association constants calculated from the resulting data in the table below.

| Ligand | $K_d^1$ (nM) | $K_d^2$ (nM) |
|---|---|---|
| (±)-Epibatidine | 0.27 ± 0.05 | 0.38 ± 0.07 |
| A85380 | 17.2 ± 0.5 | 73.6 ± 6.3 |
| (−)-Nicotine | 88 ± 33 | 475 ± 52 |
| Carbachol | 1,280 ± t 30 | 3,839 ± 276 |
| Atropine | 14,570 ± 2600 | — |

[1]Frontal chromatography with a3/(34-IAM stationary phase (0.5 × 1.3 cm).
[2]Binding assay using cell membrane homogenates.

These dissociation constants ($K_d$) values show the same rank order as those of the values measured with binding assays using membrane homogenates. The low affinity of atropine ($K_d$: 17,200 aM) is also consistent with literature values.

Figure 23:
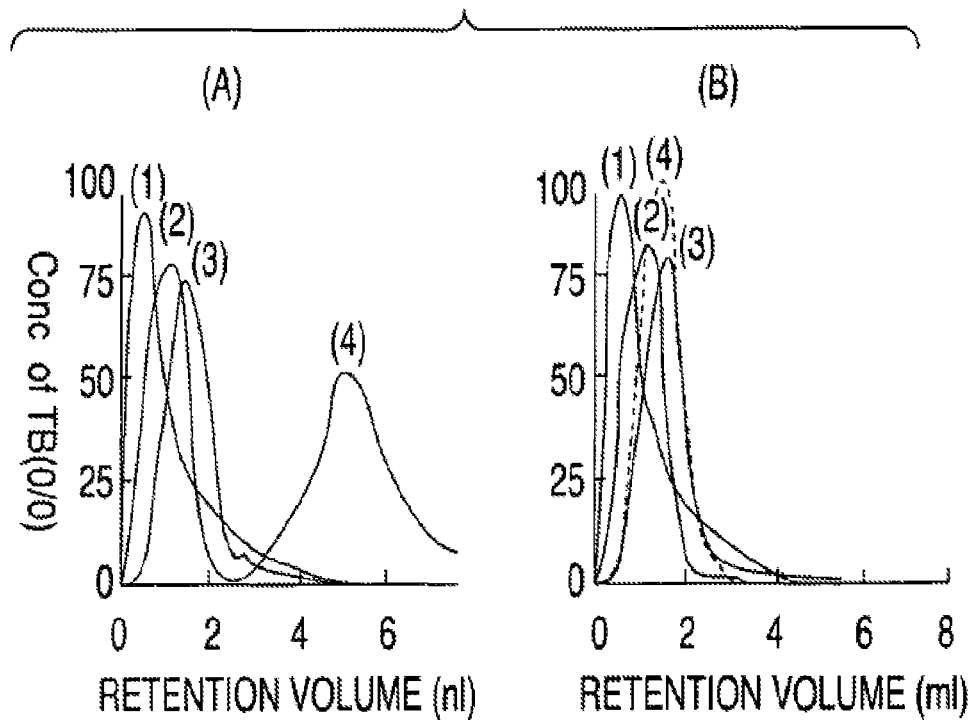
FIG. 23 illustrates retention volumes at varying concentrations of [3H]-EB.
Figure 24:
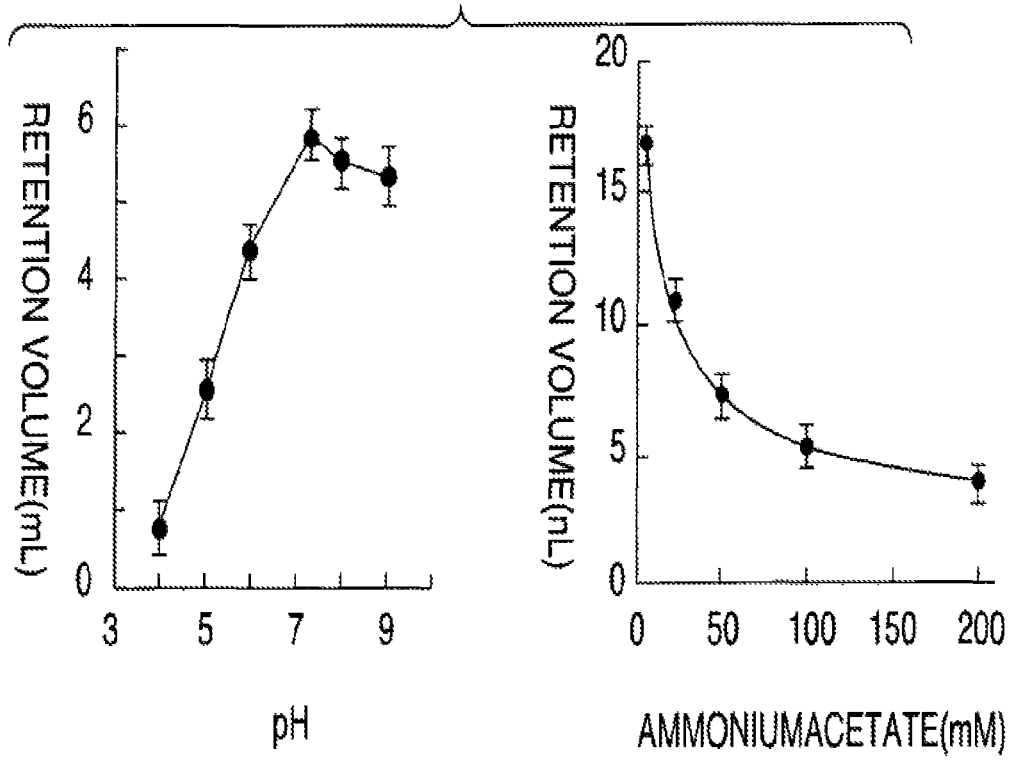
FIG. 24 illustrates retention volumes at varying pH and ionic strengths.

Zonal Chromatography for Determination of Different Specific Binding Activities of Immobilized nAChRs Subtypes:

Binding of [$^3$H]-EB is also measured in zonal format on the columns containing a3 subunits only, β4 subunits only, a mixture of the two cell types, or a3/β4 nAChRs. The retention of [$^3$H]-EB on a3 nAChR-IAM (peak 1, FIG. 23a), β4 nAChR-IAM (peak 2, FIG. 23A) and a3/β4 nAChR-IAM (peak 3, FIG. 23A) is low, and no significant change in the retention volumes is observed when a displacer, (−)-nicotine, is included in the mobile phase, [$^3$H]-EB is retained on the IAM column containing the immobilized a3/β4 nAChR-IAM (peak 4, FIG. 23A). The retention volume is decreased when the concentration of [$^3$H]-EB is increased or when (−)-nicotine is included in the mobile phase, peak 4 (dash line) FIG. 23B.

Specific Binding Activities of Immobilized nAChRs Subtypes.

The results of binding to immobilized receptors showed that [$^3$H]-EB and (−)-nicotine have higher binding affinities at nAChR a4/β2 subtype than at a3/β4-subtype and these results are consistent with the results determined from ligand binding assays using membrane homogenates as shown in the table below. The IQ values obtained from a4/β2 nAChR-liposome-Superdex 200 column are similar as those determined using a4/β2 nAChR-IAM column.

| Formats of nAChRs | $K_d$ of (±)-epibatidine (nM) | $K_d$ of (−)-nicotine (nM) |
|---|---|---|
| α3/β4 - nAChR-IAM | 0.27 ± 0.05 | 88 ± 33 |
| α3/β4 - nAChR membrane | 0.38 ± 0.07 | 475 ± 52 |
| α4/β2 - nAChR-IAMB | 0.044 ± 0.005 | 1.0 ± 2.3 |
| α4/β2 - nAChR membrane | 0.053 ± 0.002 | 7.2 ± 1.3 |
| α4/β2 - nAChR-liposome-Superdex 200 | 0.020 ± 0.08 | 7.4 ± 2 |

Effects of Ionic Strength and pH of the Mobile Phase on the Binding of [$^3$H]-EB:

The effect of mobile phase ionic strength and pH on the binding affinities of [$^3$H]-EB are determined with a α3/β4 nAChR-column. The retention volumes increased when the pH of mobile phase is increased from pH 4.0 to pH 7.0 and remained constant between pH 7.0 to 9.5. The retention volumes of [$^3$H]-EB are higher at low ionic strength (5-mM ammonium acetate) and decrease as the ionic concentration of the mobile phase increases.

Stability and Reproducibility of nAChR Columns:

One α3/β4 nAChR-IAM column is used continuously over a ten day period and then stored for 40 days at 4° C. The retention volumes for 60 μM [$^3$H]-EB are 9.5±0.05 ml (from day 1 to day 10) and 9.7±0.08 ml (day 50). The relative affinities of EB and (−) nicotine obtained on three α3/β4 nAChR-IAM columns prepared from different batch of cell lines are reproducible as shown in the table below, although the retention volumes of EB at the same concentration differed from column to column.

| Column size (cm) | $K_d$ of EB (nM) | $K_d$ of (−)-Nicotine (nM) | Binding sites (pmol/ml bed) |
|---|---|---|---|
| 0.5 × 1.8 | 0.34 ± 0.04 | 52 ± 10 | 7.5 ± 0.2 |
| 0.5 × 1.3 | 0.27 ± 0.05 | 88 ± 33 | 13.5 ± 0.3 |
| 0.5 × 1.7 | 0.21 ± 0.06 | 130 ± 45 | 15.0 ± 0.4 |

Preparation of Immobilized GABAA and Nicotinic Acetylcholine Receptors on an IAM Support from Rat Whole Brain:

Rat whole brain (4 brains) is homogenized in 30 ml of TRIS-HCl buffer [50 mM, pH 7.4] containing 5 mM EDTA, 3 mM benzamidine and 0.2 mM PMSF (Phenyl methyl sulfonyl chloride) for 3×20 seconds using a Brinkman Polytron at setting 6. The mixture is kept in an ice bath for 20 seconds between each homogenization step to prevent excessive heating of the tissue. Homogenized brain tissue is centrifuged for 10 min/4° C. at 21,000 rpm. Supernatant is removed using a Pasteur pipette and discarded. The pellets are suspended in 10 ml of Solubilization Buffer containing 100 mM NaCl, 2 mM $MgCl_2$, 3 mm $CaCl_2$, 5 mM KCl, 2% Na-cholate and 10 μg/ml Leupeptin in TRIS-HCl buffer [50 mM, pH 7.4]. The resulting mixture is stirred for 12 h/4° C. and centrifuged at 21,000 rpm.

Supernatant (receptor-cholate suspension) is mixed with 200 mg of dried IAM-PC packing material and stirred gently for 1 h/25° C., transferred into dialysis tubing and dialyzed for 48 h/4° C. against 3×600 ml of Dialysis Buffer containing 5 mM EDTA, 100 mM NaCl, 0.1 mM $CaCl_2$ and 0.1 mM PMSF in TRIS-HCl buffer [50 mM, pH 7.4].

The receptor-IAM-PC is centrifuged for 3 min/4° C. at 2,000 rpm. Supernatant is discarded. Pellets are washed with TRIS-HCl buffer [50 mM, pH 7.4] and centrifuged until the supernatant is clear. The resulting pellets are used to pack the column.

Determination of Binding Affinities to the Immobilized GABAA Receptor (GR) Using Frontal Chromatography:

The GR-IAM particles are packed in a HRS/2 glass column and connected to a HPLC pump. [$^3$H]-Flunitrazepam ([$^3$H]-FTZ), a GABAA receptor ligand, is used as a marker and an on-line flow scintillation detector (525 TR) monitored the elution profile. All chromatographic experiments are performed at flow rate 0.4 ml/min at room temperature. In frontal chromatography, a 50-ml sample superloop is used to apply a series of [$^3$H]-FTZ concentrations through the GR-column to obtain elution profiles showing a front and plateau regions. The chromatographic data is summed up in 1-min intervals and smoothed using the Microsoft Excel program with a 10 point moving average.

When the GABAA receptor ligand diazepam (DAZ) is added to the mobile phase, the retention volume of [$^3$H]-FTZ is reduced in to proportion to the concentration of DAZ in the mobile phase. These results indicate that the retention of FTZ on the GR-IAM is due to specific interactions with the immobilized GABAA receptor. The dissociation constants ($K_d$) of FTZ and DAZ are determined on the GR-IAM. The calculated $K_d$ of FTZ and DAZ obtained by frontal chromatography are consistent with those determined by classical binding assays, as shown in the table below.

| Ligand | Frontal Chromatography | Binding Assays |
|---|---|---|
| Flunitrazepam | 1.3 | 1.7 |
| Diazepam | 1.0 | 1.3 |

Production and Purification of the ER-LBD.

The Estrogen Receptor (ER) is part of the Nuclear Receptor Superfamily. It is made up of five different regions: A, B, C, D, and E. The E region, also known as, the ligand binding domain (LBD) is where the agonists and antagonists bind. The ER-LBD has been expressed in yeast and also in bacteria via a fusion product between protein A and the LBD. The Production of recombinant Estrogen Receptor Protein is described: The DNA sequence coding for the ligand binding domain of the human estrogen receptor a protein (amino acids 302-595) is obtained by PCR using the full length cDNA as the template. The product of the PCR reaction is subcloned into the pRSET plasmid in frame with a 6 histidine tag on the N-terminal end of the protein. The His tag is used for the purification of the protein from the bacterial proteins. The plasmid is transformed into the BL21 codon+ bacteria. The bacteria are grown in standard LB Broth to an optical density at X=600 of ~1.5.

The bacteria are harvested by centrifugation and frozen at −80° C. until further purification. The bacteria pellets are lysed in a urea/HEPES lysis buffer by sonication and clarified by centrifugation and filtration. The lysate is loaded onto a 5 ml Ni-NTA nickel affinity column that is preequilibrated with the urea/HEPES lysis buffer. The Ni-NTA column selectively binds proteins with the 6-His tag. The nontagged proteins are washed off the column with the urea/HEPES buffer. The estrogen receptor is refolded on the column by gradually changing the buffer to a PBS (phosphate buffered saline) buffer. Finally, the estrogen receptor protein is eluted with a PBS buffer containing imidazole, which competes with the His tag for binding to the Ni-NTA column. The fractions containing the estrogen receptor protein are determined by gel electrophoresis and staining with Gelcode Blue and by western blot analysis using a antibody against the human estrogen receptor. The concentration of protein purified is determined via bicinchoninic acid (BAC) protein assay.

Binding Activity of the ER-LBD.

A binding assay is carried out to determine the activity of the fusion protein. The classical method using dextran•coated charcoal is initially used and gives the activity of the protein. However, the method is improved with the use of Nickel-NTA agarose beads to isolate the fusion protein. Roughly 200 pmoles of protein is placed per tube. For total binding, varying concentrations of [$^3$H]-estradiol is added and for nonspecific binding a 200 fold excess of the cold estradiol is added prior to the addition of the radiolabeled estradiol. The solutions are incubated at room temperature for 2 hours. Following incubation, the Nickel-NTA is added. After one wash, the protein is displaced with imidazole. The $K_d$ is determined to be approximately 3.4 nM (an average $K_d$ of several experiments). Although estradiol had a slightly stronger affinity for the native ER (0.2 nM), this is sufficient.

Immobilization of the ER-LBD.

The initial immobilization of the isolated fusion protein is carried out using a silica based immobilized artificial membrane: IAM.PC. This membrane contains a silica core, which is attached to a hydrophobic spacer with a polar head group. The procedure for immobilization of the protein onto these membranes is known in the art. Varying concentrations of IAM are used to determine the optimal conditions for immobilization. It is determined that 25 mg of IAM is optimal with 35% incorporation.

However, upon testing for activity it becomes apparent that [$^3$H]-estradiol is not only binding to the protein but also to the hydrophobic layer of the membrane. Increasing the ethanol concentration in solution does not significantly reduce the binding to the membrane. Using a modified IAM stationary phase, the IAM-MG, that is more hydrophilic only slightly reduces the nonspecific binding.

The ER-LBD is then immobilized in a new column format containing a silica backbone and a hydrophobic spacer (C 10). The ER-LBD is immobilized and retained its binding activity but the nonspecific binding of [$^3$H]-estradiol is still to great for effective use of the column. The C 10 spacer is replaced by a hydrophilic spacer and the nonspecific binding of [$^3$H]-estradiol is eliminated and the ER-LBD-SP column is synthesized.

The $K_d$ of the estradiol marker ligand is then determined on-line using the ER-LBD-SP column. The ER-LBD-SP column is connected with on-line flow scintillation monitoring (kadiometric FLO-ONE Beta 500 TR instrument, Packard Instrument Co., Meridien, Conn.) and run at room temperature for 97.5 minutes at a flow rate of 0.2 mL/min. The system setup is as described by Zhang, et al., Immobilized Nicotinic Receptor Stationary Phase For On-Line Liquid Chromatographic Determination of Drug-Receptor Affinities, Anal. Biochem. 264, 22 (1998). 18 mL samples of 0.5 nM [$^3$H]-Estradiol ([$^3$H]-E2) supplemented with a range of concentration of cold Estradiol (0-7 nM) are run by frontal chromatography. The elution volume data is used to calculate the dissociation constant of the ligand. The $K_d$ value of estradiol is calculated by nonlinear regression with Prism (GraphPad Software) using one site binding equation: Y=Bmax [E2] total/($K_d$+[E2]total). The $K_d$ values of estradiol is calculated as previously described to be (0.189±0.06) nM. The radioactive signal is recorded every 6 seconds by an on-line flow scintillation detector.

Preparation of the ER-LBD:

The recombinant ER-LBD is obtained and purified as described above.

Immobilization of the ER-LBD:

The ER-LBD is then immobilized in the micromachined capillaries. The immobilization is accomplished through activation of the silanol groups on the silica chips using dicyclohexylcarbodiimide (DCC) and then coupling of the C2 spacer with a free carboxyl group to the activated surface. The ER-LBD is then bound to the derivatized surface using the procedures developed in the previous studies with the liquid chromatographic stationary phase composed of silica gel beads. The amount of protein immobilized on the surface of the microchannels is determined by analysis of the protein content of the binding solution before and after exposure to the microchannels.

If the initial experimental approach to the immobilization of ER-LBD is not successful the following procedures are investigated: 1) if the problem exists at the during the activation of the silanol groups at the silica surface, DCC is replaced by dimethylaminopyridine (DMAP); 2) if the problem arises from the C2 spacer, C3 to C4 spacers are examined; 3) if a problem exists with the immobilization to the new surface, an epoxide activated approach is explored by a method such as described in J. B. Wheatley, et al.: Salt-induced immobilization of affinity ligands onto epoxide-activated supports, J. Chromatogr. A, 849, 1 (1999); D. Zhou, et al.: Membrane affinity chromatography for analysis and purification of biopolymers, Chromatographia, 50, 27 (1999), or an approach utilizing streptavidin-biotinylation such as described by L. A. Paige, et al.: Estrogen receptor (ER) modulators each induce distinct conformational changes in ERa and ERβ. Proc. Nat. Acad. Sci., 96, 3999 (1999).

Binding Activity of the Immobilized ER-LBD:

The binding activity of the immobilized ER-LBD is determined using [$^3$H]-estradiol (0.005 nM in phosphate buffer [0.1 M, pH 7.4] ([$^3$H]-E2) supplemented with a range of concentration of cold estradiol to produce a range of from 0.001 to 0.050 nM in phosphate buffer [0.1 M, pH 7.4]). The solutions containing the [$^3$H]E2 are applied to the microchannels containing the immobilized ER-LBD, microchannels containing the immobilized support (without the ER-LBD, a positive control) and bare microchannels (negative control). The solution containing microchannels is incubated at room temperature for 30 minutes. The channels are then washed three times with phosphate buffer [0.1 M, pH 7.4], the washing is collected and assayed for [$^3$H]-E2 content using a scintillation detector. The IQ value of E2 is calculated by nonlinear regression with Prism (GraphPad Software) using one site binding equation: Y=Bmax [E2]total/($K_d$+[E2]total). The observed binding affinities and extent of binding is compared to the data from parallel binding studies carried out using an equivalent concentration of non-immobilized ER-LBD. These studies will yield binding affinity/mg immobilized ER-LBD indices (BAI) which is used to characterize the immobilized receptor.

Optimization and Reproducibility of the Immobilization:

The immobilization of the ERLBD is optimized through the investigation of the effect of ER-LBD concentration, reaction time, temperature and chemistry used in the immobilization. Each of the variables is independently investigated in a step-wise optimization approach. The outcome of each iteration is assessed using the BAI. Once an optimum immobilization procedure has been determined, the intra-day and inter-day reproducibility of the procedure is determined. A variance of no greater than 10% is deemed acceptable. If this cannot be achieved under the initially determined "optimal" conditions, other previously determined conditions is investigated using the BIA as the selecting variable.

Determination of the limits of quantitation and detection of the immobilized ER-LBD chip: The estradiol ligand is derivatized with fluorescein-5-maleimide to produce the fluorescent-ligand {E2-FM} which is used in the clinical patch. If this fluorescent-tag does not produce enough sensitivity, other agents are utilized. The immobilized ER-LBD chip is suspended over and then brought into surface contact with solutions containing E2. The concentrations of the E2 solutions are serially diluted from the initial concentration of 0.050 nM until displacement of E2-FM can no longer be observed. The measured optical density at $\lambda$ex=488 nm and $\lambda$em=520 nm is plotted against the E2 concentrations of the test solutions to construct standard curves. Standard inter-day and infra-day validation studies are conducted to establish the reproducibility of the measurements, the lower limits of quantitation and the lower limits of detection. Once this has been established, the chip is ready for clinical testing.

Preparation of the AR-LBD:

The androgen receptor ligand binding domain {AR-LBD} fusion protein is produced and purified following known procedures. Once the protein is expressed and purified, the binding affinity of the AR-LBD is determined by conventional methods following the procedure described for the ER-LBD.

Preparation of the Immobilized AR-LBD Chip and Validation of its Activity:

The immobilization of the AR-LBD, determination of the binding activity of the immobilized ERLBD, determination of the limits of quantitation and detection as well as the initial clinical validation is carried out based upon the results obtained with the ER-LBD.

The protein is immobilized in a similar fashion as the ER-LBD, and the $K_d$ is determined by frontal chromatography. The stability of the column is also determined.

The immobilization of these receptors allows for rapid screening and determination of presence of biologically active/inactive compounds on the estrogen and/or androgen receptors.

The recombinant ER-LBD is obtained and purified as described above.

Immobilization of the ER-LBD:

The AR-LBD is then immobilized following the procedures described above for the ER-LBD.

The clinical trials described herein determine the analytical precision and accuracy of methods to determine estrogen and testosterone via transdermal sampling in comparison with validated plasma assays. Validated plasma ELISA assays for estrogen and testosterone with acceptable limits of detection and quantification and with acceptable intra- and inter-day coefficients of variation are used to compare with these assays in the clinical settings described in the four trials outlined in detail below.

Clinical Trial 1: a Pilot Trial Correlating Estrogen Concentrations in Plasma and Interstitial Fluid in Pre and Post-Menopausal Women.

In order to validate the analytical sensitivity of transdermal sampling to measure estrogen, eight healthy, menstruating women and eight healthy post-menopausal women who are taking no estrogen-containing medications are followed for two months to measure the estrogen concentrations in their plasma or interstitial fluid. Concentrations of estrogen in the plasma is determined by a validated clinical ELISA assay, routinely used in clinical settings. These concentrations are compared to those determined in interstitial fluid using estrogen receptor-based assays using the HW monitoring device. Plasma and interstitial fluid concentrations are measured daily during the period from the end of after menstruation until 10 days afterward in menstruating women and over a ten day period in post-menopausal women. Two groups of women are recruited: a group of eight women who are pre-menopausal and who, by history, experience regular menstrual cycles; and a group of women who have passed through menopause.

Inclusion Criteria.

Group 1: women who are over the age of 21 years and under the age of 40 years. Group 2: women who are over the age of 55 and under the age of 75. All women must conform with the following: (1) taking no prescription medications or natural products intended to produce estrogen like effects (for example, ginseng or black kohosh); (2) with clinically normal laboratory values for complete blood counts, serum chemistries (Na, K, CI, $HCO_3$, BUN, glucose and creatinine) and clinically normal liver enzyme profiles: SGOT, SGPT, alkaline phosphatase and bilirubin; (3) ability to understand and carry out a signed informed consent describing this protocol.

Exclusion Criteria.

The following individuals are excluded from the study: (1) smokers; (2) impaired liver or renal function as demonstrated by serum SGOT, SGPT or bilirubin above the normal range of laboratory values, or serum creatinine greater than 1.5 mg/dL; (3) positive urine drug screen; (4) subjects who test positive for Human Immunodeficiency Virus or hepatitis; (5) subjects who have taken an investigational drug within 30 days of study start; (6) subjects taking any enzyme inducing or inhibiting medications (for example, rifampin or phenyloin) for 30 days prior to dosing; and (7) subjects who, in the opinion of the Investigator, is noncompliant with the protocol requirements.

Restrictions include that subjects are instructed to refrain from the following: (1) taking any prescription medications for two weeks prior to dosing; (2) consuming caffeine and/or xanthine containing products and alcohol from at least 48 hours prior to Study Day 1 until after the last blood sample has been collected; (3) smoking; (4) strenuous exercise during the entire study to avoid dislocation of the measuring device.

Once a subject has consented to participate in the study, the following procedures are conducted. Screening procedures are conducted within 21 days of study initiation and include: medical history and physical examination; review of inclusion and exclusion criteria; blood and urine specimen collection; analysis of blood sample for hematology, serum chemistry, liver enzymes, HIV and hepatitis B and C; and analysis of urine sample for screening of drugs of abuse.

Subsequent to inclusion in the study, subject will undergo the following procedures: subjects arrive at the testing facility at approximately 9 a.m. in the morning. While the precise date is not important for post-menopausal women, menstruating women are asked to report on the last day of their regular period. At this time estrogen levels are low and the detection limits of the assays is appropriately tested. Vital signs (heart rate, respiratory rate, blood pressure and temperature) are recorded. The portable biomedical monitoring device is placed on a forearm and attached securely with tape. Recording occurs via a 50 micron cauterized lesion in the skin made by a small needle on the underside of the monitor that is not visible. The monitor is checked to ensure that it is recording. Vital signs (heart rate, respiratory rate, blood pressure and temperature) are recorded.

A single sample of venous blood (5 cc or one teaspoon) is drawn from a forearm vein for the measurement of estrogen while the subject is supine. The device is instructed to measure estrogen for periods of 0.25, 0.5, 1, 1.5, 2, 3, 6, and 8 hours in order to test the optimal time required. Additional blood samples are drawn 4 hours and eight hours after the first. The tape and device is removed. Patients are then discharged and allowed to return home before returning at 9 a.m.

the next morning. This procedure is repeated on the following 9 days for a total of 10 days with each subject.

Blood Sampling Schedule.

Five mL venous blood samples are collected in vacutainers containing EDTA on days 1 through 10 in the manner described above. The total number of blood draws during the course of the study including the screening and exit samples, is 35, (Thirty study draws and five screening draws for hematology, chemistry, liver enzymes, HIV and Hepatitis and C respectively.) and the total volume of blood drawn does not exceed 200 mL.

Vital signs (heart rate, respiratory rate, blood pressure and temperature) are taken before and after placement of the device and before and after each blood draw on days 1 through 10.

Patients are encouraged to report any notable irritation on the arm where the device is placed. A physician is constantly available to subjects enrolled in the study for concerns related to bruising or infection in the skin due to multiple blood draws.

Estrogen concentrations determined using plasma ELISA is compared with the values obtained using the portable biomedical monitor. If the correlation coefficient is >0.8 with a significance $p<0.05$ the measurements are deemed valid.

A Pilot Trial Correlating Testosterone Concentrations in Plasma and Interstitial Fluid in Men.

Ten healthy men, chosen to represent a range of ages between 21 and 70 years old and who are taking no medications have plasma and interstitial fluid testosterone concentrations measured daily for 5 consecutive days both by validated plasma assay and by transdermal sampling using the portable biomedical monitoring device.

Inclusion Criteria.

Men who are over the age of 21 and under the age of 75. All men must conform with the following: (1) taking no prescription medications or natural products intended to produce testosterone like effects (for example, androstenedione or DHEA); (2) with clinically normal laboratory values for complete blood counts, serum chemistries (Na, K, CI, HCO3, BUN, glucose and creatinine) and clinically normal liver enzyme profiles: SGOT, SGPT, alkaline phosphatase and bilirubin; and (3) ability to understand and carry out a signed informed consent describing this protocol.

Exclusion Criteria.

The following individuals are excluded from the study: (1) smokers; (2) impaired liver or renal function as demonstrated by serum SGOT, SGPT or bilirubin above the normal range of laboratory values, or serum creatinine greater than 1.5 mg/dL; (3) positive urine drug screen; (4) subjects who test positive for Human Immunodeficiency Virus or hepatitis.

Restrictions include subjects are instructed to refrain from the following: (1) smoking; and (2) strenuous exercise during the entire study to avoid dislocation of the measuring device.

Once a subject has consented to participate in the study, the following procedures are conducted: Screening procedures are conducted within 21 days of study initiation and include: medical history and physical examination; review of inclusion and exclusion criteria; blood and urine specimen collection; analysis of blood sample for hematology, serum chemistry, liver enzymes, HIV and hepatitis B and C; and analysis of urine sample for screening of drugs of abuse.

Subsequent to inclusion in the study, subject will undergoes the following procedures: Subjects arrive at the testing facility at approximately 9 a.m. in the morning. Vital signs (heart rate, respiratory rate, blood pressure and temperature) are recorded. The portable biomedical monitoring device is placed on a forearm and attached securely with tape. Recording occurs via a 50 micron cauterized lesion in the skin made by a small needle on the underside of the monitor that is not visible. The monitor is checked to ensure that it is recording. Vital signs (heart rate, respiratory rate, blood pressure and temperature) are recorded.

A single sample of venous blood (5 cc or one teaspoon) is drawn from a forearm vein for the measurement of testosterone while the subject is supine. The device is instructed to measure estrogen for periods of 0.25, 0.5, 1, 1.5, 2, 3, 6, and 8 hours in order to test the optimal time required. Additional blood samples are drawn 4 hours and eight hours after the first. The tape and device is removed. Patients are then discharged and allowed to return home before returning at 9 a.m. the next morning. This procedure is repeated on the following 4 days for a total of 5 days with each subject.

Five mL venous blood samples are collected in Vacutainers containing EDTA on Days 1 through 5 in the manner described above. The total number of blood draws during the course of the study including the screening and exit samples, is 20, (Fifteen study draws and five screening draws for hematology, chemistry, liver enzymes, HIV and Hepatitis and C respectively.) and the total volume of blood drawn does not exceed 200 mL.

Vital signs (heart rate, respiratory rate, blood pressure and temperature) are taken before and after placement of the device and before and after each blood draw on days 1 through 5.

Patients are encouraged to report any notable irritation on the arm where the device is placed. A physician is constantly available to subjects enrolled in the study for concerns related to bruising or infection in the skin due to multiple blood draws.

Testosterone concentrations determined using plasma ELISA is compared with the values obtained using the portable biomedical monitor. If the correlation coefficient is >0.8 with a significance $p<0.05$ the measurements are deemed valid.

The purpose of this third clinical trial is to administer appropriate concentrations of estrogen to postmenopausal women who are healthy volunteers and to measure the resulting concentrations. Estrogen is administered in microgram pulses over a period of 3 days after a 3-day run-in for baseline measurement using the optimal machine settings for the monitor as defined above.

The purpose of this fourth clinical trial is to administer appropriate concentrations of testosterone to men between the ages of 55 and 75 years who are healthy volunteers and to measure the resulting concentrations. Testosterone is administered in microgram pulses over a 5 day period after a 3 day run-in period that is used to determine baseline testosterone concentrations in these men before the administration of testosterone. The resulting concentrations is determined using the analytical specifications as defined above.

All of the above-cited patents, publications, and references are hereby expressly incorporated by way of reference in their respective entireties.

It should be apparent to one of ordinary skill in the art that other embodiments can be readily contemplated in view of the teachings of the present specification. Such other embodiments, while not specifically disclosed nonetheless fall within the scope and spirit of the present invention. Thus, the present invention should not be construed as being limited to the specific embodiments described above, and is solely defined by the following claims.

What is claimed is:

1. A transdermal monitoring and fluid delivery microsystem, comprising:

a substrate including a power source, logic module and at least one connection receptacle;

at least one removable transdermal monitoring subsystem mounted to the at least one connection receptacle, the at least one transdermal monitoring subsystem including at least one analyte detector and multiple single-use sampling units, each of the multiple single-use units including:
  a microablation heater for ablating a portion of the stratum corneum of a subject's skin in order to access interstitial fluid from the underlying epidermis; and
  a microchannel for transmitting the accessed interstitial fluid to the at least one analyte detector, wherein the at least one analyte detector communicates detection results to the logic module; and at least one removable microelectromechanical (MEMS) fluid delivery subsystem mounted to the at least one connection receptacle for delivering a fluid to the subject in response to the detection of the analyte by the at least one analyte detector, the MEMS fluid delivery subsystem including means for transdermal fluid delivery to the subject;

wherein the logic module provides fluid delivery instructions to the at least one MEMS fluid delivery subsystem in accordance with the detection results from the at least one analyte detector.

2. The microsystem of claim 1, wherein the at least one analyte detector is configured to detect an analyte of interest selected from the group consisting of glucose, bilirubin, D-amino acids, an insecticide, atropine, pralidoxime, cytokine, dextromethorphan, caffeine, antihistamines, an organophosphate, microbial toxin, inflammatory sequeli to microbial toxin, spore metabolite, prealbumin, C-reactive protein, troponin I, estrogen, and testosterone.

3. The microsystem of claim 2, wherein the at least one analyte detector is configured to detect an amount of analyte of interest in the interstitial fluid of the subject and, further wherein, the logic module determines if the detected amount is at a predetermined level and, when the detected amount is below the predetermined level, the logic module instructs the MEMS fluid delivery subsystem to administer an analyte amount to the subject.

4. The microsystem of claim 1, wherein the fluid is selected from the group consisting of a drug, chemical and target probe.

5. The microsystem of claim 4, wherein the fluid further comprises a physiologically compatible solution.

6. The microsystem of claim 1, wherein the logic module controls operation of each of the multiple single-use sampling units and the MEMS fluid delivery subsystem on-demand.

7. The microsystem of claim 1, further comprising at least one environmental detector in communication with the logic module for sampling one or more target analytes in one of the air and water to which the subject is being exposed and communicating outward analyte detection results to the logic module, wherein the logic module provides fluid delivery instructions to the at least one MEMS drug delivery subsystem in accordance with the detection results from the at least one analyte detector and the outward analyte detection results from the at least one environmental detector.

8. The microsystem of claim 1, further comprising a communication means interconnected with the logic module for telemetrically communicating detection results.

9. A transdermal monitoring and fluid delivery microsystem, comprising:
  a substrate including a power source, logic module, and at least one connection receptacle;

at least one removable transdermal monitoring subsystem mounted to the at least one connection receptacle, the at least one transdermal monitoring subsystem including at least one analyte detector and multiple single-use sampling units, each of the multiple single-use units including:
    a microablation heater for ablating a portion of the stratum corneum of a subject's skin in order to access interstitial fluid from the underlying epidermis; and
    a microchannel for transmitting the accessed interstitial fluid to the at least one analyte detector, wherein the at least one analyte detector communicates detection results to the logic module; and at least one removable microelectromechanical (MEMS) fluid delivery subsystem mounted to the at least one connection receptacle for delivering a fluid to the subject in response to the detection of the analyte by the at least one analyte detector, the MEMS fluid delivery subsystem including multiple individual reservoir capillaries, each of the multiple individual reservoir capillaries containing a predetermined amount of the fluid therein and including a breakable seal closure;

wherein the logic module provides fluid delivery instructions to the at least one MEMS fluid delivery subsystem in accordance with the detection results from the at least one analyte detector.

10. The microsystem of claim 9, wherein the breakable seal closure is formed of a heat responsive material connected to a metallic microheating element and further wherein the heat generated by the metallic microheating element simultaneously ablates a portion of the stratum corneum of a subject's skin to provide access for delivering the fluid to the subject and breaks the breakable seal closure to release the fluid from the reservoir capillary.

11. The microsystem of claim 9, wherein the fluid delivery instructions include instructions for addressing the metallic microheating element.

12. The microsystem of claim 9, wherein the at least one analyte detector is configured to detect an analyte of interest selected from the group consisting of glucose, bilirubin, D-amino acids, an insecticide, atropine, pralidoxime, cytokine, dextromethorphan, caffeine, antihistamines, an organophosphate, microbial toxin, inflammatory sequeli to microbial toxin, spore metabolite, prealbumin, C-reactive protein, troponin I, estrogen, and testosterone.

13. The microsystem of claim 12, wherein the at least one analyte detector is configured to detect an amount of analyte of interest in the interstitial fluid of the subject and, further wherein, the logic module determines if the detected amount is at a predetermined level and, when the detected amount is below the predetermined level, the logic module instructs the MEMS fluid delivery subsystem to administer an analyte amount to the subject.

14. The microsystem of claim 9, wherein the fluid is selected from the group consisting of a drug, chemical and target probe.

15. The microsystem of claim 14, wherein the fluid further comprises a physiologically compatible solution.

16. The microsystem of claim 9, wherein the logic module controls operation of each of the multiple single-use sampling units and the MEMS fluid delivery subsystem on-demand.

17. The microsystem of claim 9, further comprising at least one environmental detector in communication with the logic module for sampling one or more target analytes in one of the air and water to which the subject is being exposed and communicating outward analyte detection results to the logic module, wherein the logic module provides fluid delivery instructions to the at least one MEMS drug delivery subsystem in accordance with the detection results from the at least one analyte detector and the outward analyte detection results from the at least one environmental detector.

18. The microsystem of claim 9, further comprising a communication means interconnected with the logic module for telemetrically communicating detection results.

19. A transdermal monitoring and fluid delivery microsystem, comprising:
- a substrate including a power source, logic module, and at least one connection receptacle;
- at least one removable transdermal monitoring subsystem mounted to the at least one connection receptacle, the at least one transdermal monitoring subsystem including at least one analyte detector and multiple single-use sampling units, each of the multiple single-use units being individually controllable to access and retrieve a sample of interstitial fluid of a subject and provide detection results; and
- at least one removable microelectromechanical (MEMS) fluid delivery subsystem mounted to the at least one connection receptacle for delivering a fluid to the subject in response to the detection of the analyte by the at least one analyte detector, the MEMS fluid delivery subsystem including multiple individual reservoir capillaries, each of the multiple individual reservoir capillaries containing a predetermined amount of the fluid therein and including a breakable seal closure;
- wherein the logic module provides fluid delivery instructions to the at least one MEMS fluid delivery subsystem in accordance with the detection results from the at least one analyte detector.

20. The microsystem of claim 19, wherein the breakable seal closure is formed of a heat responsive material connected to a metallic microheating element and further wherein the heat generated by the metallic microheating element simultaneously ablates a portion of the stratum corneum of a subject's skin to provide access for delivering the fluid to the subject and breaks the breakable seal closure to release the fluid from the reservoir capillary.

* * * * *